US009290560B2

(12) United States Patent
Price-Schiavi et al.

(10) Patent No.: US 9,290,560 B2
(45) Date of Patent: Mar. 22, 2016

(54) SOLUBLE TCR MOLECULES AND METHODS OF USE

(71) Applicant: Altor BioScience Corporation, Miramar, FL (US)

(72) Inventors: Shari A. Price-Schiavi, Westminster, MD (US); Heather J. Belmont, North Miami Beach, FL (US); Kimberlyn F. Card, Pembroke Pines, FL (US); Xiaoyun Zhu, Miami, FL (US); Hing C. Wong, Weston, FL (US)

(73) Assignee: ALTOR BIOSCIENCE CORPORATION, Miramar, FL (US)

( * ) Notice: Subject to any disclaimer, the term of this patent is extended or adjusted under 35 U.S.C. 154(b) by 0 days.

(21) Appl. No.: 14/182,888

(22) Filed: Feb. 18, 2014

(65) Prior Publication Data
US 2014/0378656 A1 Dec. 25, 2014

Related U.S. Application Data

(63) Continuation of application No. 10/985,271, filed on Nov. 10, 2004, now Pat. No. 8,772,451.

(60) Provisional application No. 60/518,790, filed on Nov. 10, 2003.

(51) Int. Cl.
*C07K 1/00* (2006.01)
*C07K 14/00* (2006.01)
*C07K 17/00* (2006.01)
*C07K 14/725* (2006.01)
*A61K 47/48* (2006.01)
*B82Y 5/00* (2011.01)
*C07K 14/55* (2006.01)
*G01N 33/574* (2006.01)
*G01N 33/68* (2006.01)

(52) U.S. Cl.
CPC ....... *C07K 14/7051* (2013.01); *A61K 47/48261* (2013.01); *A61K 47/48269* (2013.01); *A61K 47/48276* (2013.01); *A61K 47/48353* (2013.01); *B82Y 5/00* (2013.01); *C07K 14/55* (2013.01); *G01N 33/57484* (2013.01); *G01N 33/57492* (2013.01); *G01N 33/6875* (2013.01); *C07K 2319/00* (2013.01); *C07K 2319/20* (2013.01); *C07K 2319/30* (2013.01); *C07K 2319/32* (2013.01); *G01N 2333/7051* (2013.01); *G01N 2333/70539* (2013.01)

(58) Field of Classification Search
None
See application file for complete search history.

(56) References Cited

U.S. PATENT DOCUMENTS

| 5,869,270 A | 2/1999 | Rhode et al. |
| 6,309,645 B1 | 10/2001 | Rhode et al. |
| 7,456,362 B2 | 11/2008 | Allais et al. |
| 2002/0034513 A1 | 3/2002 | Rhode et al. |
| 2002/0058235 A1 | 5/2002 | Dinnerstein |
| 2002/0091079 A1 | 7/2002 | Rhode et al. |
| 2002/0198144 A1 | 12/2002 | Wong et al. |
| 2003/0082719 A1 | 5/2003 | Schumacher et al. |
| 2003/0144474 A1 | 7/2003 | Weidanz et al. |
| 2003/0171552 A1 | 9/2003 | Weidanz et al. |
| 2004/0253632 A1 | 12/2004 | Rhode et al. |
| 2006/0135418 A1 | 6/2006 | Jakobsen et al. |

FOREIGN PATENT DOCUMENTS

| CN | 1306572 A | 8/2001 |
| JP | 2003518377 T | 6/2003 |
| WO | WO 8809344 A1 * | 12/1988 |
| WO | WO-9618105 | 6/1996 |
| WO | WO 9918129 A1 * | 4/1999 |
| WO | WO-9960119 A2 | 11/1999 |
| WO | WO-9960120 A2 | 11/1999 |
| WO | WO 0023087 A1 * | 4/2000 |
| WO | WO-0148145 A2 | 7/2001 |
| WO | WO 0193913 A2 * | 12/2001 |
| WO | WO-2004018619 | 3/2004 |
| WO | WO 2009117117 A1 * | 9/2009 |

OTHER PUBLICATIONS

Brawley et al., 2002, J. Immunol. vol. 168: 3894-3901.*
Kieke et al., 1999, PNAS, vol. 96: 5651-5656.*
Portolano et al., 1993, J. Immunol. vol. 150: 880-887.*
Accession No. CAA25652.1, 1995, pp. 1-3.
Altman JD, Moss PA, Goulder PJ, Barouch DH, McHeyzer-Williams MG, Bell JI, McMichael AJ, Davis MM (1996) Phenotypic analysis of antigen-specific T lymphocytes. Science 274: 94.
Anderson KS, Alexander J, Wei M, Cresswell P (1993) Intracellular transport of class I MHC molecules in antigen processing mutant cell lines. J Immunol 151: 3407.
Bauer RJ, Dedrick RL, White ML, Murray MJ, Garovoy MR (1999) Population pharmacokinetics and pharmacodynamics of the anti-CD11a antibody hu1124 in human subjects with psoriasis. J Pharmacokinet Biopharm 27: 397.
Becker JC, Varki N, Gillies SD, Furukawa K, Reisfeld RA (1996) Long-lived and transferable tumor immunity in mice after targeted interleukin-2 therapy. J Clin Invest 98: 2801.
Chang Chien-Hsing, Sharkey Robert M, Rossi Edmund A, Karacay Habibe, McBride William, Hansen Hans J, Chatal Jean-Francois, Barbet Jacques, and Goldenberg David M (2002) Molecular Advances in Pretargeting Radioimunotherapy with Bispecific Antibodies. Molecular Cancer Therapeutics vol. 1: 553.
Chung S, Wucherpfennig KW, Friedman SM, Hafler DA, Strominger JL (1994) Functional three-domain single-chain T-cell receptors. Proc Natl Acad Sci U S A 91: 12654.

(Continued)

*Primary Examiner* — Amy Juedes
(74) *Attorney, Agent, or Firm* — Mintz Levin Cohn Ferris Glovsky and Popeo, P.C.; Peter F. Corless, Esq.; Daniel W. Clarke

(57) ABSTRACT

Disclosed are compositions and methods for detecting cells or tissue comprising a peptide antigen presented in the context of an MHC or HLA complex. The invention has a wide range of applications including providing a highly sensitive method for detecting cancer cells.

10 Claims, 22 Drawing Sheets

(56) References Cited

OTHER PUBLICATIONS

Cohen et al., 2002, Cancer Research, vol. 62: 5835-5844.
Donohue JH, Rosenberg SA (1983) The fate of interleukin-2 after in vivo administration. J Immunol 130: 2203.
Dummer R, Gore ME, Hancock BW, Guillou PJ, Grobben HC, Becker JC, Oskam R, Dieleman JP, Burg G (1995) A multicenter phase II clinical trial using dacarbazine and continuous infusion interleukin-2 for metastatic melanoma. Clinical data and immunomonitoring. Cancer 75: 1038.
Engel I, Ottenhoff TH, Klausner RD (1992) High-efficiency expression and solubilization of functional T cell antigen receptor heterodimers. Science 256: 1318.
Epel Malka, Ellenhorn Joshua D, Diamond Don J, Reiter Yoram (2002) A functional recombinant single-chain T cell receptor fragment capable of selectively targeting antigen-presenting cells. Cancer Immunol Immunother 51: 565.
Gregoire C, Rebai N, Schweisguth F, Necker A, Mazza G, Auphan N, Millward A, Schmitt-Verhulst AM, Malissen B (1991) Engineered secreted T-cell receptor alpha beta heterodimers Proc Natl Acad Sci U S A 88: 8077.
Grimm EA, Mazumder A, Zhang HZ, Rosenberg SA (1982) Lymphokine-activated killer cell phenomenon. Lysis of natural killer-resistant fresh solid tumor cells by interleukin 2-activated autologous human peripheral blood lymphocytes. J Exp Med 155: 1823.
Grussenmeyer T, Scheidtmann KH, Hutchinson MA, Eckhart W, Walter G (1985) Complexes of polyoma virus medium T antigen and cellular proteins. Proc Natl Acad Sci U S A 82: 7952.
Hank JA, Albertini MR, Schiller J, Sondel PM (1993) Activation of multiple effector mechanisms to enhance tumor immunotherapy. J Immunother 14: 329.
Hank JA, Robinson RR, Surfus J, Mueller BM, Reisfeld RA, Cheung NK, Sondel PM (1990a) Augmentation of antibody dependent cell mediated cytotoxicity following in vivo therapy with recombinant interleukin 2. Cancer Res 50: 5234.
Hank JA, Sosman JA, Kohler PC, Bechhofer R, Storer B, Sondel PM (1990b) Depressed in vitro T cell responses concomitant with augmented interleukin-2 responses by lymphocytes from cancer patients following in vivo treatment with interleukin-2. J Biol Response Mod 9: 5.
Hank JA, Surfus J, Gan J, Chew TL, Hong R, Tans K, Reisfeld R, Seeger RC, Reynolds CP, Bauer M, et al. (1994) Treatment of neuroblastoma patients with antiganglioside GD2 antibody plus interleukin-2 induces antibody-dependent cellular cytotoxicity against neuroblastoma detected in vitro. J Immunother 15: 29.
Harlow et al., 1988, Antibodies a Laboratory Manual, p. 321-322.
Harvill ET, Fleming JM, Morrison SL (1996) In vivo properties of an IgG3-IL-2 fusion protein. A general strategy for immune potentiation. J Immunol 157: 3165.
Harvill ET, Morrison SL (1995) An IgG3-IL2 fusion protein activates complement, binds Fc gamma RI, generates LAK activity and shows enhanced binding to the high affinity IL-2R. Immunotechnology 1: 95.
Herberts Carla A, Stittelaar Koert J, van der Heeft Ed, van Gaans-van den Brink Jacqueline, Poelen Martien C.M., Roholl Paul JM, van Alphen Loek JW, Melief Cornelius JM, de Jong Ad PJ M, van Els Cécile AC M (2001) A measles virus glycoprotein-derived human CTL epitope is abundantly presented via the proteasomal-dependent MHC class I processing pathway. Journal of General Virology 82: 2131.
Hilyard KL, Reyburn H, Chung S, Bell JI, Strominger JL (1994) Binding of soluble natural ligands to a soluble human T-cell receptor fragment produced in Escherichia coli. Proc Natl Acad Sci U S A 91: 9057.
Hinds PW, Finlay CA, Quartin RS, Baker SJ, Fearon ER., Vogelstein B, Levine AJ (1990) Mutant p53 DNA clones from human colon carcinomas cooperate with ras in transforming primary rat cells: a comparison of the "hot spot" mutant phenotypes. Cell Growth Differ 1: 571.
Holler Phillip D, Chlewicki Lukasz K and Kranz David M (2002/2003) TCRs with high affinity for foreign pMHC show self-reactivity. http://www.nature.com/natureimmunology; Nature Immunol vol. 4 No. 1.
Hoffmann, Thomas K. et al., "Competition of Peptide-MHC Class I Tetrameric Complexes with Anti-CD3 Provides Evidence for Specificity of Peptide binding to the TCR Complex", Cytometry, vol. 41, pp. 321-328 (2000).
Holmes et al., Preparation of cells and Reagents for Flow Cytometry, Current Protocols in Immunology, 5.3.1-5.3.24.
Hurford RK Jr, Dranoff G, Mulligan RC, Tepper RI (1995) Gene therapy of metastatic cancer by in vivo retroviral gene targeting. Nat Genet 10: 430.
Huston JS, Levinson D, Mudgett-Hunter M, Tai MS, Novotny J, Margolies MN, Ridge RJ, Bruccoleri RE, Haber E, Crea R, et al (1988) Protein engineering of antibody binding sites: recovery of specific activity in an anti-digoxin single-chain Fv analogue produced in Escherichia coli. Proc Natl Acad Sci U S A 85: 5879.
Iggo R, Gatter K, Bartek J, Lane D, Harris AL (1990) Increased expression of mutant forms of p53 oncogene in primary lung cancer. Lancet 335: 675.
Kendra K, Gan J, Ricci M, Surfus J, Shaker A, Super M, Frost JD, Rakhmilevich A, Hank JA, Gillies SD, Sondel PM (1999) Pharmacokinetics and stability of the ch14.18-interleukin-2 fusion protein in mice. Cancer Immunol Immunother 48: 219.
Kieke et al., 2001, J. Mol. Biol. vol. 307: 1305-1315.
Klausner RD, Lippincott-Schwartz J, Bonifacino JS (1990) The T cell antigen receptor: insights into organelle biology. Annu Rev Cell Biol 6: 403.
Lebowitz Michael S, O'Herrin Sean M, Hamad Abdel-Rahim A, Fahmy Tarek, Marguet Didier, Barnes Nicholas C, Pardoll Drew, Bieler Joan G, and Schneck Jonathan P (1999) Soluble, High-Affinity Dimers of T-Cell Receptors and Class II Major Histocompatibility Complexes: Biochemical Probes for Analysis and Modulation of Immune Responses. Cellular Immunology 192: 175.
Lewis LD, Cole BF, Wallace PK, Fisher JL, Waugh M, Guyre PM, Fanger MW, Curnow RT, Kaufman PA, Ernstoff MS (2001) Pharmacokinetic-pharmacodynamic relationships of the bispecific antibody MDX-H210 when administered in combination with interferon gamma: a multiple-dose phase-I study in patients with advanced cancer which overexpresses HER-2/neu. J Immunol Methods 248: 149.
Lin AY, Devaux B, Green A, Sagerstrom C, Elliott JF, Davis MM (1990) Expression of T cell antigen receptor heterodimers in a lipid-linked form. Science 249: 677.
Lode HN, Xiang R, Dreier T, Varki NM, Gillies SD, Reisfeld RA (1998) Natural killer cell-mediated eradication of neuroblastoma metastases to bone marrow by targeted interleukin-2 therapy. Blood 91: 1706.
Lode HN, Xiang R, Varki NM, Dolman CS, Gillies SD, Reisfeld RA (1997) Targeted interleukin-2 therapy for spontaneous neuroblastoma metastases to bone marrow. J Natl Cancer Inst 89: 1586.
Loftus et al., 1998, Canc. Res. vol. 58: 2433-2436.
Lustgarten J, Marks J, Sherman LA (1999) Redirecting effector T cells through their IL-2 receptors. J Immunol 162: 359.
McLaughlin R, O'Hanlon D, McHale T, Connolly CE, Given HF (2001) Prognostic implications of p53 and bcl-2 expression in 108 women with stage two breast cancer. Ir J Med Sci 170: 11.
Mosquera et al., 2005, J. Immunol. vol. 174:4381-4388.
Motzer RJ, Rakhit A, Ginsberg M, Rittweger K, Vuky J, Yu R, Fettner S, Hooftman L (2001) Phase I trial of 40-kd branched pegylated interferon alfa-2a for patients with advanced renal cell carcinoma. J Clin Oncol 19: 1312.
Motzer RJ, Rakhit A, Schwartz LH, Olencki T, Malone TM, Sandstrom K, Nadeau R, Parmar H, and Bukowski R (1998) Phase I Trial of Subcutaneous Recombinant Human Interleukin-12 in Patients with Advanced Renal Cell Carcinoma. Clinical Cancer Research vol. 4: 1183.
Nastala CL, Edington HD, McKinney TG, Tahara H, Nalesnik MA, Brunda MJ, Gately MK, Wolf SF, Schreiber RD, Storkus WJ, et al. (1994) Recombinant IL-12 administration induces tumor regression in association with IFN-gamma production. J Immunol 153: 1697.

(56) References Cited

OTHER PUBLICATIONS

Nobs Leila, Buchegger Franz, Gurny Robert, Allémann Eric (2004) Current Methods for Attaching Targeting Ligands to Liposomes and Nanoparticles. Journal of Pharmaceutical Sciences, vol. 93, No. 8: 1980.
O'Herrin Sean M, Lebowitz Michael S, Bieler Joan G, al-Ramadi Basel K, Utz Ursula, Bothwell Alfred LM, and Schneck Jonathan P (1997) Analysis of the Expression of Peptide-Major Histocompatibility Complexes Using High Affinity Soluble Divalent T Cell Receptors. J. Exp. Med., vol. 186, No. 8: 1333.
Pardoll DM (1995) Paracrine cytokine adjuvants in cancer immunotherapy. Annu Rev Immunol 13: 399.
Pascolo Steve, Schirle Markus, Gückel Brigitte, Dumrese Tilman, Stumm Susanne, Kayser Simone, Moris Arnaud, Wallwiener Diethelm, Rammensee Hans-Georg, Stevanovic Stefan (2001) A MAGE-A1 HLA-A *0201 Epitope Identified by Mass Spectrometry. Cancer Research 61: 4072.
Peng LS, Penichet ML, Morrison SL (1999) A single-chain IL-12 IgG3 antibody fusion protein retains antibody specificity and IL-12 bioactivity and demonstrates antitumor activity. J Immunol 163: 250.
Penichet ML, Harvill ET, Morrison SL (1997) Antibody-IL-2 fusion proteins: a novel strategy for immune protection. Hum Antibodies 8: 106.
Plaksin Daniel, Polakova Katarina, McPhie Peter, and Margulies David H (1997) A ThreeDomain T Cell Receptor Is Biologically Active and Specifically Stains Cell Surface MHC/Peptide Complexes. The American Association of Immunologists 158: 2218.
Posey JA, Raspet R, Verma U, Deo YM, Keller T, Marshall JL, Hodgson J, Mazumder A, Hawkins MJ (1999) A pilot trial of GM-CSF and MDX-H210 in patients with erbB-2-positive advanced malignancies. J Immunother 22: 371.
Pullarkat V, Deo Y, Link J, Spears L, Marty V, Curnow R, Groshen S, Gee C, Weber JS (1999) a phase I study of a HER2/neu bispecific antibody with granulocyte-colony-stimulating factor in patients with metastatic breast cancer that overexpresses HER2/neu. Cancer Immunol Immunother 48: 9.
Reddy KR, Wright TL, Pockros PJ, Shiffman M, Everson G, Reindollar R, Fried MW, Purdum PP 3rd, Jensen D, Smith C, et al. (2001) Efficacy and safety of pegylated (40-kd) interferon alpha-2a compared with interferon alpha-2a in noncirrhotic patients with chronic hepatitis C. Hepatology 33: 433.
Rosenberg SA, Lotze MT, Muul LM, Chang AE, Avis FP, Leitman S, Linehan WM, Robertson CN, Lee RE, Rubin JT, et al (1987) A progress report on the treatment of 157 patients with advanced cancer using lymphokine-activated killer cells and interleukin-2 or high-dose interleukin-2 alone. N Engl J Med 316: 889.
Rosenberg SA, Lotze MT, Yang JC, Aebersold PM, Linehan WM, Seipp CA, White DE (1989) Experience with the use of high-dose interleukin-2 in the treatment of 652 cancer patients. Ann Surg 210: 474.
Rosenberg SA, Spiess PJ, Schwarz S (1983) In vivo administration of Interleukin-2 enhances specific alloimmune responses. Transplantation 35: 631.
Rosenberg SA, Yang JC, White DE, Steinberg SM (1998) Durability of complete responses in patients with metastatic cancer treated with high-dose interleukin-2: identification of the antigens mediating response. Ann Surg 228: 307.
Royal RE, Steinberg SM, Krouse RS, Heywood G, White DE, Hwu P, Marincola FM, Parkinson DR, Schwartzentruber DJ, Topalian SL, et al. (1996) Correlates of Response to IL-2 Therapy in Patients Treated for Metastatic Renal Cancer and Melanoma. Cancer J Sci Am 2: 91.
Schirle Markus, Keilholz Wieland, Weber Bernd, Gouttefangeas Cécile, Dumrese Tilman, Becker Horst Dieter, Stevanovic Stefan, Rammensee Hans-Georg (2000) Identification of tumor-associated MHC class I ligands by a novel T cell-independent approach. Eur J Immunol 30(8): 2216.
Sherman LA, Hesse SV, Irwin MJ, La Face D, Peterson P (1992) Selecting T cell receptors with high affinity for self-MHC by decreasing the contribution of CD8. Science 258: 815.
Sondel PM, Kohler PC, Hank JA, Moore KH, Rosenthal NS, Sosman JA, Bechhofer R, Storer B (1988) Clinical and immunological effects of recombinant interleukin 2 given by repetitive weekly cycles to patients with cancer. Cancer Res 48: 2561.
Sosman JA, Hank JA, Moore KH, Borchert A, Schell K, Kohler PC, Goldstein D, Bechhofer R, Storer B, Albertini MR, et al. (1991) Prolonged interleukin-2 (IL-2) treatment can augment immune activation without enhancing antitumor activity in renal cell carcinoma. Cancer Invest 9: 35.
Temmim L, Baker H, Sinowatz F (2001) Immunohistochemical detection of p53 protein expression in breast cancer in young Kuwaiti women. Anticancer Res 21: 743.
Theobald M, Biggs J, Dittmer D, Levine AJ, Sherman LA (1995) Targeting p53 as a general tumor antigen. Proc Natl Acad Sci U S A 92: 11993.
Theobald M, Biggs J, Hernandez J, Lustgarten J, Labadie C, Sherman LA (1997) Tolerance to p53 by A2.1-restricted cytotoxic T lymphocytes. J Exp Med 185: 833.
Thor Straten P, Guldberg P, Schrama D, Andersen MA, Moerch U, Seremet T, Siedel C, Reisfeld RA, Becker JC (2001) In situ cytokine therapy: redistribution of clonally expanded T cells. Eur J Immunol 31: 250.
Tsung K, Meko JB, Peplinski GR, Tsung YL, Norton JA (1997) IL-12 induces T helper 1-directed antitumor response. J Immunol 158: 3359.
Van Els Cécile AC M, Herberts Carla A, van der Heeft Ed, Poelen Martien CM, van Gaans-van den Brink Jacqueline AM, van der Kooi Alexander, Hoogerhout Peter, Jan ten Hove G, Meiring Hugo D and de Jong Ad PJ M (2000) A single naturally processed measles virus peptide fully dominates the HLA-A*0201-associated peptide display and is mutated at its anchor position in persistent viral strains. Eur J Immunol 30(4): 1172.
van Golen KL, Risin S, Staroselsky A, Berger D, Tainsky MA, Pathak S, Price JE (1996) Predominance of the metastatic phenotype in hybrids formed by fusion of mouse and human melanoma clones. Clin Exp Metastasis. 14: 95.
Wataya Hiroshi, Kamikawaji Nobuhiro, Nakanishi Yoichi, Takayama Koichi, Hara Nobuyuki, Sasazuki Takehiko (2001) Quantitation of HLA-A *0201 Bound Tumor Associated Antigens on a Peptide Pulsed B Cell Line. Human Immunology 62: 125.
Weber S, Traunecker A, Oliveri F, Gerhard W, Karjalainen K (1992) Specific low-affinity recognition of major histocompatibility complex plus peptide by soluble T-cell receptor. Nature 356: 793.
Webster Dictionary definition for "manipulate", 2009, pp. 1-2.
Weil-Hillman G, Voss SD, Fisch P, Schell K, Hank JA, Sosman JA, Sugamura K, Sondel PM (1990) Natural killer cells activated by interleukin 2 treatment in vivo respond to interleukin 2 primarily through the p75 receptor and maintain the p55 (TAC) negative phenotype. Cancer Res 50: 2683.
Wiebke EA, Rosenberg SA, Lotze MT (1988) Acute immunologic effects of interleukin-2 therapy in cancer patients: decreased delayed type hypersensitivity response and decreased proliferative response to soluble antigens. J Clin Oncol 6: 1440.
Zhu et al., 2006, J. Immunol. vol. 176: 3223-3232.

\* cited by examiner

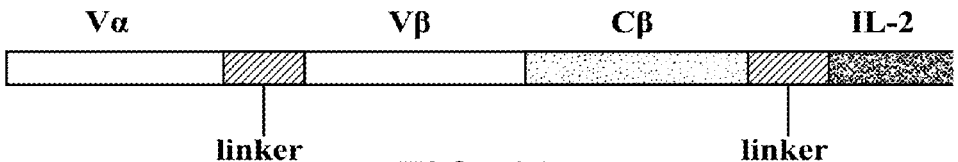

FIG. 1A

Leader 1–20
m e t d t l l l w v l l l w v p g s t g <u>Q S V T Q P D A R V</u>
<u>Vα 21–133</u>
<u>T V S E G A S L Q L R C K Y S Y S G T P Y L F W Y V Q Y P R</u>

<u>Q G L Q L L L K Y Y S G D P V V Q G V N G F E A E F S K S N</u>

<u>S S F H L R K A S V H W S D S A V Y F C V L S E D S N Y Q L</u>
(G₄S₄) linker 134–157
<u>I W G S G T K L I I K P D</u> *T S G G G G S G G G G S G G G G S*

*G G G G S S* <u>S N S K V I Q T P R Y L V K G Q G Q K A K M R C</u>
Vβ 158–271
<u>I P E K G H P V V F W Y Q Q N K N N E F K F L I N F Q N Q E</u>

<u>V L Q Q I D M T E K R F S A E C P S N S P C S L E I Q S S E</u>

<u>A G D S A L Y L C A S S L S G G G T E V F F G K G T R L T V</u>
Cβ 272–397
*V E D L R N V T P P K V S L F E P S K A E I A N K Q K A T L*

*V C L A R G F F P D H V E L S W W V N G K E V H S G V S T D*

*P Q A Y K E S N Y S Y C L S S R L R V S A T F W H N P R N H*

*F R C Q V Q F H G L S E E D K W P E G S P K P V T Q N I S A*
Linker 398–414
*E A W G R A D V N A K T* *T A P S V Y P L A P V S G A P T S S*

S T K K T Q K G L E H L L L D L Q M I L N G I N N Y K N P K
IL-2 415–548
L T R M L T F K F Y M P K K A T E L K H L Q C L E E E L K P

L E E V L N L A Q S K N F H L R P R D L I S N I N V I V L E

L K G S E T T F M C E Y A D E T A T I V E F L N R W I T F C
EE tag 549–559
Q S I I S T L T *S R E E E E Y M P M E* * *

FIG. 1B

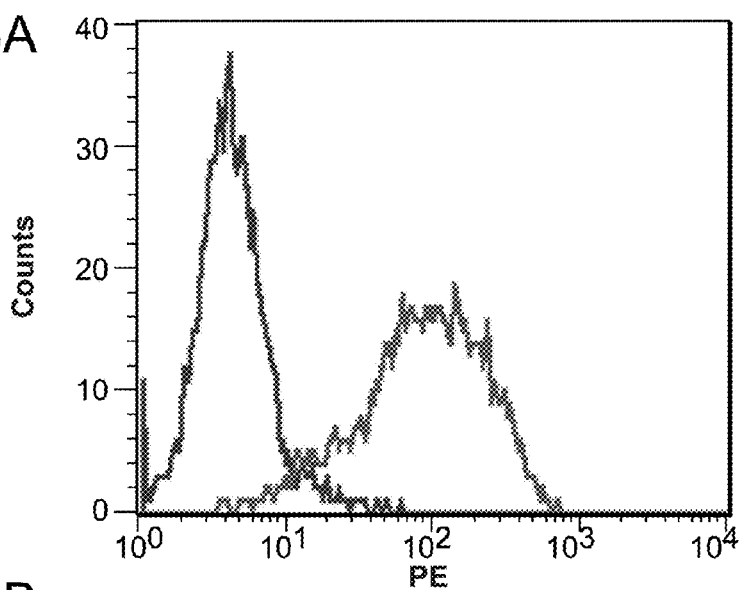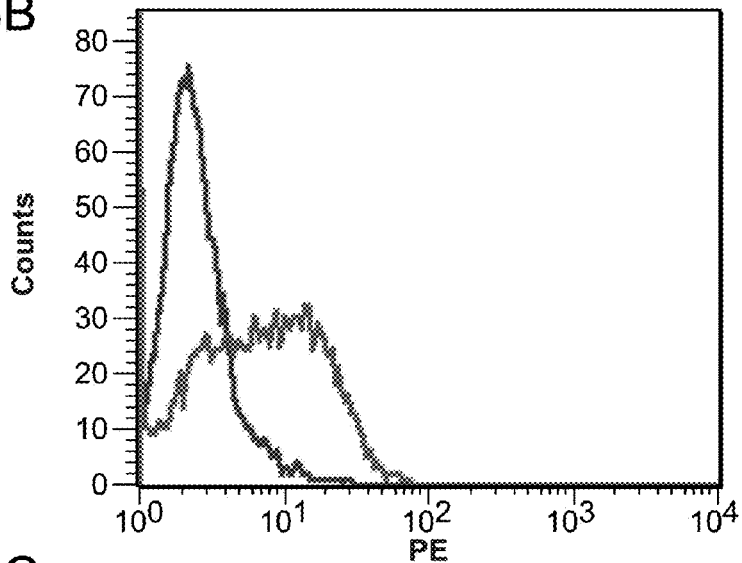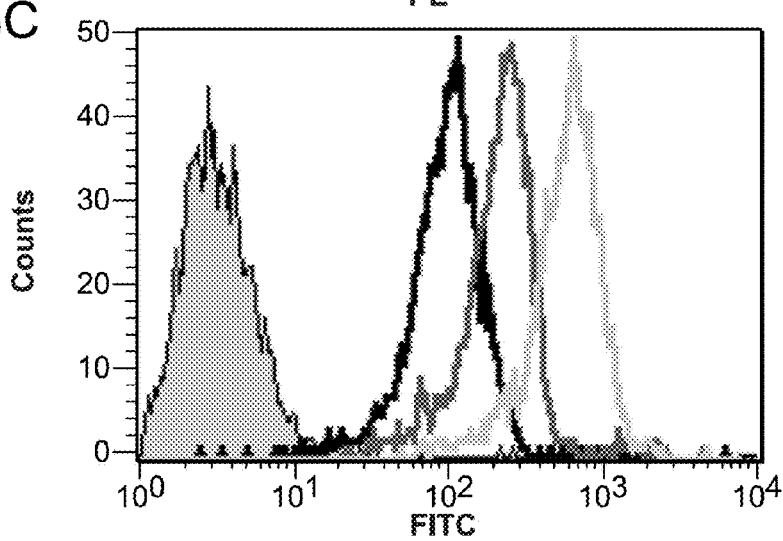

T2 cells loaded with nonspecific peptide

| Key | Name | Parameter | Gate |
|---|---|---|---|
| —— | T2 149 unstained.001 | FL2-H | G14 |
| —— | T2 149 H57.002 | FL2-H | G14 |
| —— | T2 149 IgG H57.003 | FL2-H | G14 |
| —— | T2 149 IL2 H57.004 | FL2-H | G14 |
| —— | T2 149 trun H57.005 | FL2-H | G14 |
| —— | T2 149 birA H57.006 | FL2-H | G14 |

T2 cells loaded with specific peptide

| Key | Name | Parameter | Gate |
|---|---|---|---|
| ▬ | T2 149 unstained.001 | FL2-H | G14 |
| ─ | T2 264 H57.009 | FL2-H | G14 |
| ▬ | T2 264 IgG H57.010 | FL2-H | G14 |
| ─ | T2 264 IL2 H57.011 | FL2-H | G14 |
| ─ | T2 264 trun H57.012 | FL2-H | G14 |
| ─ | T2 264 birA H57.013 | FL2-H | G14 |

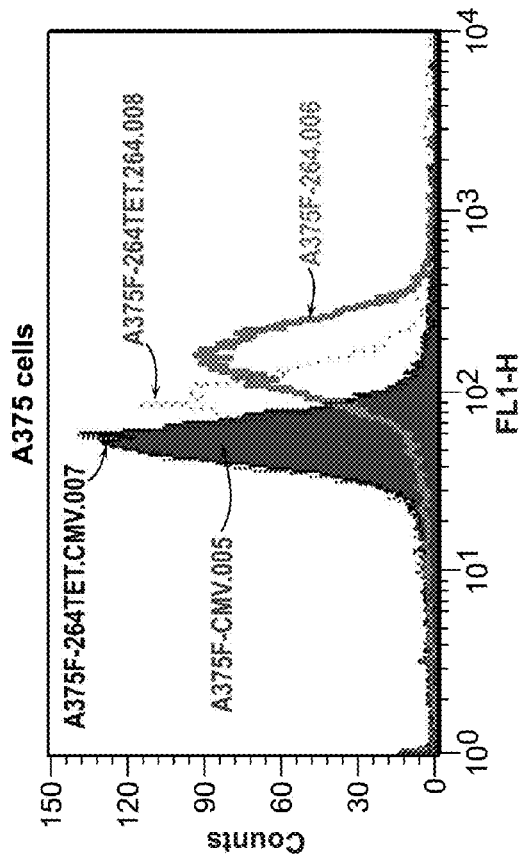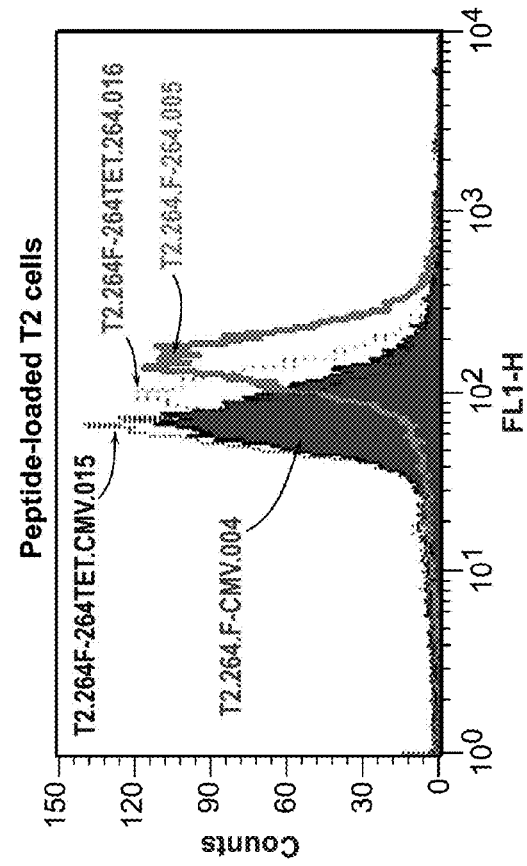

SOLUBLE TCR MOLECULES AND METHODS OF USE

CROSS REFERENCE TO RELATED APPLICATIONS

This application is a continuation of U.S. application Ser. No. 10/985,271 filed Nov. 10, 2004 which claims the benefit of U.S. provisional application Ser. No. 60/518,790 filed Nov. 10, 2003, the entire contents of which are expressly incorporated herein by reference.

STATEMENT OF U.S. GOVERNMENT INTEREST

Funding for the present invention was provided in part by the Government of the United States by virtue of Grant Nos.: 1R43CA88615-01 and 1R43CA105816-01 from the National Institutes of Health. Accordingly, the Government of the United States has certain rights in and to the invention claimed herein.

FIELD OF THE INVENTION

The invention features compositions and methods for detecting cells or tissue comprising a peptide antigen presented in the context of an MHC or HLA complex. The invention has a wide range of applications including providing a highly sensitive method for detecting cancer cells.

BACKGROUND

There is increasing recognition that immunotherapy is a promising approach to treat cancer. Various strategies have been proposed including treatment with cytokines such as interleukin-2 (IL-2). IL-2 impacts various immune cell types including T and B cells, monocytes, macrophages, lymphokine activated killer cells (LAK) and NK cells [10, 40].

There have been proposals to concentrate cytokines at the site of tumors to help increase efficacy. Typical methods include direct injection of the cytokine or gene encoding same into the tumor, or targeted delivery of the cytokine by fusing it to a tumor antigen specific antibody [20]. However, these methods have drawbacks.

For example, most direct injection methods are difficult to use especially at early stages of cancer when tumors are typically small (micrometastases). Moreover, such methods are usually labor-intensive with little guarantee of therapeutic success. This makes treatment of large patient populations impractical and costly.

Antibody-cytokine fusion constructs have been used in an approach to treat cancer. However, the methods are limited to the extent that the antibody has a limited binding spectrum. That is, the antibodies can only recognize certain cell surface antigens. Unfortunately, many tumor antigens are not displayed appropriately for antibody recognition, thereby limiting potential of antibody based approaches. Moreover, there are reports that many tumor specific antigens are derived from aberrant expression of cell type specific proteins. These may exist only with a small number of tumor types. This drawback limits the potential of antibody based therapies even further.

The p53 protein is an intracellular tumor suppressor that has been reported to act by arresting abnormal cells at the G1/S phase of the cell cycle. Over expression of the protein is believed to be a significant tumor marker for a large number of human malignancies and there is recognition that it is a good target for broad spectrum targeted tumor immunotherapy. The p53 protein is usually displayed on the cell surface in the context of major histocompatibility complex proteins (MHC). Such protein complexes are known to be the binding targets of T-cell receptors (TCRs). [49].

There have been attempts to use certain TCRs to detect MHC/peptide complexes containing peptide (Epel et al., 2002; Holler et al., 2003; Lebowitz et al., 1999; Plaksin et al., 1997; Wataya et al., 2001; O'Herron et al., 1997). However, these and related methods have significant shortcomings.

For instance, many of the methods require that TCR constructs be multimerized (i.e., designed to have multiple TCR copies) presumably to enhance peptide antigen binding with peptide antigen artificially. Target (antigen presenting) cells are often manipulated by the methods to express relatively large amounts of peptide antigen. Sometimes the density of peptide antigen is as high as $10^4$ to $10^5$ complexes per cell (Wataya et al., 2001). Such a high peptide antigen density is believed to facilitate binding and detection by the TCRs. However, these levels of peptide antigen are artificial and typically much greater than the level of MHC/peptide complexes that include most tumor-associated antigens (TAAs). For some TAAs, less than about 50 HLA/peptide complexes per cell are present (Pascolo et al., 2001; Schirle et al., 2000). Thus, there has been recognition that the prior methods are not sensitive enough to detect most if not all TAAs.

There have been attempts to use certain TCRs to detect cells expressing particular peptide antigens. Like many antibody based methods, these approaches have either lacked enough sensitivity to detect peptide antigen or failed to detect such antigen completely.

For example, Holler et al. (2003) reported the development of certain soluble TCRs that were reported to react with MHC/peptide complexes. Although the TCRs were able to detect antigen with cells artificially "loaded" with the antigen, the molecules were unable to detect endogenous antigen on tumor cells. Holler et al. concluded that when the antigen is present at a density of less than 600 copies per cell, TCR based methods are not sensitive or reliable enough to detect antigen.

Particular TCR based methods have been used to detect viral peptides in the context of MHC molecules. (Strominger, et al., WO9618105). However, these and related methods suffer from drawbacks. For instance, there is general recognition that viral infection often produces exceptionally high densities of MHC/peptide complexes, typically approaching from >1000 to >$10^5$ complexes per cell. See Herberts et al., 2001; van Els et al., 2000. Thus like most other peptide antigen detection methods, TCR based approaches to detect viral antigens have so far relied on the relatively large number of antigen targets to drive the detection method.

Although some TCR based methods have been used to detect relatively large amounts of peptide antigen, it is less certain if the methods will work when the TCR is fused to other molecules such as a cytokine, an immunoglobin domain such as IgG1, biotin or streptavidin. That is, it is not certain how the resulting fusion molecule will impact the TCR peptide binding groove particularly when low densities of TAA need to be analyzed. Small distortions in the TCR peptide binding groove, while not necessarily problematic when relatively large amounts of peptide antigen are to be analyzed, could reduce TAA binding specificity and selectivity. Even small changes in the TCR peptide binding groove function could jeopardize detection of cancer cells that express low TAA densities.

It would be useful to have methods for detecting TAAs that are sensitive, selective and reproducible especially when the peptide antigens are present in low densities. It would be especially useful if such methods could be used with a variety of soluble TCRs including molecules such as those fused to a detectable label or a cytokine.

SUMMARY OF THE INVENTION

The invention generally features a method for detecting cells or tissue comprising a peptide antigen presented on the cells or tissue in the context of an MHC or HLA complex. In one embodiment, the invention includes at least one and preferably all of the following steps:
  a) contacting the cells or tissue with at least one soluble TCR molecule or functional fragment thereof under conditions that form a specific binding complex between the presented peptide antigen and the soluble TCR or fragment,
  b) washing the cells or tissue under conditions appropriate to remove any soluble TCR molecule or fragment not bound to the presented peptide antigen; and
  c) detecting the specific binding complex as being indicative of cells or tissue comprising the presented peptide antigen.

In preferred practice, the invention is used to detect an amount of peptide antigen on the cells or tissue that is less than about 100,000 copies, preferably less than about 1000 copies such as about 100 to about 800 copies.

Use of the invention has several advantages. For instance, the invention is highly sensitive and can be used to detect and optionally quantitate very low-density MHC/peptide complexes including those containing endogenous peptide, more particularly tumor-associated peptide antigens presented on unmanipulated tumor cells. In contrast, prior methods for detecting MHC/peptide complexes are reported to be capable of detecting relatively higher density complexes.

Additionally, the invention can be used to detect and optionally quantitate fixed cells and tissues such as those routinely found in histoarrays, for example tumor histoarrays. The ability to detect MHC/peptide complexes (sometimes called "staining") is advantageous, especially in clinical or other medical settings where it is typical practice to fix cells, tissues or other biological samples taken from patients. In contrast, many prior TCR-based detection methods are not able to accommodate fixed tissue since noncovalently associated peptide is routinely lost during the tissue processing steps.

The invention provides still further advantages. For instance, the methods are intended to be flexible and compatible with use of monomeric and/or multimeric soluble TCR molecules. Unfortunately, past practice has relied heavily on use of multimeric TCRs which has limited flexibility and sensitivity. In particular, such multimeric TCRs may be difficult to use for in vivo imaging due to their potential for breakdown or aggregation, lack of accessibility to the target site, increased immunogenicity and clearance.

Practice of the invention addresses a long-felt need in the field by providing an ability to detect endogenous peptide antigen presented in the context of the MHC/peptide complex on the surface of cells. The method has a variety of important uses such as helping to monitor cell activity, pathology and infection. For example, detection of endogenous tumor-associated peptide antigens on cells or tissues by the invention can provide a means of detecting and optionally quantitating the presence/extent of a cancer. Past practice has often relied on antibodies as a diagnostic tool to detect protein antigens on the surface of cancer cells. However, antibodies typically are limited in detection of cell-membrane proteins. In addition, detection with antibodies is often compromised by antigen shedding or secretion of the antigenic protein into the circulation. Antibodies also have limited target recognition. Practice of the invention avoids these and other difficulties by providing a sensitive and reliable detection method that uses soluble TCRs and fragments thereof to detect target peptide antigens.

Such uses and advantages of the invention can be employed to detect peptide antigen in a variety of settings including in vivo (e.g., as an imaging or diagnostic method) or in vitro (e.g., in a histoarray or FACS analysis).

Other aspects of the invention are discussed infra.

BRIEF DESCRIPTION OF THE DRAWINGS

FIGS. 1A-B are drawings showing the schematic structure (FIG. 1A) and the amino acid sequence (FIG. 1B) of a 264scTCR/IL-2 fusion protein (SEQ ID NO: 16). $(G_4S)_4$ linker disclosed as SEQ ID NO: 17.

FIG. 3A, FIG. 3B, and FIG. 3C are graphs showing MHC/peptide binding ability of the TCR portion of 264scTCR/IL-2 fusion protein.

FIG. 12A and FIG. 12B are graphs showing staining of fixed A375 (FIG. 12A) or T2 cells (FIG. 12B) with 264scTCR/IgG1 and CMVscTCR/IgG1 (control) reagents, with and without the addition of competing soluble peptide-MHC molecules (labeled 264-Tet).

DETAILED DESCRIPTION

Figure 2:
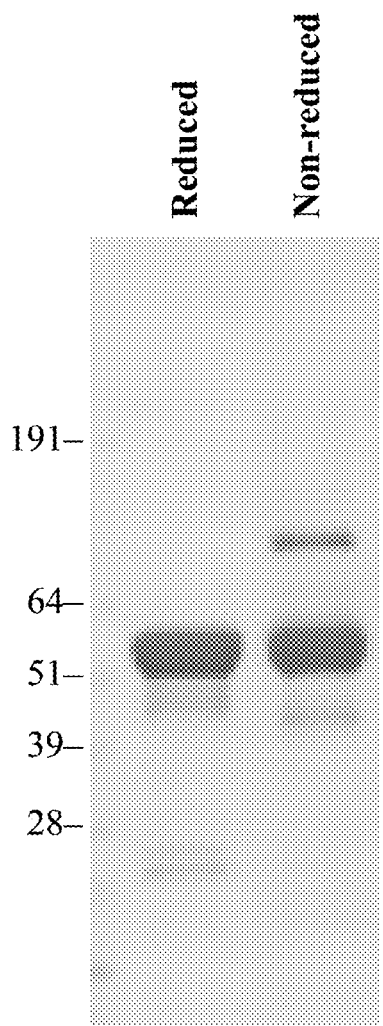
FIG. 2 is a representation of a sizing gel showing production of 264scTCR/IL-2 fusion protein in transfected CHO cells.

As discussed, the invention generally involves a method for detecting cells or tissue comprising a peptide antigen presented on the cells or tissue in the context of an MHC complex. In one embodiment, the invention includes contacting the cells or tissue with at least one soluble TCR molecule or functional fragment thereof under conditions that form a specific binding complex between the presented peptide antigen and the soluble TCR or fragment; washing the cells or tissue under conditions appropriate to remove any soluble TCR molecule or fragment not bound to the presented peptide antigen; and detecting the specific binding complex as being indicative of cells or tissue comprising the presented peptide antigen.

In general, preparation of the present soluble TCRs can be accomplished by procedures disclosed herein and by recognized recombinant DNA techniques. For example, preparation of plasmid DNA, DNA cleavage with restriction enzymes, ligation of DNA, introduction of DNA into a cell, culturing the cell, and isolation and purification of the expressed protein are known techniques. See generally Sambrook et al. in *Molecular Cloning: A Laboratory Manual* (2d ed. 1989); and Ausubel et al. (1989), *Current Protocols in Molecular Biology*, John Wiley & Sons, New York.

The general structure of a variety of soluble TCR constructs and methods of making and using same have been disclosed in pending U.S. application Ser. Nos. 08/813,781 and 08/943,086.

For instance, a particular soluble TCR is a heterodimer in which transmembrane sequence in at least one of and preferably both of the V chains has been deleted. However for convenience, it will often be preferred to use single-chain ("sc-") constructs such as those reported by the pending Ser. No. 08/813,781 and Ser. No. 08/943,086 applications.

Briefly stated, a single-chain ("sc-") TCR molecule includes V-α and V-β chains covalently linked through a suitable peptide linker sequence. For example, the V-α chain can be covalently linked to the V-β chain through a suitable peptide linker sequence fused to the C-terminus of the V-α chain and the N-terminus of the V-β chain. The V-α and V-β chains of the sc-TCR fusion protein are generally about 200 to 400 amino acids in length, preferably about 300 to 350 amino acids in length, and will be at least 90% identical, and preferably 100% identical to the V-α and V-β chains of a naturally-occurring TCR. By the term "identical" is meant that the amino acids of the V-α or V-β chain are 100% homologous to the corresponding naturally-occurring TCR V-β or V-α chains.

As disclosed in the Ser. No. 08/943,086 application, the V-α chain of the sc-TCR molecule can further include a C-β chain or fragment thereof fused to the C-terminus of the V-β chain. Further, the V-α chain can include a C-α chain or fragment thereof fused to the C-terminus of the V-α chain and the N-terminus of the peptide linker sequence. Generally, in those fusion proteins including a C-β chain fragment, the fragment will have a length of approximately 50 to 130 amino acids and will usually not include the last cysteine residue (at position 127 in the mouse or at position 131 in the human) of the C-β chain. For those fusion proteins comprising a C-α chain, the length can vary between approximately 1 to 90 amino acids (i.e. the C-α chain up to but not including the final cysteine). For example, in one embodiment, the fusion protein includes a C-α chain fragment between about 1 to 72 amino acids starting from amino acid 1 to 72. In another embodiment, the C-α chain fragment is between about 1 to 22 amino acids starting from the first amino acid to 22 (leucine). The C-α chain fragment typically does not include any cysteine resides except the $C_{\infty 90}$ variant which includes two cys residues and the $C_{\infty 72}$ variant which includes one cys residue. In most cases, choice of Cα and Cβ chain length will be guided by several parameters including the particular V chains selected and intended use of the soluble fusion molecule.

As further disclosed by the Ser. No. 08/943,086 application, additional sc-TCR proteins of the invention include e.g., two peptide linker sequences, where the first peptide linker sequence is fused between the C-terminus of the V-α chain and the N-terminus of the V-β chain. The C-terminus of the V-β chain can be fused to the N-terminus of a C-β chain fragment. The second peptide linker is then fused to the C-terminus of the V-β chain or C-β chain fragment or, if desired, to a tag molecule as explained below. In other illustrative embodiments, sc-TCR proteins can be made by fusing the V-β chain to the V-α chain through a suitable peptide linker in which the C-terminus of the V-β chain or C-β chain fragment thereof and the N-terminus of the V-α chain are covalently linked.

A soluble TCR protein according to the invention can include one or more fused protein tags. In embodiments in which such tags are "detectable", the soluble TCR will be referred to as being "detectably labeled". For example, with respect to a soluble fusion protein, a protein tag can be fused to the C-terminus of the sc-TCR V-β chain (or C-β chain fragment). If desired, such soluble TCR proteins can be fused to immunoglobin chains as has been reported by the pending Ser. No. 08/943,086 application, and further illustrated in Examples below.

Preferred soluble fusion proteins for use with the invention are fully functional and soluble. By the term "fully functional" or similar term is meant that the fusion protein specifically binds ligand. Assays for detecting such specific binding are disclosed herein and include standard immunoblot techniques such as Western blotting. Functional fragments of such soluble TCRs are able to bind antigen with at least 70% of the affinity of the corresponding full-length TCR, preferably about 80% to 90% or more as determined by Western blot or Surface Plasma Resonance analysis.

The nucleic acid and protein sequences of suitable TCR chains have been disclosed. See e.g., *Fundamental Immunology*, (1993) $3^{rd}$ Edi. W. Paul. Ed. Rsen Press Ltd. New York; and Kabat, E. A., et al., (1991) *Sequences of Proteins of Immunological Interest* ($5^{th}$ Ed.) Public Health Services, National Institutes of Health. See also the pending Ser. No. 08/813,781 and Ser. No. 08/943,086 applications as well as the Examples that follow.

In a particular embodiment of the invention, the method further includes contacting the cells or tissue with at least one blocking agent. The contacting step can be performed at any point in the method including before, during or after step a) to reduce non-specific binding between the soluble TCR or fragment and the cells. The invention is compatible with use of nearly any standard blocking agent such as peroxide, serum protein, antibody or an antigen-binding fragment thereof.

In certain embodiments, it will often be useful to confirm the binding specificity of the TCR to the MHC complex on the cells or tissues to be detected. In such instances, the invention can further include contacting the specific complex (formed between the soluble TCR and the MHC complex residing on the cells or tissue) with a competing MHC (or HLA) molecule or fragment thereof under conditions that compete with and specifically bind the soluble TCR or fragment bound to the complex. A variety of suitable MHC molecules have been disclosed.

In one embodiment of the method, specific binding of the soluble TCR or fragment is reduced or essentially eliminated by the addition of a competing MHC molecule or fragment thereof, such that the soluble TCR or fragment is bound to the competing MHC molecule or fragment thereof to form a competition complex. In one particular embodiment of the method, the competing MHC molecule is added at a range of concentrations between a 0.01 to 1000 fold, or preferably a 1 to 100 fold, molar excess over the soluble TCR. In another embodiment, the competing MHC molecule is added at a single concentration (i.e. 1-fold, 10 fold, or 100-fold molar excess over the soluble TCR) sufficient to reduce specific binding of the soluble TCR. If desired, that competition complex can be detected and binding specificity of the MHC molecule or the soluble TCR determined by one or a combination of conventional strategies. Particular MHC molecules or fragments can be single-chain but in most instances will be soluble heterodimeric molecules such as those disclosed in U.S. Pat. Nos. 5,869,270; 6,309,645; and pending application Ser. No. 09/848,164. See also PCT application PCT/US95/09816 for additional disclosure, as well as the Examples provided below. Typical MHC molecules or fragments will be loaded with peptide antigen.

See also the following published U.S. patent applications for disclosure relating to other soluble TCR and MHC molecules that can be used to practice the invention: 20020198144; 20020091079; 20020034513; 20030171552; 20030144474; 20030082719; and references cited therein.

In a typical method in which confirmation of binding specificity is desired, the TCR molecule or fragment is detectably-labeled with one or more tags. Suitable tags include EE or myc epitopes which are specifically bound by commercially available monoclonal antibodies. In general, a wide variety of epitopes capable of being specifically bound by an antibody, e.g., a monoclonal antibody, are capable of serving as a protein tag. Other suitable synthetic matrices include those with a bound antibody capable of specifically binding the molecules. Further tags include those with an enterokinase, Factor Xa, snake venom or thrombin cleavage site. See e.g., published PCT application WO 96/13593.

Other suitable tags for detectably-labeling the TCR molecules or fragments include biotin, streptavidin, a cell toxin of, e.g., plant or bacterial origin such as, e.g., diphtheria toxin (DT), shiga toxin, abrin, cholera toxin, ricin, saporin, pseudomonas exotoxin (PE), pokeweed antiviral protein, or gelonin Biologically active fragments of such toxins are well known in the art and include, e.g., DT A chain and ricin A chain. Additionally, the toxin can be an agent active at the cell surface such as, e.g., phospholipase enzymes (e.g., phospholipase C). See e.g., Moskaug, et al. *J. Biol. Chem.* 264, 15709 (1989); Pastan, I. et al. *Cell* 47, 641, 1986; Pastan et al., *Recombinant Toxins as Novel Therapeutic Agents, Ann. Rev. Biochem.* 61, 331, (1992); "*Chimeric Toxins*" Olsnes and Phil, Pharmac. Ther., 25, 355 (1982); published PCT application no. WO 94/29350; published PCT application no. WO 94/04689; and U.S. Pat. No. 5,620,939 for disclosure relating to making and using proteins comprising effectors or tags. An example of a tag that performs a biotin acceptor function is a BirA tag, as described in Beckett, D. et al. Protein Sci. 1999 April; 8(4):921-9. As further described in Examples below, a BirA tag sequence can be included in a TCR molecule to promote biotinylation of the protein. Further, a tag can be a chemotherapeutic drug such as, e.g., vindesine, vincristine, vinblastin, methotrexate, adriamycin, bleomycin, or cisplatin.

Additionally, a tag can be a radionuclide or chelate, suitable for diagnostic or imaging studies such as iodine-131, yttrium-90, rhenium-188, iodine-123, indium-111, technetium-99m, gallium-67, thallium-201, or bismuth-212. Among the radionuclides used, gamma-emitters, positron-emitters, x-ray emitters and fluorescence-emitters are suitable for localization, while beta-emitters and alpha-emitters may also be used. Other suitable radioisotopes for the methods of the present invention include but are not limited to, cadmiun-109, actinium-225, actinium-227, astatine-211, iodine-125, iodine-126, iodine-133, dysprosium-165, dysprosium-166, bismuth-212, bismuth-213, bromine-77, indium-113m, gallium-67, gallium-68, ruthenium-95, ruthenium-97, ruthenium-101, ruthenium-103, ruthenium-105, mercury-107, mercury-203, rhenium-186, rhenium-188, tellurium-99m, tellurium-121m, tellurium-122m, tellurium-125m, thulium-165, thulium-167, thulium-168, fluorine-18, silver-111, platinum-197, palladium-109, copper-67, phosphorus-32, phosphorus-33, yttrium-90, scandium-47, samarium-153, lutetium-177, rhodium-105, praseodymium-142, praseodymium-143, promethium-149, terbium-161, holmium-166, gold-198, gold-199, cobalt-57, cobalt-58, chromium-51, iron-59, selenium-75, and ytterbium-169. Preferably the radioisotope will emit in the 10-5,000 key range, more preferably 50-1,500 key, most preferably 50-500 key.

Suitable positron emitters and other useful radionuclides include, but are not limited to, $^{11}$C, $^{13}$N, $^{15}$O, $^{18}$F, $^{51}$Mn, $^{52}$Fe, $^{55}$Co, $^{60}$Cu, $^{61}$Cu, $^{62}$Cu, $^{64}$Cu, $^{62}$Zn, $^{63}$Zn, $^{70}$As, $^{71}$As, $^{72}$As, $^{76}$Br, $^{82}$Rb, $^{86}$Y, $^{89}$Zr, $^{94}$mTc, $^{110}$In, $^{120}$I, $^{124}$I, $^{122}$Xe, $^{128}$Ba, $^{131}$Ba, $^{7}$Be, $^{204}$Bi, $^{205}$Bi, $^{206}$Bi, $^{14}$C, $^{36}$Cl, $^{48}$Cr, $^{51}$Cr, $^{155}$Eu, $^{153}$Gd, $^{66}$Ga, $^{72}$Ga, $^{3}$H, $^{115m}$In, $^{189}$Ir, $^{191m}$Ir, $^{192}$Ir, $^{194}$Ir, $^{55}$Fe, $^{59}$Fe, $^{199m}$Os, $^{42}$K, $^{226}$Ra, $^{186}$Re, $^{188}$Re, $^{82m}$Rb, $^{46}$Sc, $^{47}$Sc, $^{72}$Se, $^{105}$Ag, $^{22}$Na, $^{24}$Na, $^{89}$Sr, $^{35}$S, $^{38}$S, $^{177}$Ta, $^{96}$Tc, $^{20}$Tl, $^{202}$Tl, $^{113}$Sn, $^{117}$mSn, $^{121}$Sn, $^{166}$Yb, $^{174}$Yb, $^{88}$Y, $^{90}$Y, $^{62}$Zn and $^{65}$Zn.

Suitable chelates include, but are not limited to, diethylenetriamine pentaacetic acid (DTPA), 1,4,7,10-tetraazacyclotetradecane-1,4,7,10-tetraacetic acid (DOTA), 1-substituted 1,4,7,-tricarboxymethyl 1,4,7,10 teraazacyclododecane triacetic acid (DO3A), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phen-ylglycine) (EHPG), and derivatives thereof, including 5-Cl-EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl) aminomethylbenzene (MECAM).

Other suitable tags include polyhistidine, fluorescent label, chemiluminescent label, nuclear magnetic resonance active label, chromophore label, positron emitting isotope detectable by a positron emission tomography ("PET") scanner, enzymatic markers such as beta-galactosidase and peroxidase including horse radish peroxidase, a nanoparticle, a paramagnetic metal ion, a contrast agent or an antigenic tag.

A suitable fluorescent label could include, but is not limited to, a $^{152}$Eu label, a fluorescein label, an isothiocyanate label, a rhodamine label, a phycoerythrin label, a phycocyanin label, an allophycocyanin label, an o-phthaldehyde label, a Texas Red label, a fluorescamine label, a lanthanide phosphor label, a fluorescent protein label, for example a green fluorescent protein (GFP) label, or a quantum dot label. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Suitable paramagnetic metal ions include, but are not limited to, $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$, and $Eu^{2+}$.

Enzyme markers that may be used include any readily detectable enzyme activity or enzyme substrate. Such enzymes include malate dehydrogenase, staphylococcal nuclease, delta-5-steroid isomerase, alcohol dehydrogenase, aglycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, luciferase, and DNA polymerase.

Suitable nanoparticles include, but are not limited to, solid colloidal particles, dendrimers, liposomes, micelles, ceramic particles, alumina capsules, emulsifying wax or Brij 72 particles, ferromagnetic particles, gold or silver particles, biodegradable particles comprising poly(lactic-co-glycolic) acid, polyglycolic acid, poly D- or L-lactic acid, polycaprolactone or serum albumin and particles comprising poly(vinyl pyrrolidone), polystyrene, polyacrylamide, or poly(butyl cyanoacrylate) or derivative thereof. In some applications of the invention, nanoparticles coated with agents such a polyethylene glycol, polysaccharide, polypeptides, lipids, silica, etc. can be used. Such coated nanoparticles may have improved absorbance, bioavailability, tissue distribution, tissue cross-reactivity, toxicity, pharmacokinetics/dynamics, or tumor localization. Methods for attaching targeting ligands to nanoparticles have been described that can be applied to soluble TCR-based reagents (see, for example, Nob et al. 2004. J Pharm Sci. 93:1980-92).

The soluble TCRs of the invention include monomeric and multimeric TCRs. Multimeric TCR molecules include those in which the TCR protein is fused to polypeptide domains or tags that facilitate multimerization. Such domains include immunoglobin, leucine zipper, helix-turn-helix, and barrel-barrel motifs that facilitate protein dimerization. Such tags include antibody-binding epitopes, streptavidin-binding peptides, 6×His motif, biotin ligase target motif, and the like. Multimeric TCR molecules also include those generated through chemically crosslinking reactive amino acids or polysaccharides. Such amino acids (or polysaccharides) can be inherent in the TCR structure or can be added through genetic modification. Multimeric TCRs also include those generated through attachment to another molecule (or molecules) that may or may not include a detectable label as described herein. Such attachment molecules include streptavidin, biotin, antibodies, protein A or scaffolds that include protein-, lipid- and polysaccharide-coated or uncoated beads, nanoparticles, solid-phase surfaces, arrays, matrices, as described. For example, in various embodiments in which the detectable label is biotin, the method further comprises combining the TCR molecule with streptavidin to multimerize the TCR molecule.

It will be appreciated that any one of the tags disclosed herein can be used to detectably label the soluble TCRs used in the invention method, particularly to detect the cells or tissue expressing the peptide antigen of interest.

It is an object of the invention to provide peptide antigen detection methods that perform using cells or tissue contacted with a denaturing agent sufficient to "fix" the cells or tissue. Examples of such agents are known in the field and include formaldehyde (formalin), glutaraldehyde, alcohols such as methanol, proponal, etc, and organic solvents such as benzene and xylene. As has been discussed, it has been found that the invention methods do not substantially disturb interaction between the MHC molecule on the cells and its cognate peptide antigen even when the cells or tissue are fixed. Thus, the invention can be used on fixed cells or tissue, thereby helping to preserve structural integrity and enhancing reliability of the method.

Accordingly, and in one embodiment, the invention further comprises contacting the cells or tissue with at least one denaturing agent. Such contact can be performed at nearly any time including before step a) and denaturing (fixing) the cells or tissue.

As also discussed, the invention is compatible with use of cells or tissue in an array such as what is referred to in the field as a histoarray. That is, the invention has the sensitivity and reliability needed to screen cell or tissue samples (such as those encountered in a clinic) in a repetitive fashion. Many such arrays are known in the field such as those described by U.S. Pat. Nos. 6,466,690; 4,384,193; 6,602,661; 6,594,432; 6,566,063; 6,406,840; 6,246,785; and references cited therein.

Accordingly, and in one embodiment, the method of the present invention further includes placing a plurality of cells or tissue in an array. Preferably, such cells or tissues are known or suspected of including (or consisting of) tumor cells. The method can be performed in each element of the array comprising cells or tissue. If desired, the method is performed substantially simultaneously in each element of the array. In one embodiment, the step c) of the method further includes scanning the array and generating image signals indicative of presence of the specific binding complex. If needed, that step can further include outputting the signals in real-time to a user and optionally indexing stored images of the image signal.

The invention can be used to detect a wide variety of peptide antigens including those referred to as tumor-associated peptide antigens or TAAs. Cells or tissues may be suspended, semi-suspended, or fixed according to the method.

As discussed, the soluble TCR molecule or fragment can include at least one single-chain TCR or it may be a heterodimeric construct such as those that have been manipulated recombinantly to remove transmembrane domains. See the pending Ser. No. 08/813,781 and Ser. No. 08/943,086 applications as well as the Examples that follow. Such soluble TCR molecules or fragments can be detectably labeled by one or a combination of strategies as outlined herein including labeling with biotin, streptavidin, an enzyme or catalytically active fragment thereof, radionuclide, or a fluorescent, phosphorescent, or chemiluminescent molecule. Examples include the well-known green (or red) fluorescent protein or fragments thereof.

In certain embodiments, the soluble TCR is a single-chain TCR which molecule is covalently bound to at least one cytokine. Examples of such cytokines include, but are not limited to, IL-2, colony stimulating factors such as GM-CSF, IFNγ, IFN-α and the like. As an example, the soluble TCR molecule or fragment is a single-chain TCR that includes at least one and preferably one covalently bound cytokine or fragment thereof.

In certain other variations, the soluble TCR is a single chain TCR or fragment that includes at least one covalently bound immunoglobulin domain or fragment thereof. In some embodiments the single chain TCR or fragment is fused to sequence comprising an IgG1 domain or fragment.

In yet another embodiment, the MHC complex is HLA-A2 restricted.

It will often be useful to include a control with the method, for example, by detecting any binding between the soluble TCR or fragment to cells that do not comprise the peptide antigen.

A particular peptide antigen for use with the invention includes p53 (aa 149-157) or p53 (aa 264-272).

The present invention methods can be performed in vivo, ex vivo, or in vitro.

For instance, HLA typing (see, e.g., A. K. Abbas, Cellular and Molecular Immunology, page 328 (W.B. Saunders Co. 1991) can be practiced with the invention. For in vivo imaging applications, the soluble TCR will desirably include a radionuclide (e.g., 125I, 32P, 99Tc) or other detectable tag which can be administered to a mammal and the subject scanned by known procedures for binding of the TCR or fragment thereof. Such an analysis of the mammal could aid in the diagnosis and treatment of a number of disorders including e.g. undesired expression of APCs accompanying immune system disorders and cancer.

The invention can also be used for in vivo imaging of tumors bearing tumor-associated peptide antigens in a subject having or suspected of having such a tumor. In the practice of this method, a composition is administered to the subject that comprises a detectably labeled soluble TCR molecule or fragment thereof that specifically binds the tumor-associated peptide antigen in the context of a peptide/MHC complex on the tumor. The composition is administered in vivo for a period of time sufficient to permit its accumulation at the tumor site. The accumulated composition is then detected so as to image the tumor.

The composition comprising the TCR can be administered parenterally (such as intravenously, intramuscularly, subcutaneously, intratumorally, etc.) at a locus and/or by a route providing access to the tissue, organ or cells of interest. In other applications, the composition comprising the TCR can be administered intranasally, orally or transdermally.

The accumulated composition of the soluble TCR can be detected by a variety of means. These include detection by a detector selected from the group consisting of a conventional scintillation camera, a gamma camera, a rectilinear scanner, a PET scanner, a SPECT scanner, a MRI scanner, a NMR scanner, an ultrasound machine, an X-ray machine, a luminescence imaging system, and a fluorescence imaging system.

The imaging methods of the present invention further encompass pretargeting methods which in some applications may improve the detection of a tumor cell or tissue. This approach uses a multi-step protocol. For example, a targeting TCR is conjugated with either avidin or biotin and then is administered, for example by injection, whereupon it localizes in the tumor of interest. Thereafter, either biotin or avidin (depending on which was coupled to the targeting antibody), bearing a label, is injected and becomes localized at the site of the primary antibody by binding to avidin or biotin respectively. Alternatively other pairs of interacting molecules can substitute the biotin/streptavidin molecules. Several pretargeting approaches have been developed for antibodies (see Chang et al 2002. Mol. Cancer Therap. 1:553-563) that could be used to pretarget TCR-based reagents.

The invention can also be employed in applications that involve fluorescence activated cell sorting (FACS). FACS can be used to detect interactions between the soluble TCRs or fragments thereof and target cells. For example, the soluble TCR can be biotinylated in accordance with standard methods and combined with streptavidin-phycoerythrin (PE) to form labeled sc-TCR tetramers, for instance. However, as mentioned multimerization will often not be needed. FACS can be used to qualitatively measure the interaction of the soluble TCR and a suitable target cell such as T2 cells and tumor cell lines.

The following Examples show the construction and characterization of a novel fusion protein comprising a soluble single chain HLA-A2.1 restricted TCR that recognizes an unmutated p53 peptide spanning p53 amino acid residues 264-272, genetically linked to human IL-2. The peptide specific binding of the TCR portion of the molecule to peptide loaded HLA-A2 as well as the specific IL-2 receptor binding capability and bioactivity of the IL-2 portion of the molecule was investigated. The Examples show that these types of TCR based fusion proteins can serve as an alternative to antibody based targeted tumor therapies or as an addition to other targeted tumor therapies such as antibody based immunocytokines. Separate and distinct approaches to targeting a tumor may demonstrate additive or synergistic antitumor effects.

The Examples further show construction and expression of a soluble three domain mouse scTCR which recognizes human p53 peptide (aa 264-272) in the context of HLA-A2.1. The three domain scTCR is fused to human IL-2 yielding a soluble 264scTCR/IL-2 fusion protein which is expressed at high levels and secreted from mammalian cells. The TCR portion of the 264scTCR/IL-2 fusion protein retains its MHC-restricted, peptide specific antigen binding properties, and the IL-2 portion binds to IL-2 receptor and is biologically active. Moreover, the Examples further show that this fusion protein is capable of conjugating target and effector cells, exhibits favorable pharmacokinetics in mice, can bind to target tumor cells and has anti-tumor effects. Therefore, soluble scTCR fusion proteins will provide access to another repertoire of antigens for targeted immunotherapy, which are not recognizable by antibody based immunotherapies. TCR-based therapies will serve as an alternative to antibody based treatments or as a useful addition to other targeted tumor therapies.

The present disclosure shows that soluble TCR has sufficient affinity for peptide antigen to allow good detection. In particular, the affinity of the 264scTCR is sufficient to bind to unmanipulated tumor cells and effectively conjugate target and effector cells.

A reported problem surrounding systemic administration of cytokines to treat tumors is the short serum half life and toxicity of these proteins. Importantly, the 264scTCR/IL-2 fusion protein of the invention has an apparent serum half life of about 3 hours and appears to remain intact in the blood. Thus, the 264scTCR/IL-2 fusion protein effectively increases the half life of IL-2 and survives intact in the blood, suggesting that it is a new agent for immunomodulatory cancer therapy. At higher doses than used in the Example, the serum half life of the present fusion protein should increase [3, 25, 37, 38], thereby further improving the efficacy of the molecule against tumors.

There is recognition that IL-2 concentrated at the tumor site should activate local T-cells as well as other IL-2 responsive cells, thereby recruiting effector cells to the site of the tumor. Thus, by concentrating IL-2 at the site of a tumor, the present TCR fusion molecules may help potentiate a robust immune response including activation and proliferation of a variety of T-cell clones as well as activation of NK cells or other members of the innate immune system. Such a multi-faceted anti-tumor response will be more effective for the eradication of primary tumors as well as distant metastases.

The data show that it is possible to construct a biologically active bi-functional molecule comprised of a TCR and a cytokine. This fusion protein is capable of binding to tumor cells, mediating the conjugation of target and effector cells, and has reasonable pharmacokinetic properties. Besides p53, other gene products that are upregulated and presented in the context of MHC on tumor or virally infected cells may be used as targets for the present TCR-based immunotherapies. Further, other immunomodulatory molecules such as GM-CSF, IFNγ, or IFN-α can be linked to the TCR to activate other effector cells for an anti-tumor or anti-viral response. These novel TCR fusions will form a new class of immunotherapeutics for the treatment of cancer and viral infection.

By the term "specific binding" or a similar term is meant a molecule disclosed herein which binds another molecule, thereby forming a specific binding pair. However, the molecule does not recognize or bind to other molecules as determined by, e.g., Western blotting ELISA, RIA, mobility shift assay, enzyme-immuno assay, competitive assays, saturation assays or other protein binding assays know in the art. See generally, Ausubel, et al supra; Harlow and Lane in, *Antibodies: A Laboratory Manual* (1988) and references cited therein for examples of methods for detecting specific binding between molecules.

By the term "fully soluble" or similar term as it is meant to describe a TCR is meant that it is not readily sedimented under low G-force centrifugation from an aqueous buffer e.g., cell media. Further, a sc-TCR fusion protein is soluble if the fusion protein remains in aqueous solution at a temperature greater than about 5-37° C. and at or near neutral pH in the presence of low or no concentration of an anionic or non-ionic detergent. Under these conditions, a soluble protein will often have a low sedimentation value e.g., less than about 10 to 50 svedberg units. Aqueous solutions referenced herein typically have a buffering compound to establish pH, typically within a pH range of about 5-9, and an ionic strength range between about 2 mM and 500 mM. Sometimes a protease inhibitor or mild non-ionic detergent is added and a carrier protein may be added if desired such as bovine serum albumin (BSA) to a few mg/ml. Exemplary aqueous buffers include standard phosphate buffered saline, Tris-buffered saline, or other known buffers and cell media formulations.

The following non-limiting examples are illustrative of the invention.

Example 1

Generation of TCR Fusion Protein Constructs

A fusion protein comprising a three domain, HLA-A2.1 restricted mouse TCR specific for a p53 peptide antigen fused to human IL-2 was made. For this TCR fusion protein construct, the Va and V0/C0 regions were generated by RT-PCR from RNA isolated from a mouse T cell clone that produces TCRs specific for human p53 (aa 264-272) peptide. The carboxyl-terminal end of the variable region of the TCRa chain (Va3) was fused via a flexible linker $(G_4S)_4$ (SEQ ID NO: 17) [21] to the N-terminus of the V0 (Vβ3) to generate the antigen binding portion of the TCR. The C0 domain, which is directly linked to the V0 domain, was truncated at the amino acid residue just prior to the final cysteine, removing the transmembrane and cytoplasmic domains, to generate a soluble single-chain TCR molecule (FIGS. 1A and 1B). Human IL-2 was fused to the TCR portion via a short linker (amino acid sequence VNAKTTAPSVYPLAPV; SEQ ID NO:1). An EE tag (amino acid sequence EEEEYMPME; SEQ ID NO:2) [11] was inserted just downstream of the IL-2 portion of the fusion molecule to allow for detection of the TCR/IL-2 fusion protein by an anti-EE tag mAb [11] if desired. Mammalian cell expression is driven by a CMV promoter, secretion is directed by an antibody light chain leader, and selection was carried out by G418 resistance.

FIG. 1 is explained in more detail as follows. 1A) Schematic representation of the domain structure of the 264scTCR/IL-2 fusion protein. 1B) Amino acid sequence of 264scTCR/IL-2 fusion protein Amino acid numbers for each domain of the fusion protein are indicated in the figure.

Example 2

Expression of TCR/IL-2 Fusion Protein in Mammalian Cells

To characterize the 264scTCR/IL-2 fusion protein, the 264scTCR/IL-2 construct was stably transfected into CHO-K1 cells. Stable transfectants secreting 264scTCR/IL-2 fusion protein were selected using ELISA assays as described in Materials and Methods. Positive signals for these ELISAs indicate that the transfected cells secrete 264scTCR/IL-2 fusion protein that is recognized by both anti-murine TCR and anti-human IL-2 antibodies suggesting that the secreted 264scTCR/IL-2 is properly assembled and folded in the transfected cells and that it remains intact when it is secreted from the cells.

264scTCR/IL-2 fusion protein was purified from cell supernates by immunoaffinity chromatography with a yield of approximately 1.8 mg/1 of supernate. Purified fusion protein was subjected to SDS-PAGE and Coomassie staining. Under either reducing or non-reducing conditions, the predominant stained band migrated at approximately 60 kDa (FIG. 2), which is consistent with the predicted molecular mass for this protein and indicates that the fusion protein remains intact with no unexpected intramolecular disulfide bonds when it is secreted from the cells. The larger band in the nonreducing gel may be a dimer form of the fusion protein. This conclusion is based on the observation that the larger band has the apparent molecular mass approximately twice that of the fusion protein and this band is reduced to the size of the fusion protein under reducing conditions. The data indicate that the transfected CHO cells produce 264scTCR/IL-2 fusion protein of the expected molecular mass and that it is properly folded, assembled, and secreted as a soluble fusion protein.

FIG. 2 is explained in more detail as follows. CHO cells were stably transfected with the 264scTCR/IL-2 expression vector. The secreted fusion protein was purified by immunoaffinity chromatography and subjected to SDS-PAGE under either reducing or non-reducing conditions as indicated at the top of the figure. SDS-PAGE gels were stained with Coomassie brilliant blue.

Example 3

MHC/Peptide Binding Ability of the TCR Portion of the 264scTCR/IL-2 Fusion Protein The ability of the 264scTCR/IL-2 fusion protein to bind to peptide loaded MHC was determined by flow cytometry. T2 cells were loaded with p53 (aa 264-272) or p53 (aa 149-157) (control) peptide and stained with 264scTCR/IL-2 fusion protein. Cells loaded with p53 (aa 264-272) stained positively with 264scTCR/IL-2 when detected with either the anti-TCR Cβ mAb or the anti-IL-2 detection antibody (FIGS. 3A and 3B). Cells loaded with p53 (aa 149-157) control peptide did not stain with either the anti-TCR Cβ mAb or the anti-IL-2 detection antibodies. To demonstrate that the lack of staining of p53 (aa 149-157) loaded T2 cells is not due to an inability of the p53 (aa 149-157) peptide to bind to HLA-A2, T2 cells loaded with no peptide, p53 (149-157), or p53 (264-272) peptide were stained with BB7.2 α-HLA-A2 monoclonal antibody. Cells loaded with either p53 peptide stained stronger than cells loaded with no peptide, suggesting that both peptides are capable of binding to HLA-A2 molecules (FIG. 3C). T2 were also stained for IL-2 receptor and were found not to express IL-2 receptor; thus, these data indicate that binding of the 264scTCR/IL-2 fusion protein is mediated by the TCR component of the fusion protein. The lack of staining by the fusion protein when T2 cells were loaded with the control peptide also indicates that staining is mediated by the TCR component and that the staining is specific for the appropriate peptide. These data indicate that the TCR portion of the 264scTCR/IL-2 fusion protein is capable of recognizing its specific peptide in the context of HLA-A2.

FIG. 3 is explained more fully as follows. T2 cells were loaded with p53 (aa 264-272) peptide (gray line) or p53 (aa 149-157) peptide (black line), and stained with either 3A) 264scTCR/IL-2 fusion protein and anti-TCR Cβ mAb or 3B) 264scTCR/IL-2 fusion protein and anti-IL-2 mAb. 3C): T2 cells loaded with p53 (aa 264-272) peptide (dark grey line), p53 (aa 149-157) peptide (light grey line), or no peptide (black line) were stained with anti-HLA-A2 BB7.2 mAb followed by FITC labeled goat anti-mouse IgG. The shaded peak is unstained T2 cells.

Example 4

Figure 4A:
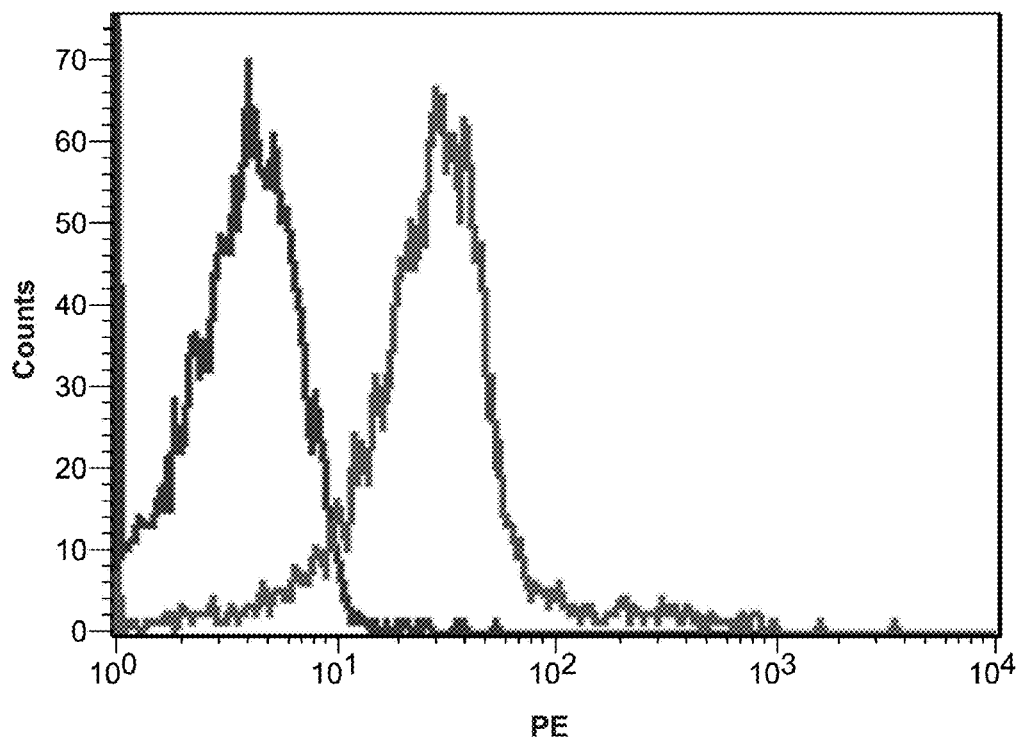
FIG. 4A-FIG. 4B are graphs showing IL-2 receptor binding ability of the IL-2 portion of 264scTCR/IL-2 fusion protein.
Figure 4B:
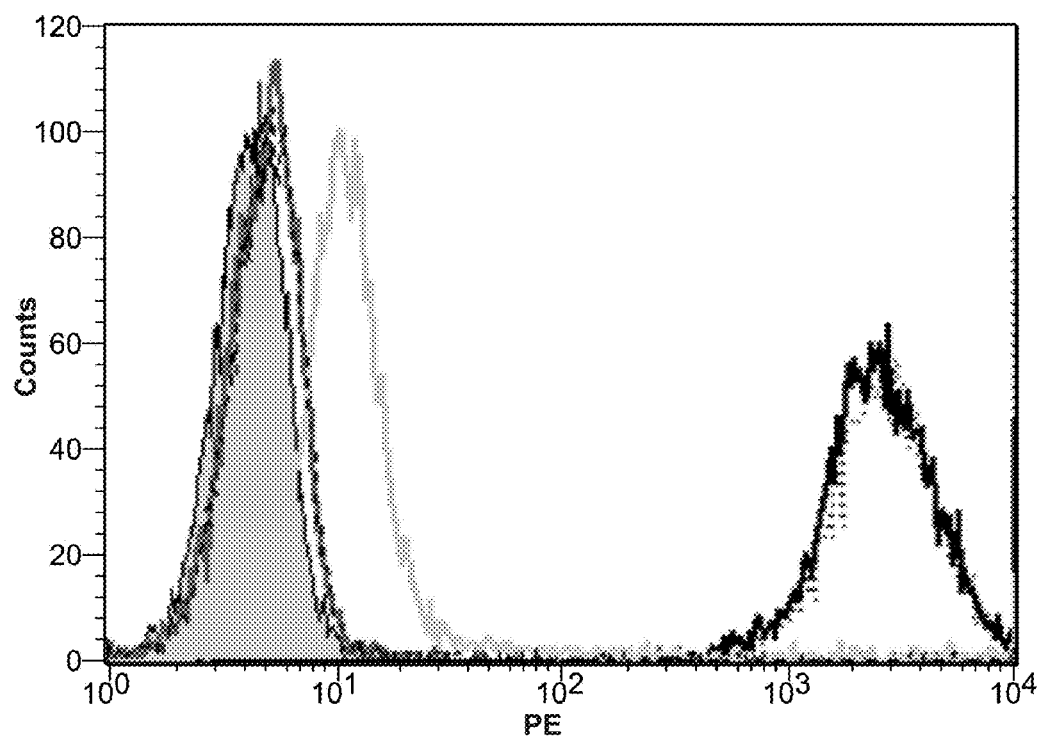

IL-2 Receptor Binding Ability of the IL-2 Portion of the 264scTCR/IL-2 Fusion Protein The IL-2 receptor binding capability of the IL-2 portion of the 264scTCR/IL-2 fusion protein was studied by flow cytometry. Primary mouse splenocytes were isolated and stimulated with rIL-2 and anti-CD3 to generate T cell blasts. Stimulated splenocytes that express IL-2 receptor stained positively with p53 (aa 264-272) loaded HLA-A2 tetramers only in the presence of 264scTCR/IL-2 fusion protein (FIG. 4A). Likewise, CTLL-2 mouse cytotoxic T lymphocytes, which constitutively express IL-2 receptor, stained positively with the 264scTCR/IL-2 fusion protein but not with a 264scTCR/kappa fusion protein (FIG. 4B). When CTLL-2 cells were incubated with α-human CD25 blocking antibody or isotype control antibody followed by 264scTCR/IL-2, staining was substantially reduced when the cells were incubated with the blocking antibody but not with isotype control antibody. The lack of signal from the CTLL-2 cells incubated with a 264scTCR/mouse kappa chain fusion protein or with IL-2 receptor blocking antibody indicates that staining of these cells is mediated by the IL-2 portion of the 264scTCR/IL-2 fusion protein. These data suggest that the IL-2 portion of the 264scTCR/IL-2 fusion protein is capable of binding to the IL-2 receptor.

FIG. 4 is explained in more detail as follows. 4A): Mouse splenocytes were stimulated with IL-2 and anti-CD3e mAb and then incubated in the presence (gray line) or absence (black line) of 264scTCR/IL-2 fusion protein. Bound fusion protein was detected with PE labeled HLA-A2 p53 (aa 264-272) tetramers. 4B): CTLL-2 cells were incubated with α-human CD25 blocking antibody or isotype control antibody followed by 264scTCR/IL-2 or 264scTCR/kappa fusion protein. Bound fusion protein was detected with PE labeled α-TCR-Vβ3 antibody. The shaded peak is unstained CTLL-2 cells. Black line: CTLL-2 cells stained with 264scTCR/IL-2 only. Gray dotted line: CTLL-2 cells incubated with control antibody followed by 264scTCR/IL-2. Light gray line: CTLL-2 cells incubated with α-human CD25 blocking antibody followed by 264scTCR/IL-2. Dark gray line: CTLL-2 cells stained with 264scTCR/kappa fusion protein. Black dashed line: CTLL-2 cells stained with α-TCR-Vβ.

Example 5

Biological Activity of 264scTCR/IL-2 Fusion Protein

Figure 5A:
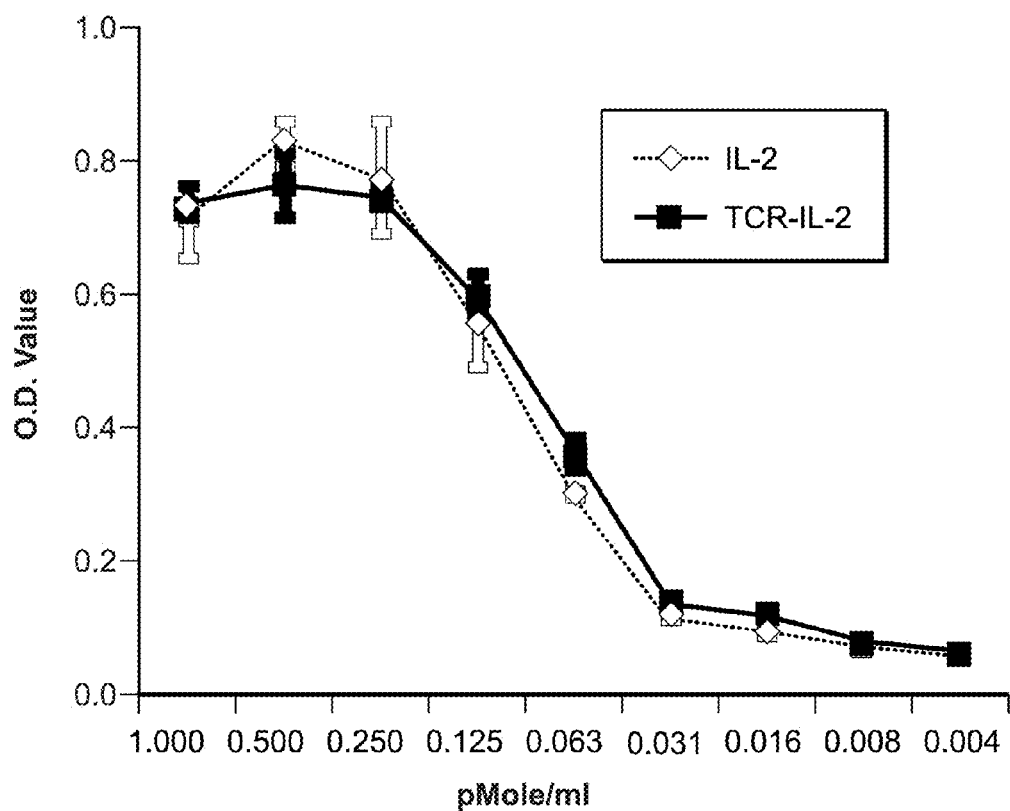
FIG. 5A-FIG. 5B are graphs showing biological activity of 264scTCR/IL-2 fusion protein.
Figure 5B:
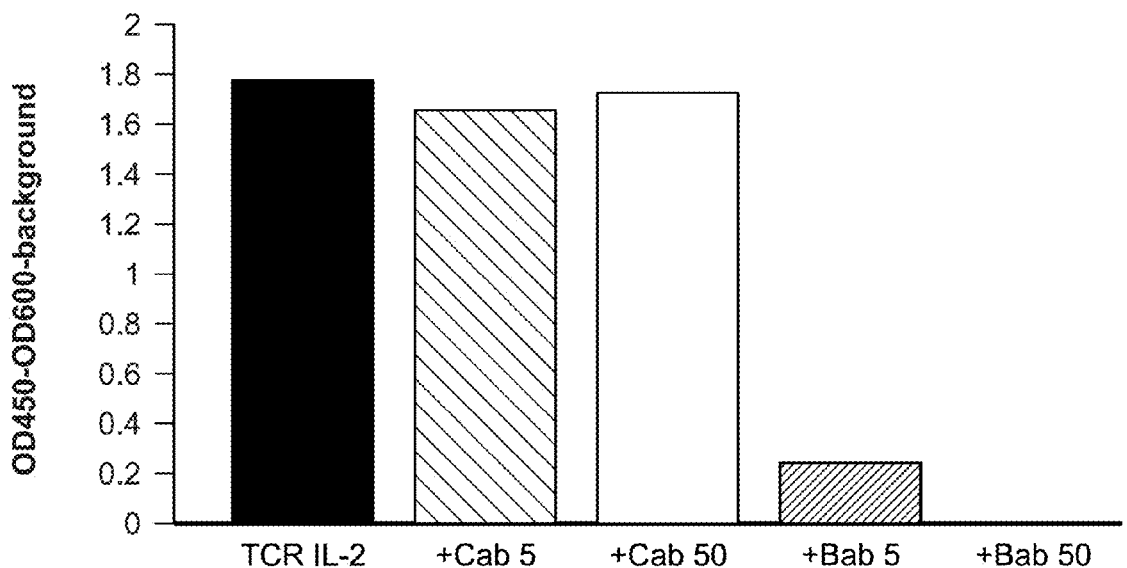

To demonstrate biological activity of the IL-2 portion of the 264scTCR/IL-2 fusion protein, IL-2 dependent CTLL-2 cells were cultured with either 264scTCR/IL-2 or recombinant IL-2 at various concentrations and cell viability was assessed using WST-1. As shown in FIG. 5A, the ability of rIL-2 or 264scTCR/IL-2 to support the growth of CTLL-2 cells was dose dependent, wherein there was more cell proliferation at higher doses of either recombinant IL-2 or 264scTCR/IL-2. Further, there were similar levels of cell proliferation when equivalent molar amounts of either recombinant IL-2 or 264scTCR/IL-2 were used. As a further control for specificity, CTLL-2 cells were incubated with 264scTCR/IL-2 with α-human CD25 blocking antibody or isotype control. When the blocking antibody was included in the culture, proliferation was substantially decreased with both concentrations of blocking antibody, but proliferation of the CTLL-2 cells was unaffected by either concentration of control antibody (FIG. 5B). The data indicate that the IL-2 portion of 264scTCR/IL-2 has similar biological activity to recombinant IL-2 in vitro and that the proliferation activity of the fusion protein is dependent on the IL-2 portion of the molecule.

The dissociation constant of the 264scTCR for its cognate MHC/peptide has been found to be approximately $10^{-7}$ M at physiological conditions using surface plasmon resonance detection.

FIG. 5 is explained more fully as follows. 5A): CTLL-2 cells were cultured with 264scTCR/IL-2 (solid line) or recombinant IL-2 (dotted line) at various concentrations as indicated at the bottom of the FIG. 5B): CTLL-2 cells were incubated with 264scTCR/IL-2 and α-human CD25 blocking antibody or isotype control antibody as indicated at the bottom of the figure. Cell viability was measured by incubation with WST-1 and absorbance was read at 450 nm. Cab+5: 5 µg control antibody; Cab+50: 50 µg control antibody; Bab+5: 5 µg blocking antibody; Bab+50: 50 µg blocking antibody.

Example 6

Conjugation of Cells Mediated by 264scTCR/IL-2 Fusion Protein

Figure 6A:
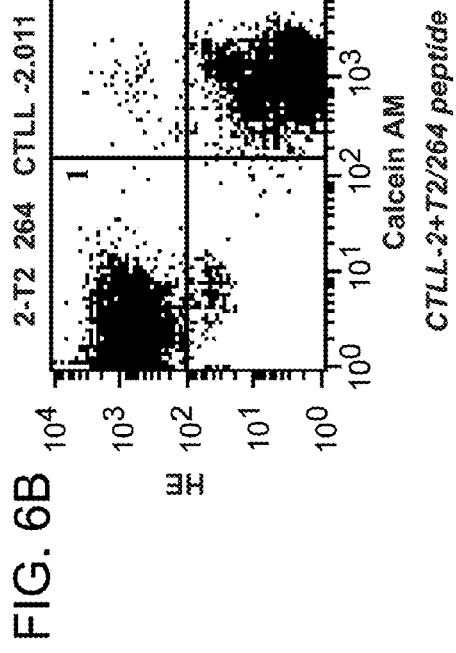
FIG. 6A, FIG. 6B, FIG. 6C, and FIG. 6D are graphs showing conjugation of CTLL-2 cells with peptide-loaded T2 cells mediated by 264scTCR/IL-2 fusion protein.
Figure 6B:
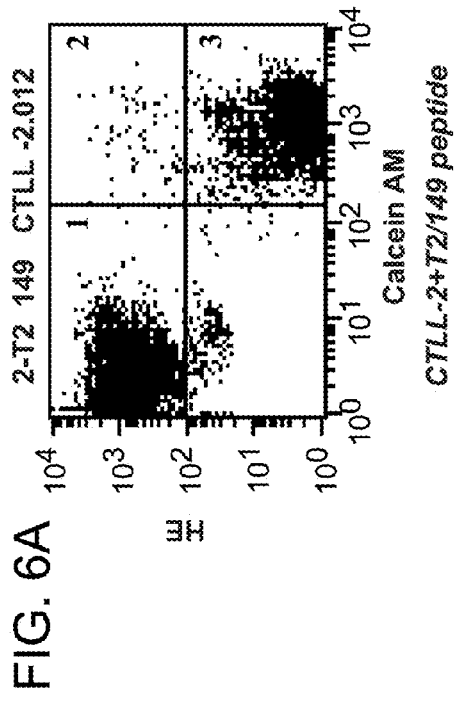
Figure 6C:
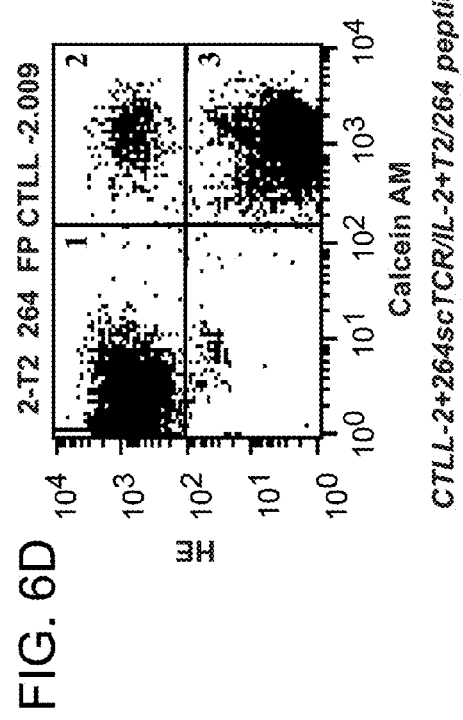
Figure 6D:
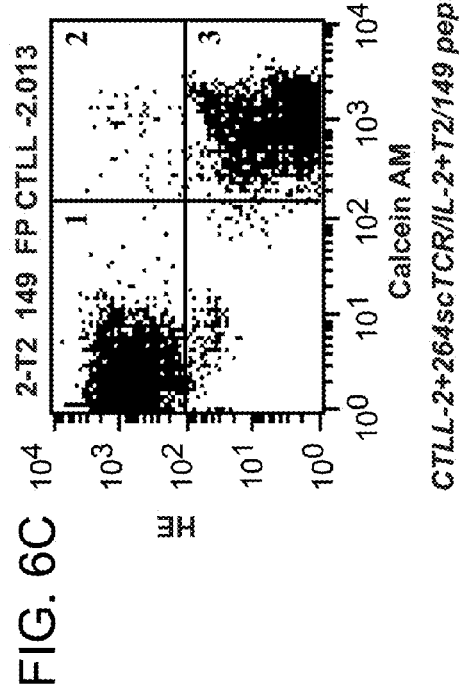

A useful property for the 264scTCR/IL-2 fusion protein would be capacity to bring together target and effector cells through its TCR and cytokine portions, respectively. To demonstrate that the 264scTCR/IL-2 fusion protein can effectively conjugate cells, T2 cells were loaded with either p53 (aa 264-272) or p53 (aa 149-157) peptides and then labeled with dihydroethidium (HE). CTLL-2 cells were labeled with calcein AM and the two labeled cell populations were mixed and incubated in the presence or absence of 264scTCR/IL-2 fusion protein. Samples were analyzed by flow cytometry. When the two cell populations were incubated in the absence of the 264scTCR/IL-2 fusion protein (FIGS. 6A and 6B) or when the T2 cells were loaded with control peptide and incubated with the CTLL-2 cells in the presence of 264scTCR/IL-2 fusion protein (FIG. 6C), the cells remained as two distinct populations on the flow cytometry histograms representing approximately 45% of the total population each (FIGS. 6A, 6B, and 6C, regions 1 and 3) with only approximately 0.46% of the total population falling in the double stained cell window (FIGS. 6A, 6B, and 6C, region 2). However, when the T2 cells were loaded with p53 (aa 264-272) peptide and incubated with the CTLL-2 cells in the presence of the 264scTCR/IL-2 fusion protein (FIG. 6D), a double staining population of cells appears, representing 4.1% of the total population (FIG. 6D, region 2, conjugated cells), suggesting that T2 cells were conjugated to CTLL-2 cells via the 264scTCR/IL-2 fusion protein.

FIG. 6 is explained in more detail as follows. T2 cells were loaded with either p53 (aa 264-272) (6B and 6D) or p53 (aa 149-157) (control) peptides (6A and 6C) and then labeled with HE. CTLL-2 cells were labeled with calcein AM. Labeled cells were mixed and incubated in the presence (6C and 6D) or absence (6A and 6B) of 264scTCR/IL-2 fusion protein and the samples were analyzed by flow cytometry. Assay conditions including loading peptide used, and presence or absence of fusion protein, are indicated beneath each histogram. Single stained regions are marked 1 and 3 and the double stained cell population is marked 2.

Example 7

Pharmacokinetics of 264scTCR/IL-2 in Mice

Figure 7A:
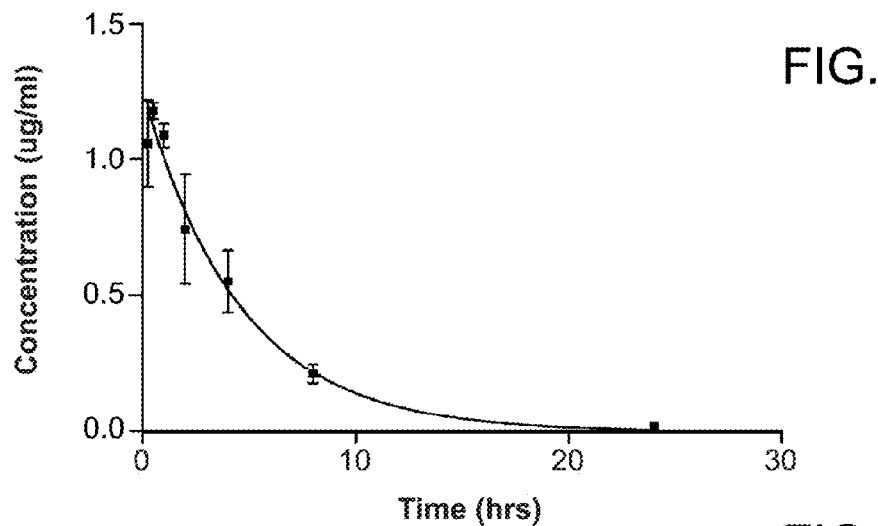
FIG. 7A, FIG. 7B, and FIG. 7C are graphs showing serum half life of 264scTCR/IL-2 fusion protein.
Figure 7B:
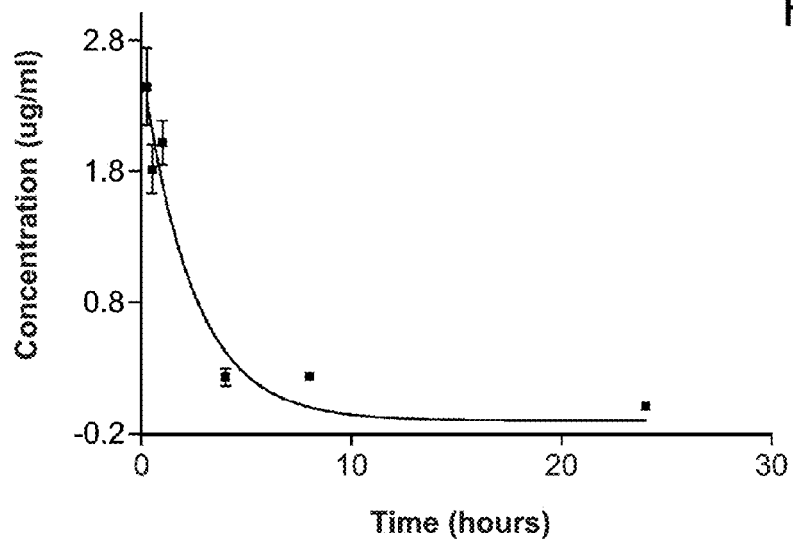
Figure 7C:
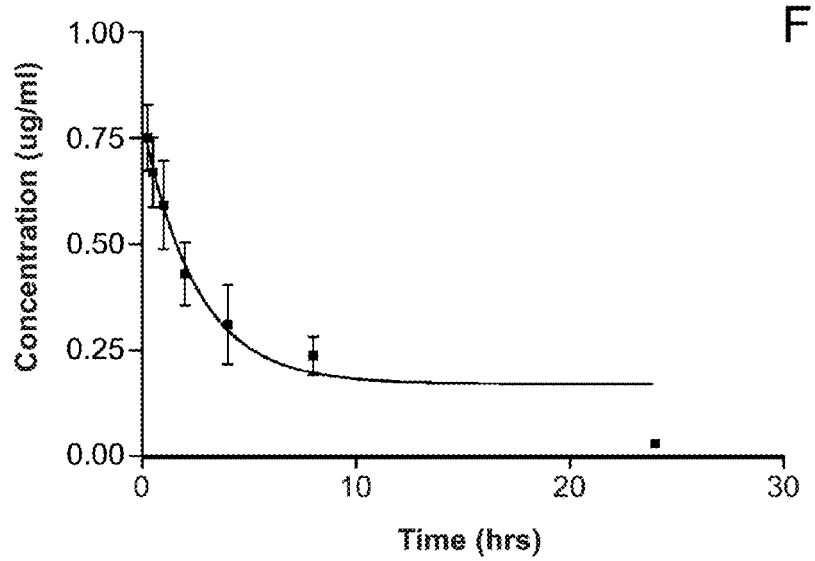

The pharmacokinetics of the 264scTCR/IL-2 fusion protein was measured in BALB/c mice. Mice were injected intravenously and serum samples were collected various time points. The serum levels of 264scTCR/IL-2 fusion protein were measured using ELISA. The ELISA detection was performed using anti-TCR mAb capture/anti-IL-2 Ab detection (FIG. 7A), anti-TCR mAb capture/anti-TCR mAb detection (FIG. 7B), or anti-IL-2 mAb capture/anti-IL-2 polyclonal Ab detection (FIG. 7C) to determine whether the fusion protein is modified or cleaved in vivo. Mice injected with 264scTCR/IL-2 fusion protein showed no obvious signs of toxicity. In these assays a maximum concentration of 0.75 to 2.5 µg/ml of 264scTCR/IL-2 was detected with an apparent serum half-life of 1.6 to 3.0 hours depending on the ELISA format used (FIG. 7). Since the reported serum half-life of free IL-2 is only about 5 minutes [6], these data indicate that the fusion protein is not cleaved in vivo but instead remains intact for a relatively long period of time in the blood. The small variability in the half-life of 264scTCR/IL-2 determined in these studies is most likely due to the differences in the sensitivity of the ELISA assays.

FIG. 7 is explained in more detail as follows. BALB/c mice were injected with 264scTCR/IL-2 fusion protein and serum samples were collected at 15 and 30 minutes, 1, 4, 8, and 24 hours post injection. Serum concentrations of 264scTCR/IL-2 were determined by ELISA using the following formats: 7A): Anti-TCR mAb capture/anti-IL-2 Ab detection; 7B): Anti-TCR mAb capture/anti-TCR mAb detection; and 7C): Anti-IL-2 mAb capture/anti-IL-2 Ab detection.

Example 8

Tumor Cell Staining with 264scTCR/IL-2

Figure 8:
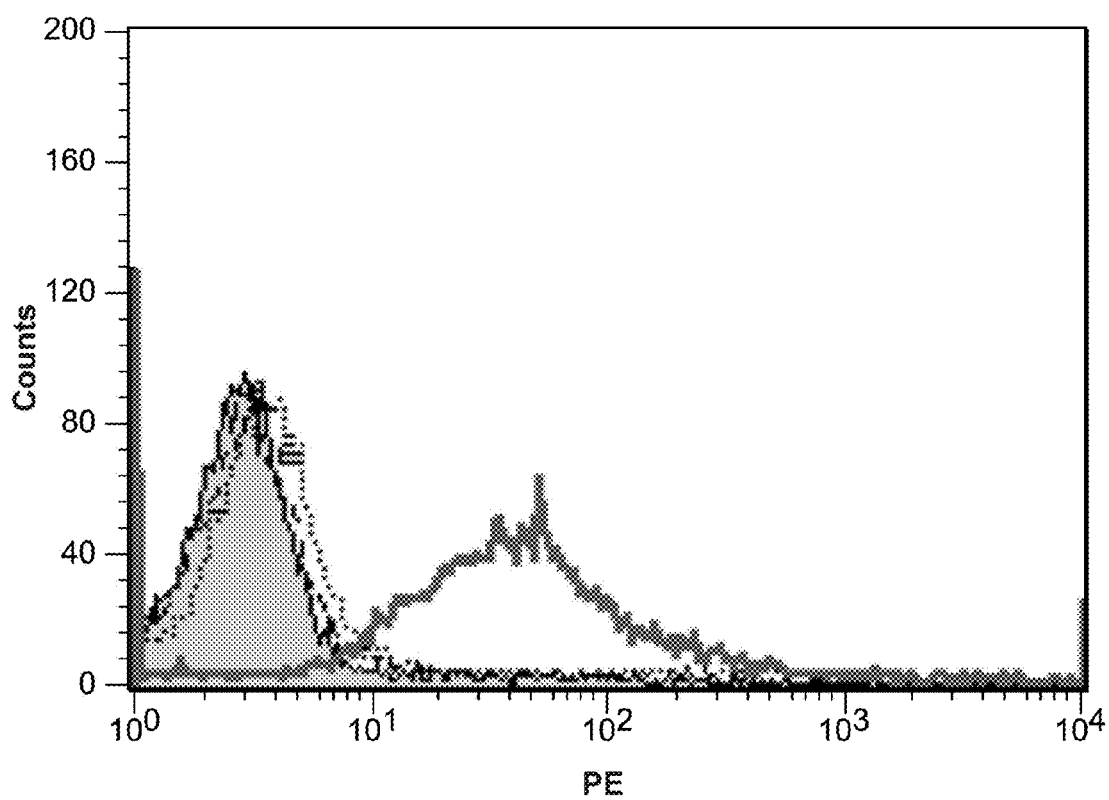
FIG. 8 is a graph showing tumor cell staining with 264scTCR/IL-2 fusion protein.

It would be useful if the 264scTCR/IL-2 fusion protein could recognize and bind to its target tumor cells. To test whether the 264scTCR/IL-2 is capable of binding to tumor cells, A375 human melanoma cells, which express both HLA-A2.1 and p53, were stained with either 264scTCR/IL-2 or 3C8, an irrelevant TCR/IL-2 fusion protein. Cells not incubated with fusion protein and cells incubated with 3C8 did not stain with the H57-597 detection antibody, while cells incubated with 264scTCR/IL-2 stained positively with the detection antibody (FIG. 8). This result suggests that the 264scTCR/IL-2 fusion protein is capable of recognizing and binding to its target tumor cell and is useful as an anti-cancer therapeutic in vivo.

FIG. 8 is explained more fully as follows. A375 human melanoma cells were incubated with no fusion protein (dashed black line), 5 µg 3C8 TCR/IL-2 fusion protein (control) (dotted line), or 5 µg 264scTCR/IL-2 fusion protein (solid black line) followed by staining with H57-597 mAb. Unstained cells are represented by the shaded area.

Example 9

Anti-Tumor Effects of 264scTCR/IL-2 Fusion Protein

Figure 9:
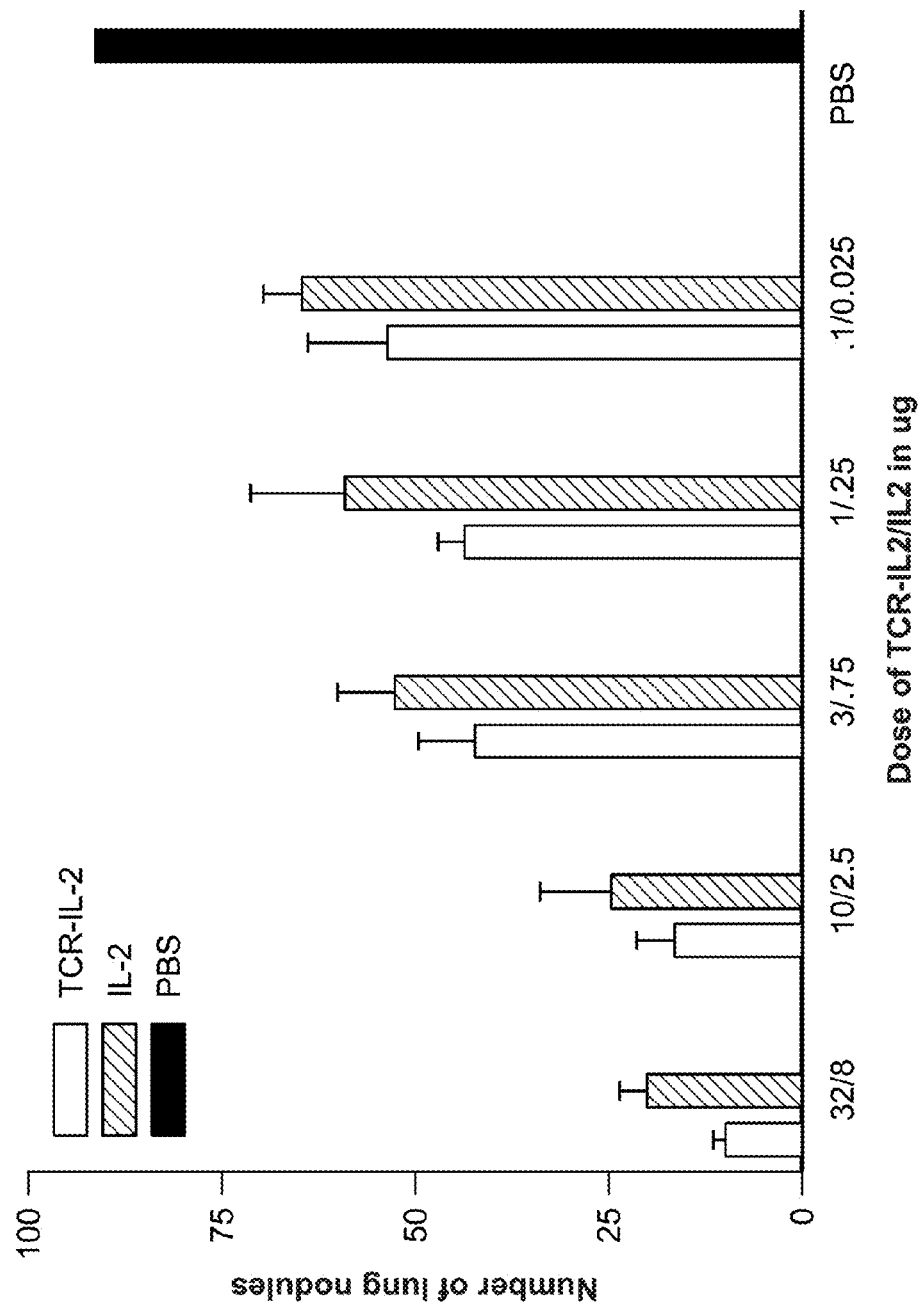
FIG. 9 is a graph showing anti-tumor effect of 264scTCR/IL-2 fusion protein.

To determine if the 264scTCR/IL-2 fusion protein has anti-tumor activity in vivo, an experimental metastasis assay was performed. Female athymic nude mice were injected with the highly metastatic A375 human melanoma subclone, A375-C15N, and treated with varying doses of either 264scTCR/IL-2 or recombinant IL-2. Forty-two days after tumor cell injection, lung nodules were counted. Both 264scTCR/IL-2 and recombinant IL-2 reduced lung metastasis in a dose dependent manner (FIG. 9). However, at all doses lung metastasis was reduced to a greater degree with the 264scTCR/IL-2 fusion protein, suggesting that targeting the cytokine to the tumor may provide greater efficacy as a cancer therapeutic.

Mice treated with either 264scTCR/IL-2 or recombinant IL-2 showed no obvious signs of toxicity. Both treatments resulted in reduction of lung metastasis; however, at all doses treatment with 264scTCR/IL-2 was more effective than recombinant IL-2.

FIG. 9 is explained more fully as follows. Female athymic nude mice were injected with highly metastatic A375-C15N cells and treated with 264scTCR/IL-2, recombinant IL-2, or PBS. Forty-two days after tumor cell injection, the lungs were removed, lung nodules were counted, and the mean number of lung nodules relative to the PBS treated control group was plotted.

Example 10

Figure 10A:
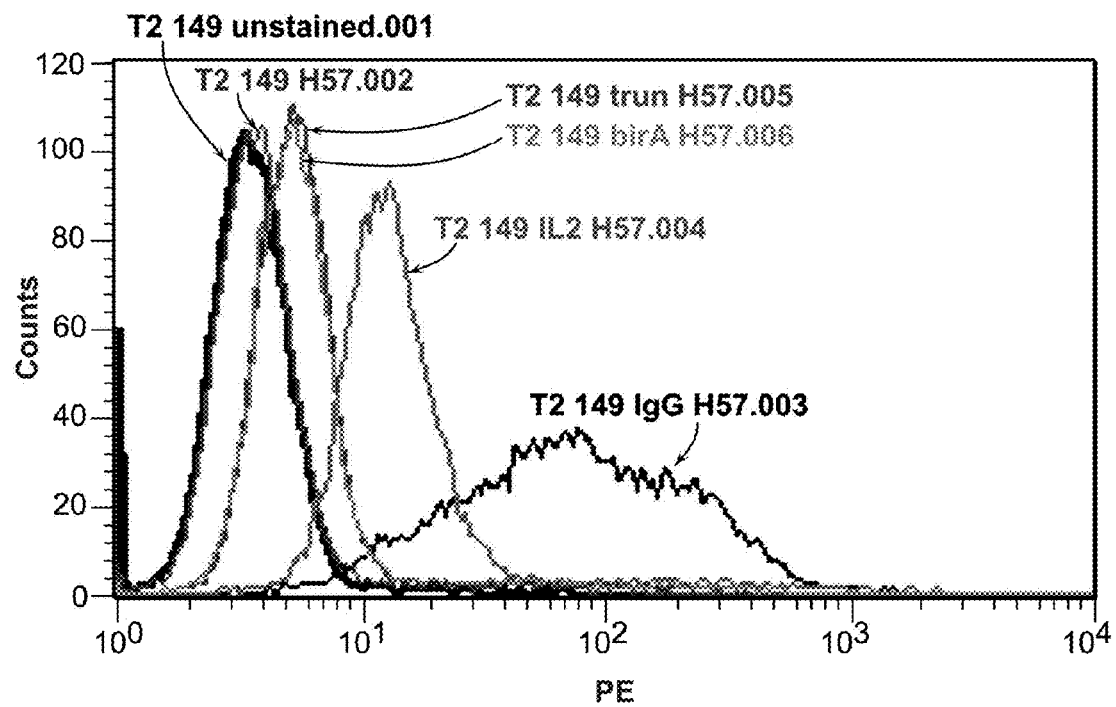
FIG. 10A and FIG. 10B are graphs showing staining of T2 cells loaded with non-specific p53 peptide (FIG. 10A) or specific p53 peptide (FIG. 10B) with 264scTCR reagents.
Figure 10B:
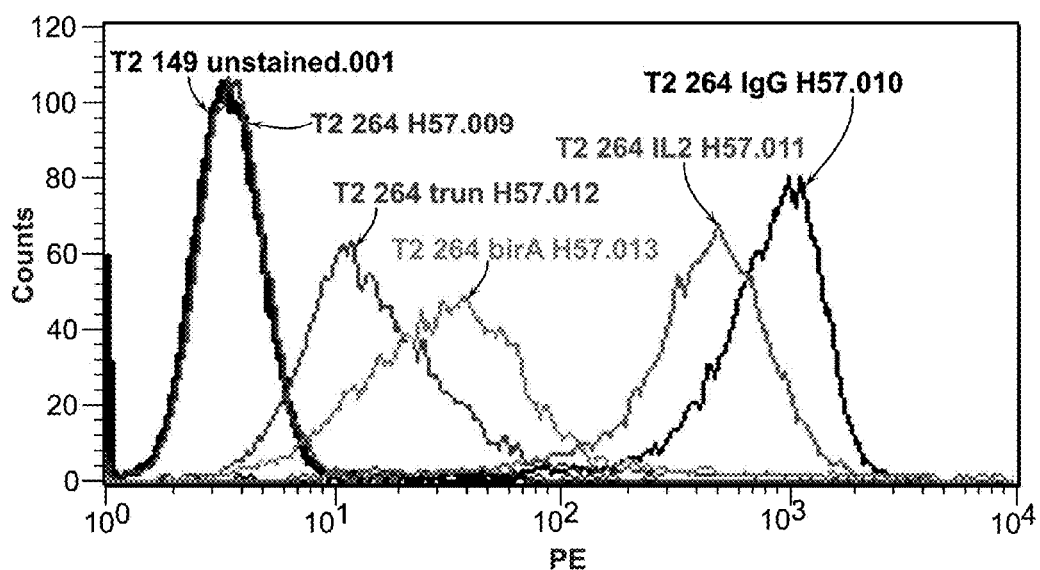

Flow Cytometric Analysis of Staining of Peptide-Loaded T2 Cells by Monomeric and Multimeric 264scTCR Fusion Proteins Monomeric or multimeric forms of various 264scTCR fusion proteins were prepared and their binding to T2 cells was analyzed by flow cytometry as described in Methods, sections 11 and 12, below. The results, shown in FIG. 10, demonstrate that the 264scTCR fusion proteins stained p53 (aa264-273)-loaded T2 cells (FIG. 10B) to a greater degree than p53 (aa149-157)-loaded cells (FIG. 10A). In the figures, unstained T2 cells are shown in the histogram labeled T2 149 unstained.001; p53 (aa149-157)- and p53 (aa264-273)-loaded T2 cells stained with the secondary reagent (H57-PE) are shown in the histograms labeled "T2 149 H57.002" and "T2 264 H57.009", respectively; p53 (aa149-157)- and p53 (aa264-273)-loaded T2 cells stained with multimeric 264scTCR/IgG1 followed by H57-PE are shown in the histograms labeled "T2 149 IgG H57.003" and "T2 264 IgG H57.010", respectively; p53 (aa149-157)- and p53 (aa264-273)-loaded T2 cells stained with 264scTCR/IL-2 followed by H57-PE are shown in the histograms labeled "T2 149 IL2 H57.004" and "T2 264 IL2 H57.011", respectively; p53 (aa149-157)- and p53 (aa264-273)-loaded T2 cells stained with monomeric 264scTCR/trunIgG1 followed by H57-PE are shown in the histograms labeled "T2 149 trun H57.005" and "T2 264 trun H57.012", respectively; and p53 (aa149-157)- and p53 (aa264-273)-loaded T2 cells stained with monomeric 264scTCR/BirA followed by H57-PE are shown in the histograms labeled "T2 149 birA H57.006" and "T2 264 birA H57.013", respectively. This result confirmed that the observed staining is peptide-specific.

Monomeric forms of the 264scTCR were able to stain to some degree. For example, the mean channel fluorescence (MCF) for staining with the 264scTCR/trunIgG form increased from 10.95 for the p53 (aa149-157)-loaded cells to 55.34 for the p53 (aa264-273)-loaded cells. Similarly, the MCF for the 264scTCR/BirA form increased from 13.41 for p53 (aa149-157)-loaded cells to 95.14 for the p53 (aa264-273)-loaded cells. Multimeric forms of the 264scTCR were able to specifically stain the peptide-loaded T2 cells to an even greater extent. For example, the MCF for the 264scTCR/IgG1 form increased from 119 for p53 (aa149-157)-loaded cells to 863 for the p53 (aa264-273)-loaded cells.

Example 11

Staining of Tumor Cells by 264scTCR Fusion Proteins

The ability of the 264scTCR reagents to stain tumor cells was also tested. Cultured A375 cells were detached with 10 mM EDTA in PBS (pH7.4) and washed twice with washing buffer. Cell staining was carried out using 4 µg 264scTCR/IgG1 fusion protein for 45 minutes at 23° C. The cells were washed once and stained with 3 µg FITC-conjugated F(ab')$_2$ fragment of goat anti-human IgG Fc (anti IgG-FITC). After washing twice, the stained cells were resuspended and analyzed on a FACScan. A375 cells stained with anti IgG-FITC alone were run as a control.

Figure 11B:
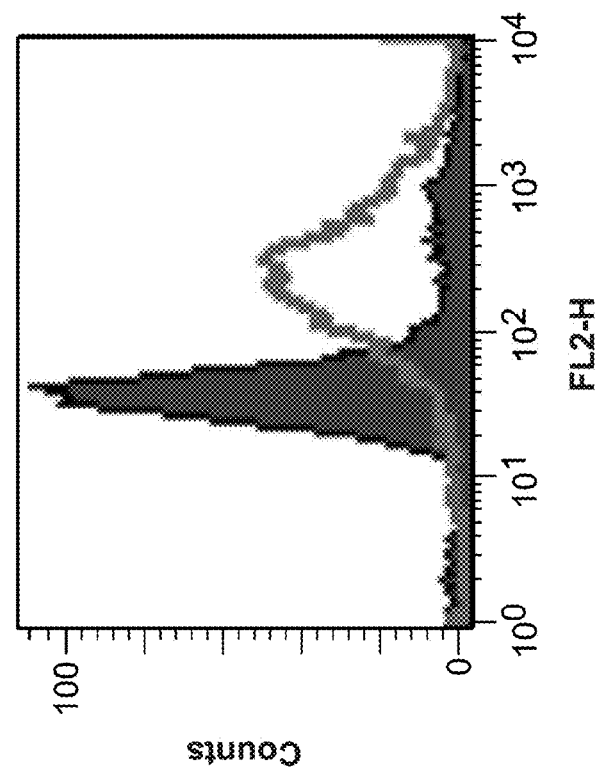
FIG. 11A, FIG. 11B, FIG. 11C, and FIG. 11D are graphs showing staining of tumor cells with various 264scTCR reagents and secondary reagents.
Figure 11A:
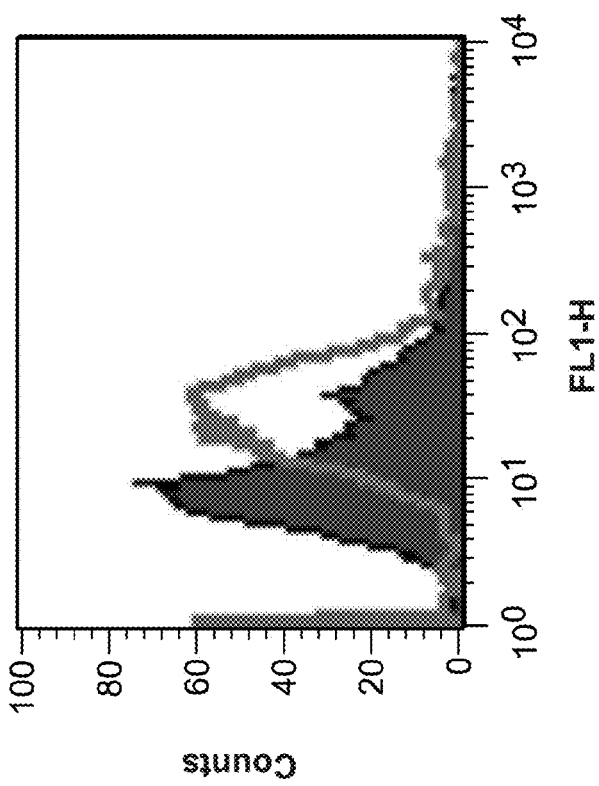
Figure 11D:
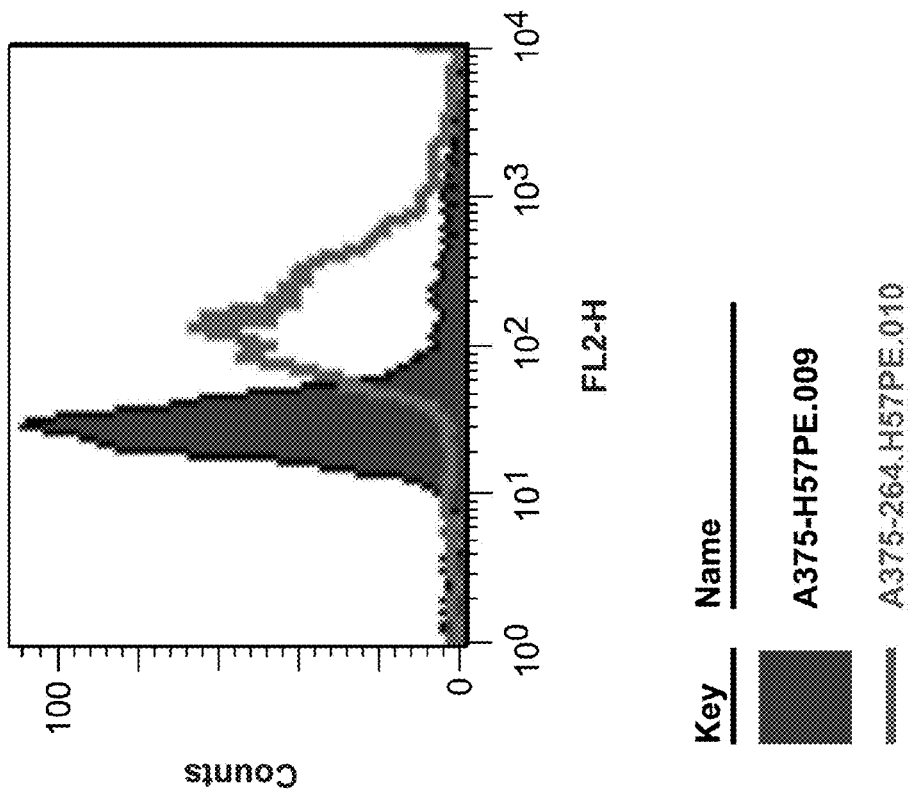
Figure 11C:
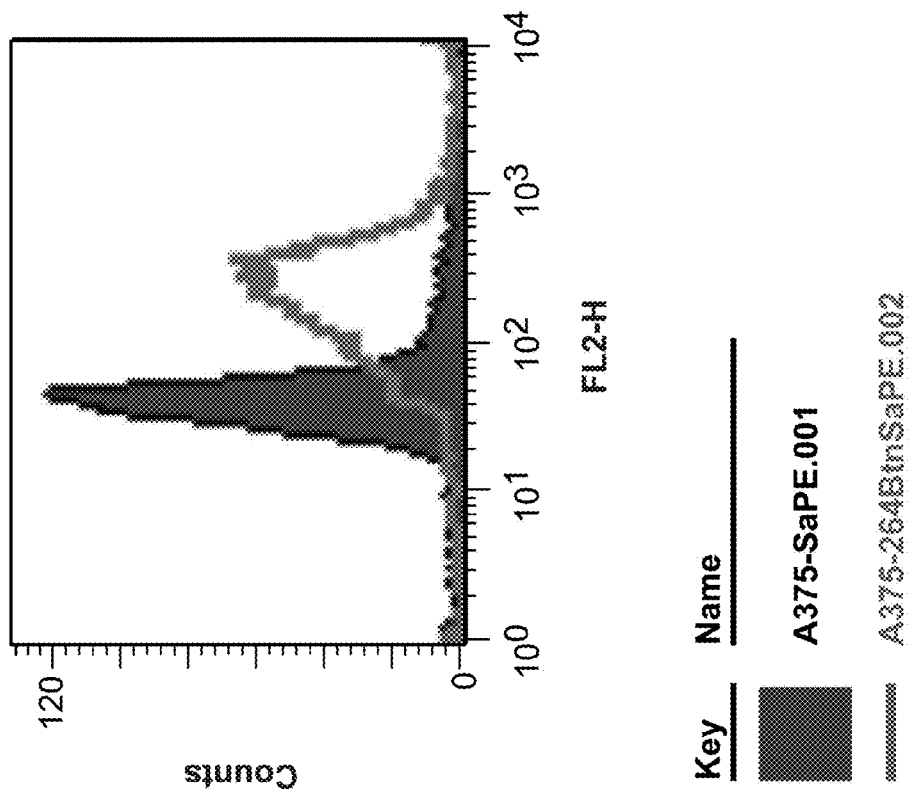

Referring to FIG. 11A, the results of this analysis show that A375 tumor cells could be stained with the 264scTCR/IgG1 fusion protein. In this panel (11A), A375 cells stained with anti IgG-FITC alone or 264scTCR/IgG1 followed by anti IgG-FITC are shown in histograms labeled "A375-FITC.005" and "A375-264.FITC.006", respectively. Additional experiments using A375 tumor cells were performed to further characterize optimal staining conditions. For example, PE-conjugated anti-human IgG antibody (anti IgG-PE) (FIG. 11B) or PE-conjugated H57 mAb (FIG. 11D) were used in place of the FITC-conjugated antibody as a secondary reagent. In FIG. 11B, A375 cells stained with anti IgG-PE alone or 264scTCR/IgG1 followed by anti IgG-PE are shown in histograms labeled "A375-PE.007" and "A375-264.PE.008", respectively. In FIG. 11D, A375 cells stained with H57-PE alone or 264scTCR/IgG1 followed by H57-PE are shown in histograms labeled "A375-H57PE.009" and "A375-264.H57PE.010", respectively. In each case, the 264scTCR/IgG1 stained the A375 tumor cells. Biotinylated 264scTCR/BirA that had been multimerized with streptavidin-PE (SA-PE) was also used to stain A375 cells (FIG. 11C), and showed increased staining compared with the cells stained with streptavidin-PE alone. Referring to FIG. 11C, A375 cells stained with SA-PE alone or biotinylated 264scTCR/BirA complexed with SA-PE are shown in histograms labeled "A375-SAPE.001" and "A375-264BtnSaPE.002", respectively.

Example 12

Staining of Fixed Cells by 264scTCR Fusion Proteins Detected by Flow Cytometry As discussed, the ability to detect MHC/peptide complexes in preserved or "fixed" samples is advantageous, especially in clinical or other medical settings where it is typical practice to fix cells, tissues or other biological samples taken from patients. However, since the MHC/peptide complex represents a cell surface antigen composed of three separate polypeptide chains, it is uncertain that the structural integrity of the MHC/peptide complex would remain sufficiently intact for detection by the soluble TCR following typical fixation procedures. To assess whether soluble TCR staining could be carried out on fixed cells, peptide-loaded T2 cells and unmanipulated A375 tumor cells were analyzed by flow cytometry. Cultured A375 cells were detached with 10 mM EDTA in PBS (pH 7.4) and washed twice with washing buffer. T2 cells were incubated with 50 µM p53 (aa264-273) for 3 hours and then washed twice with washing buffer. Both cell types were fixed with 3.7% formaldehyde for 5 minutes and washed twice. Cell staining was carried out using 4 µg 264scTCR/IgG1 or CMVscTCR/IgG1 fusion protein in the presence or absence of 20 µg HLA-A2.1/p53 (aa 264-272) tetramers for 45 minutes at 23° C. The cells were washed once and stained with 3 µg FITC-conjugated F(ab')$_2$ fragment of goat anti-human IgG Fc. After washing twice, the stained cells were resuspended and analyzed on a FACScan.

Referring to FIG. 12A, the results showed that the 264scTCR/IgG1 fusion protein positively stained the formaldehyde-fixed A375 cells (histogram labeled "A375F-264.006"), while staining with CMVscTCR/IgG1 (histogram labeled "A375F-CMV.005") was not detectable above background. Since the CMV peptide is not present on A375 cells, use of the CMVscTCR/IgG1 control reagent provides a measure of any non-specific interactions between the TCR or IgG1 domains with the tumor cells. By determining the difference in tumor cell staining between the 264scTCR/IgG1 fusion protein and the CMVscTCR/IgG1 control, this method allows direct measurement of the level of tumor antigen presentation on the surface of the fixed tumor cell sample.

To confirm that A375 cell staining with 264scTCR/IgG1 fusion protein was TCR-specific, HLA-A2.1/p53 (aa 264-272) tetramers were used as blocking reagents. Staining of A375 cells with 264scTCR/IgG1 was reduced by the addition of HLA-A2.1/p53 (aa 264-272) tetramer blocking reagent (histogram labeled "A375F-264TET.264.008"), further indicating that 264scTCR/IgG1 can specifically bind to tumor cells. As expected, addition of HLA-A2.1/pCMV tetramer reagent to A375 cells stained with 264scTCR/IgG1 did not have any effect on the specific staining of the 264scTCR/IgG1 reagent (histogram labeled "A375F-264TET.CMV.007"). Similar results were seen with the peptide-loaded T2 cells (FIG. 12B).

These results demonstrate the monomeric and multimeric soluble TCR reagents can specifically stain cells presenting a peptide in the context of an MHC complex. Furthermore, soluble TCR reagents can specifically stain unfixed and fixed tumor cells presenting a tumor antigen in context of an MHC complex. In addition, specific staining of the cells by the soluble TCR reagent could be reduced by the addition of a completing MHC molecule that binds the soluble TCR reagent. Addition of a 1 to 100 fold molar excess of the completing MHC molecule over the soluble TCR reagent in control staining reactions is particularly useful in distinguishing the specific binding component (i.e. binding to peptide-MHC) versus the non-specific binding component of soluble TCR staining. This is relevant when comparing staining of different cells and tissues that may exhibit different degrees of non-specific and specific soluble TCR binding. For example, variability between the non-specific binding of the soluble TCR in different samples (cells or tissues) would make it extremely difficult to determine the degree of specific soluble TCR binding without the use of an appropriate completing MHC molecule in a control staining reaction.

Example 13

Staining of Fixed Cells by 264scTCR Fusion Proteins Detected by Immunofluorescent Microscopy Several cell lines that vary with respect to HLA-A2 and p53 expression (i.e., A375, HT29 and Saos2) were chosen for analysis and stained with either 264scTCR/IgG1 fusion protein or control fusion protein CMVscTCR/IgG1. The cells were cultured on cover slips for 24 hours and then fixed with 3.7% formaldehyde for 5 minutes and washed twice with washing buffer (0.5% BSA and 0.1% sodium azide in PBS). The BSA represents a blocking agent to reduce nonspecific protein binding. The cells were stained with 10 µg 264scTCR/IgG1 or CMVscTCR/IgG1 fusion protein in 200 µl of PBS containing 5% normal goat serum (NGS) for 45 minutes at 23° C. The NGS represents a blocking agent to reduce nonspecific binding. The cells were washed twice and stained with 3 µg FITC-conjugated F(ab')$_2$ fragment of goat anti-human IgG Fc□ (Jackson ImmunoResearch, West Grove, Pa.). The cells were washed twice and then once with equilibration buffer (Molecular Probes, Eugene, Oreg.). Cover slips were mounted on glass slides with anti-fade reagent in glycerol buffer (Molecular Probes, Eugene, Oreg.) and sealed with nail oil. The slides were documented using a Nikon epi-fluorescence microscope (Nikon, Tokyo, Japan) with a SPOT RT camera and SPOT RT software v3.2 (Diagnostic Instrument, Sterling Heights, Mich.).

For HLA-A2 staining, the fixed cells were stained with 10 µg BB7.2, a mouse anti-human HLA-A2 antibody, in 200 µl of PBS containing 5% normal goat serum (NGS) for 45 minutes at 23° C. The cells were washed twice and stained with 4 µg FITC-conjugated F(ab')$_2$ fragment of goat anti-mouse IgG Fc□ (Jackson ImmunoResearch, West Grove, Pa.). The cells were washed twice and then once with equilibration buffer (Molecular Probes, Eugene, Oreg.). Cover slips were mounted and documented as described above.

For p53 staining, the fixed cells were permeabalized with 0.2% TrintonX-100 for 20 minutes and then stained with 10 µg PAb122, a mouse anti-p53 antibody, in 200 µl of PBS containing 5% normal goat serum (NGS) for 45 minutes at 23° C. The cells were washed twice and stained with 4 µg FITC-conjugated F(ab')$_2$ fragment of goat anti-mouse IgG Fc□ (Jackson ImmunoResearch, West Grove, Pa.). The cells were washed twice and then once with equilibration buffer (Molecular Probe, Eugene, Oreg.). Cover slips were mounted and documented as described above.

Figure 13:
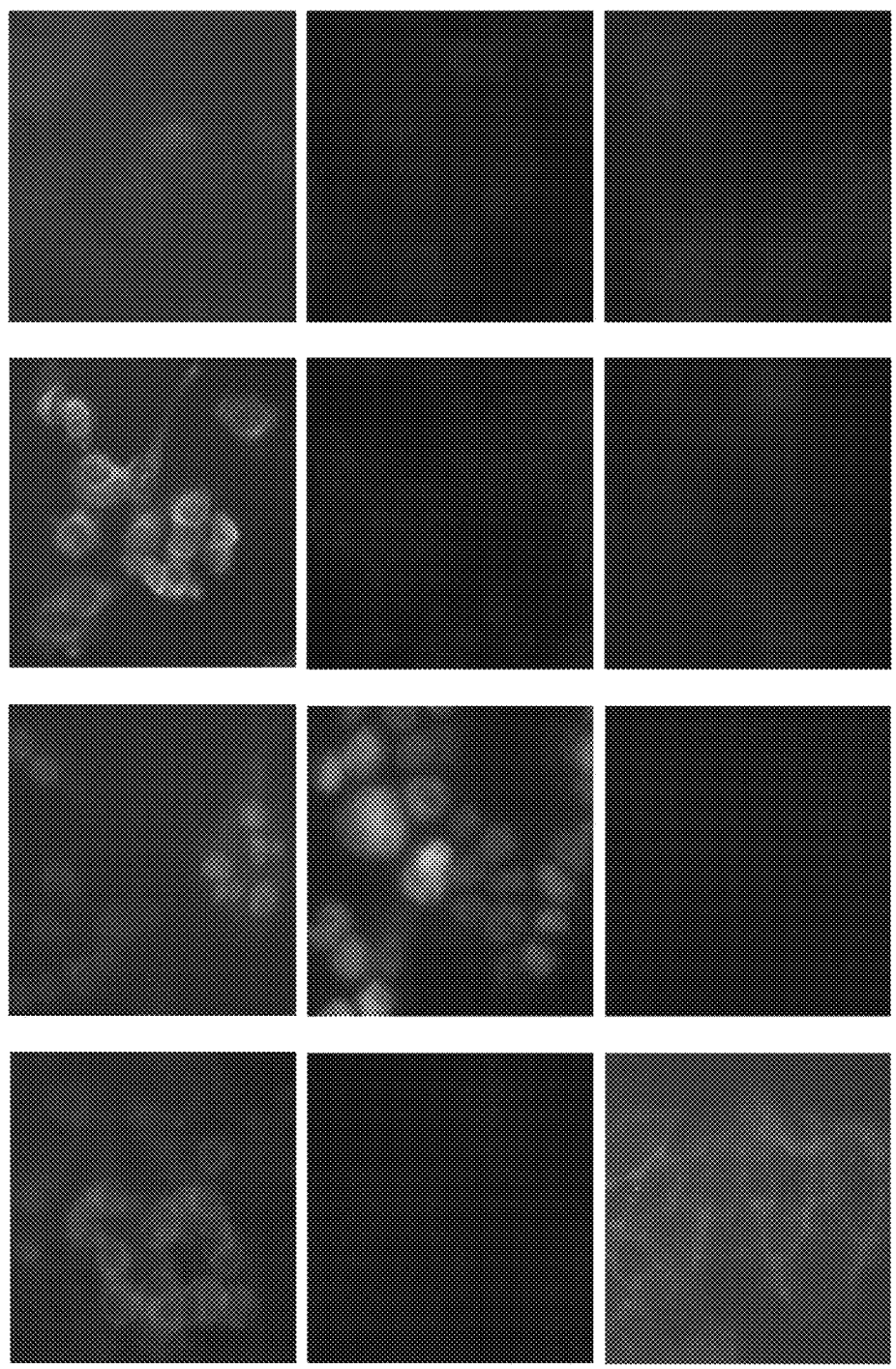
FIG. 13 is a series of photomicrographs showing staining patterns of fixed tumor cell types (A375, HT29 and Saos2) for A2 and p53 antigens and with 264scTCR/IgG1 and CMVscTCR/IgG1 fusion proteins.

As shown in FIG. 13, A375 cells stained positively for HLA-A2 and p53, HT29 stained positively for p53 but not HLA-A2 and Saos2 cells stained positively for HLA-A2 but not p53 Immunofluorescent staining with 264scTCR/IgG1 was only detected for the A375 cells and none of the cells stained positively with the CMVscTCR/IgG1. These results confirm that the presence of the HLA-A2 and the p53 antigen are required for positive staining with the 264scTCR reagents. No background staining was seen with the non-specific CMVscTCR reagent in any of the tumor cell lines or with the 264scTCR reagent when the HLA-A2 and p53 antigen were not expressed.

Example 14

Quantitative Staining Using 264scTCR Fusion Proteins

The number of 264scTCR complexes capable of binding peptide-loaded T2 cells was determined T2 cells were incubated with various amounts of p53 (aa264-273) for 3 hours and then washed twice with washing buffer. Cell staining was carried out using 3.7 µg 264scTCR/BirA-streptavidin-PE tetramers for 45 minutes at 23° C. After washing twice, the stained cells were resuspended and analyzed on a FACScan. Alternatively, cell staining was carried out using 3.76 µg 264scTCR/IgG1 fusion protein for 45 minutes at 23° C. The cells were washed once and stained with 3 µg PE-conjugated anti-human IgG antibody. After washing twice, the stained cells were resuspended and analyzed on a FACScan.

Figure 14:
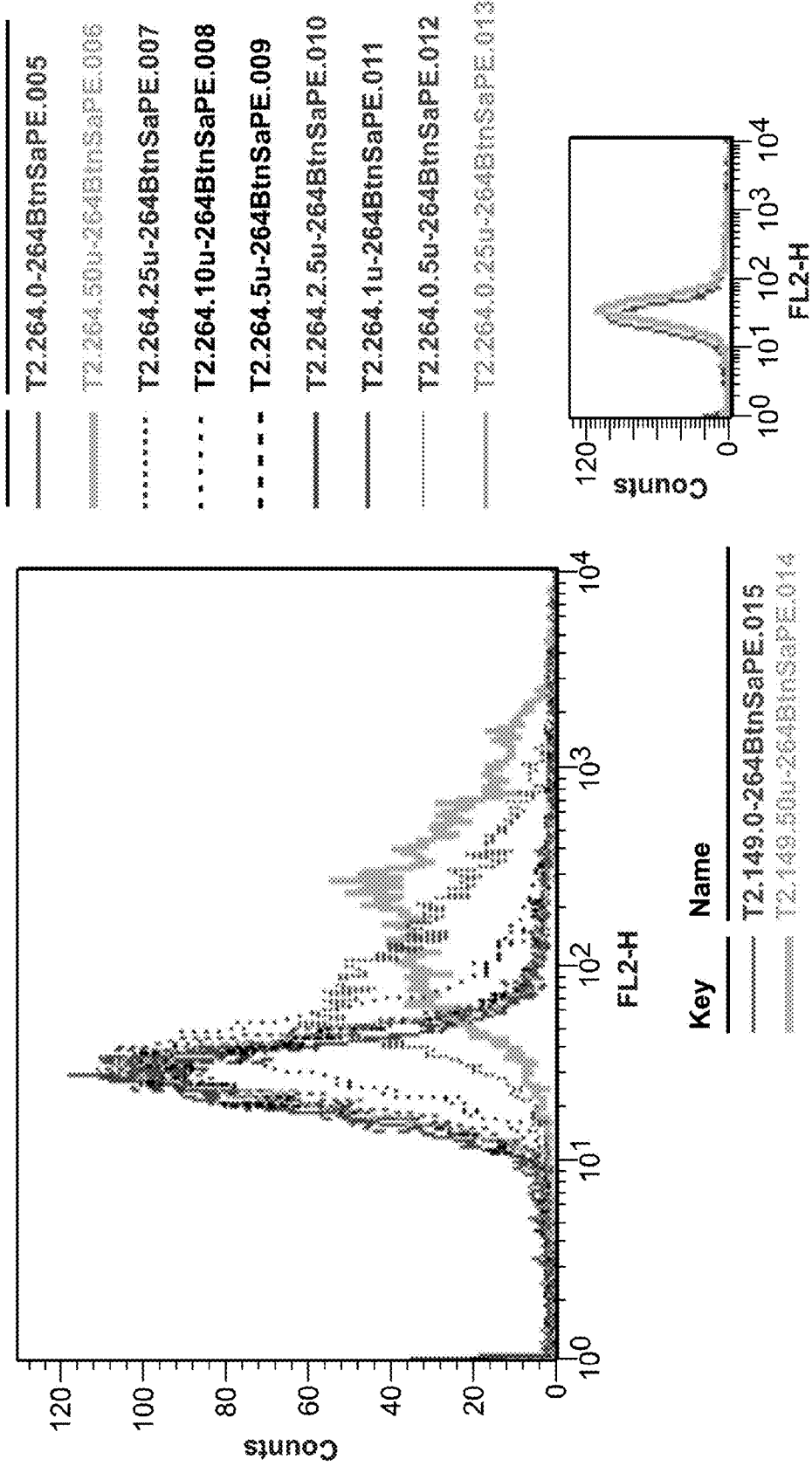
FIG. 14 is a graph showing quantitative staining of T2 cells reacted with 264scTCR/BirA tetramers.
Figure 15:
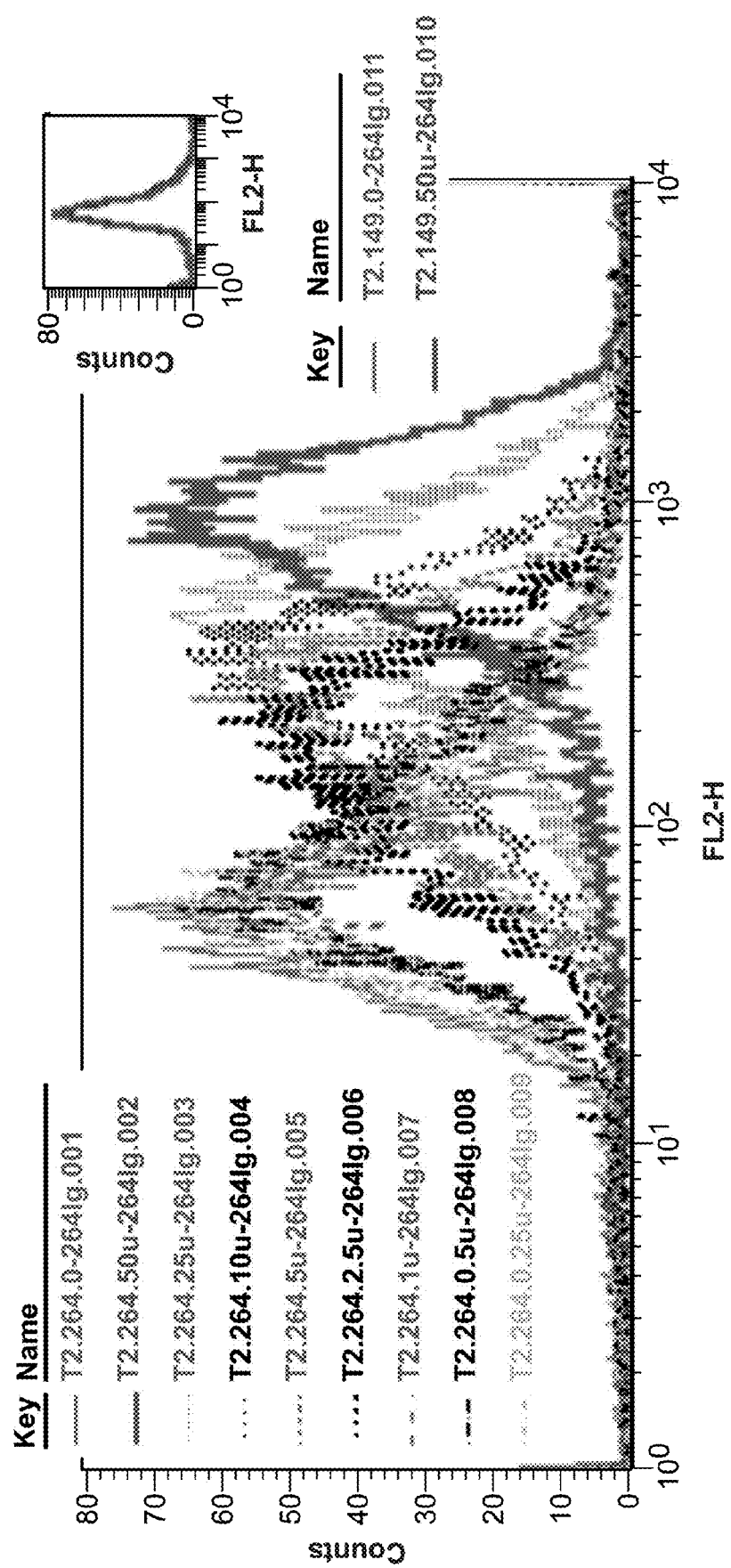
FIG. 15 is a graph showing quantitative staining of T2 cells reacted with 264scTCR/IgG1 fusion protein.

The results of this analysis are shown in FIG. 14 for 264scTCR/BirA tetramers, and in FIG. 15 for 264scTCR/IgG1 fusions. Increasing level of staining with increasing amount of p53 peptide was observed for both the 264scTCR/BirA tetramers and the 264scTCR/IgG1 fusions. To quantitate the number of complexes staining the cells, the level of fluorescence intensity on stained cells was compared with the fluorescence intensities of calibration beads having known numbers of PE molecules per bead (QuantiBRITE PE beads; BD Biosciences), thus providing a means of quantifying PE-stained cells using a flow cytometer.

Figure 16:
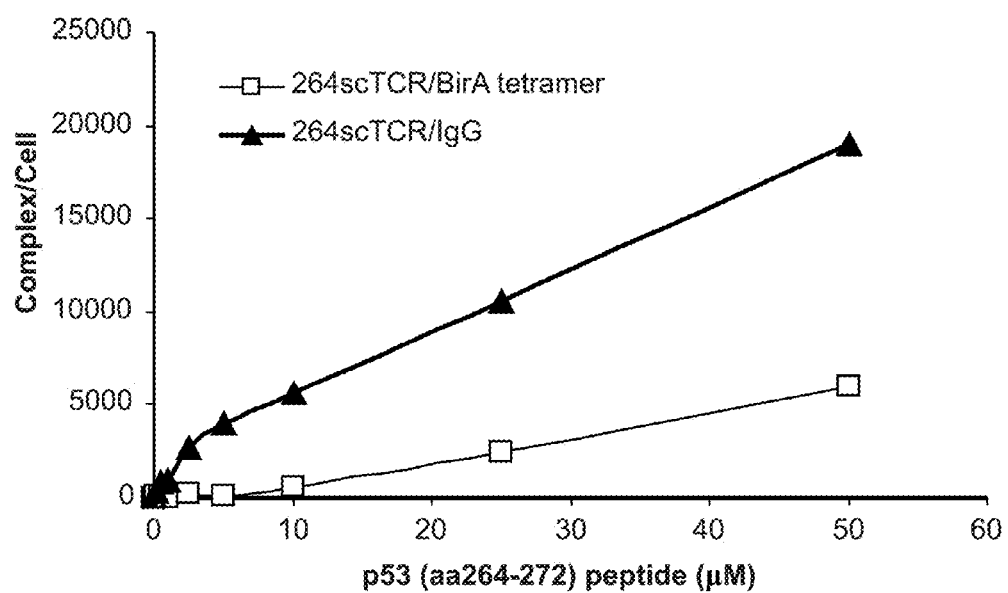
FIG. 16 is a graph showing numbers of complexes per cell with increasing amounts of loaded p53 peptide, for cells reacted with 264scTCR/BirA tetramer or 264scTCR/IgG fusions.

The calculated number of complexes/cell with various concentrations of peptide for the 264scTCR/BirA tetramers and the 264scTCR/IgG1 fusions are plotted in FIG. 16. The results show that the binding of as few as 400 scTCR complexes could be detected on the stained cells. In addition, staining with the 264scTCR/IgG1 fusion followed by PE-conjugated anti-human IgG antibody gave about a 4-10 fold increase in staining compared to that seen with the 264scTCR/BirA tetramers. This increase is possibly the result of a higher level of PE conjugation to the antibody and/or multiple antibodies reacting with the same 264scTCR/IgG1 fusion.

From the foregoing it will be appreciated that methods such as those described above to quantitatively detect TCR binding will be beneficial in optimizing the detection of rare antigens. The methods were applied to detect 264scTCR reagent binding to tumor cells. Cells were prepared as described and stained with various amounts of 264scTCR/BirA-streptavidin-PE tetramers for 45 minutes at 23° C. After washing twice, the stained cells were resuspended and analyzed on a FACScan. Alternatively, cell staining was carried out with various amounts of 264scTCR/IgG1 fusion protein for 45 minutes at 23° C. The cells were washed once and stained with 2.5 µg PE-conjugated H57 antibody. After washing twice, the stained cells were resuspended and analyzed on a FACScan.

Figure 17B:
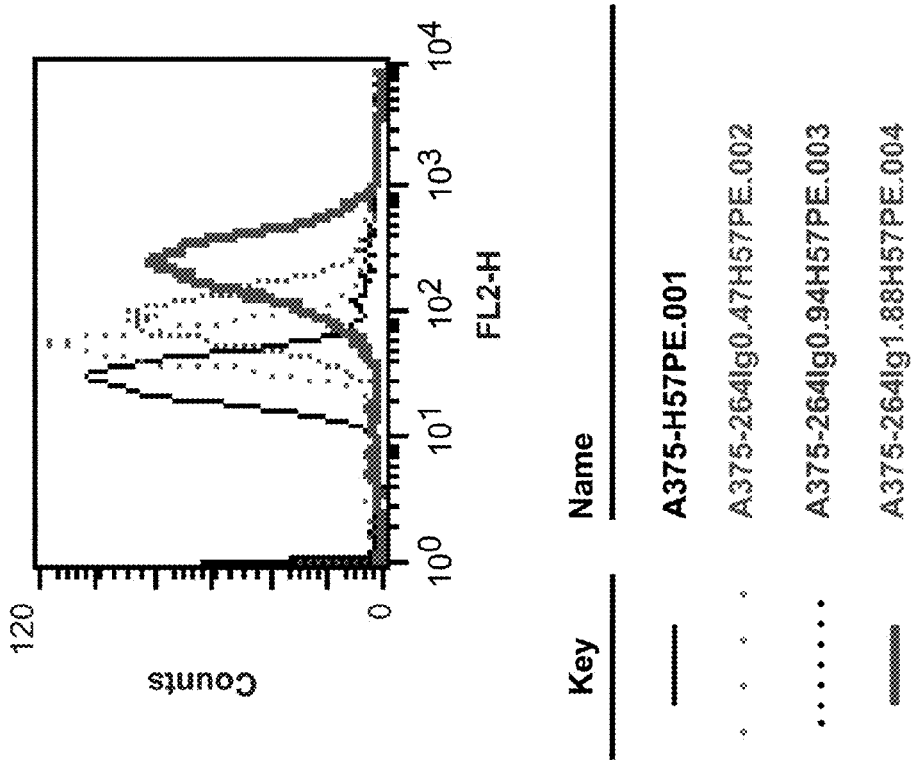
FIG. 17A and FIG. 17B are graphs showing quantitative staining of A375 tumor cells reacted with 264scTCR/BirA tetramers (FIG. 17A) or 264scTCR/IgG1 fusion protein (FIG. 17B).
Figure 17A:
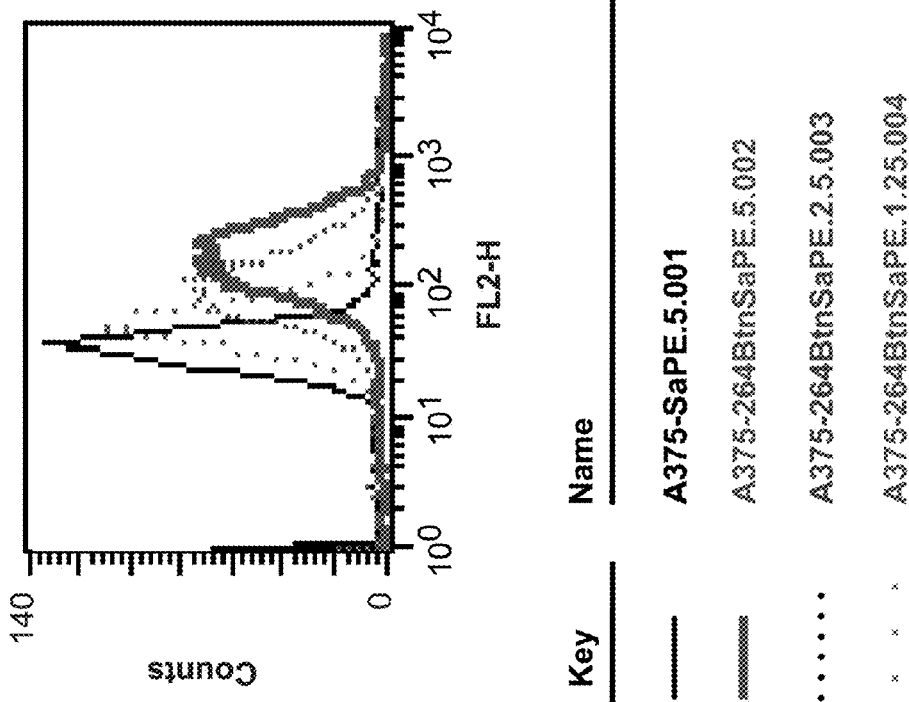
Figure 18:
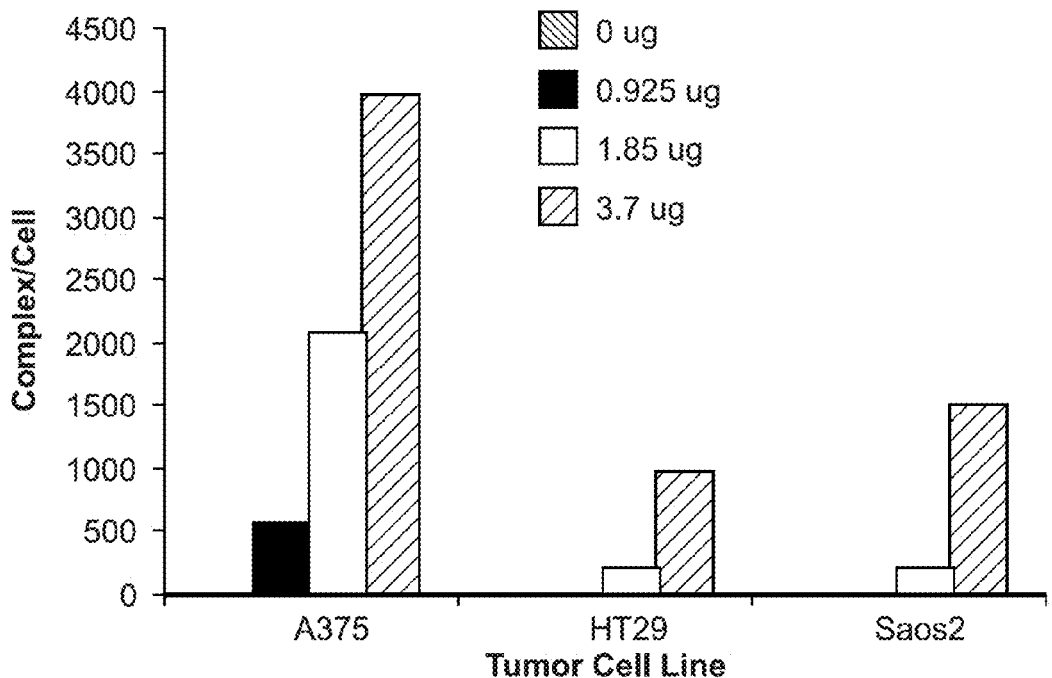
FIG. 18 is a graph showing quantitative staining (number of complexes per cell) of three tumor cell lines reacted with 264scTCR/BirA tetramers.
Figure 19:
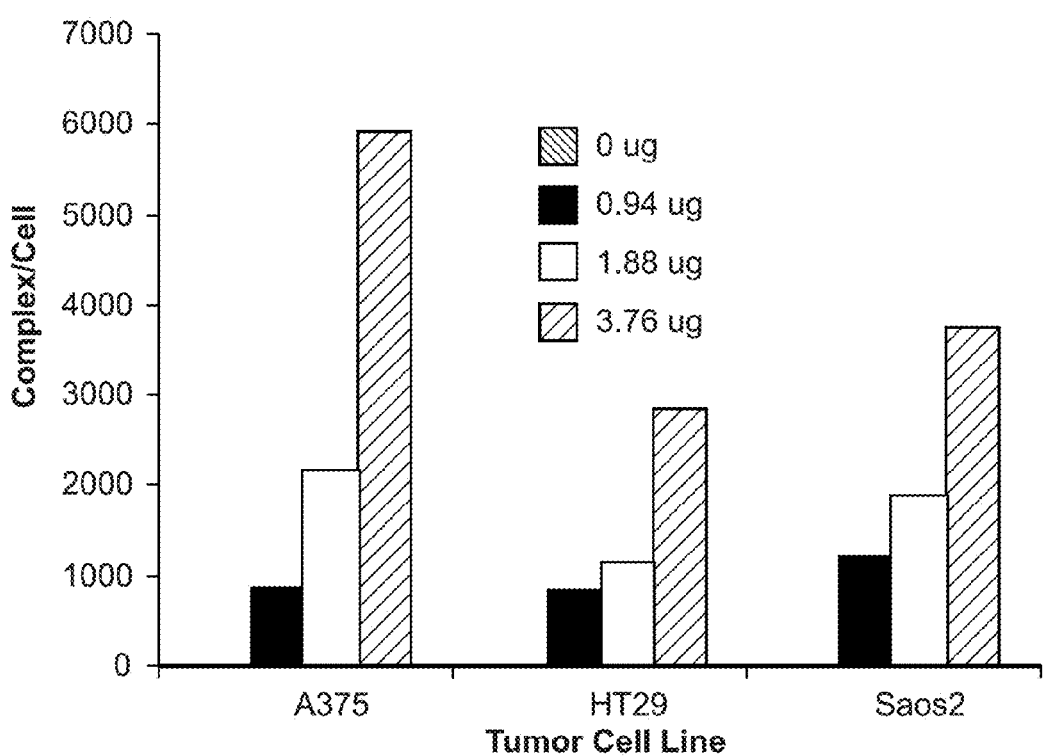
FIG. 19 is a graph as in FIG. 18 showing quantitative staining of three tumor cell lines reacted with 264scTCR/IgG1 fusion protein.

In each case, the number of complexes staining the cells was determined by comparing the level of fluorescence intensity on stained cells with the fluorescence intensities of calibration beads with known numbers of PE molecules per bead. FIGS. 17A and 17B show staining of A375 tumor cells with the increasing amounts of 264scTCR reagents. FIGS. 18 and 19 respectively show the quantitation of the staining observed for three tumor cell lines (A375, HT29 and Saos2) with the increasing amounts of 264scTCR/BirA and 264scTCR/IgG1 reagents. The HLA-A2/p53 positive A375 tumor cell line stained with both reagents and bound 2-5 fold more 264scTCR reagent than the HT29 (HLA-A2-negative) and Saos2 (p53-negative) cell lines. In addition, specific staining of the A375 cells increased as the amount of 264scTCR reagent was increased. Differential detection of as few as 500 staining complexes could be determined by comparing the staining of the A375 cells with that of other tumor cell lines. The results of these quantitative staining studies indicate that specific binding of the 264scTCR reagents to as few as 300-500 HLA-A2/peptide complexes per cell can be readily detected. In addition, the sensitivity of these staining reactions could be increased and optimized with the use of different TCR and secondary reagents.

Example 15

Immunohistochemical Staining of Unmanipulated Tumor Tissue by 264scTCR Fusion Proteins To produce subcutaneous tumors, A375 human melanoma cells ($1\times10^6$) were injected subcutaneously into the left shoulder of nude mice. Tumors were allowed to grow to 500 $mm^3$ and the mice were humanely sacrificed. Tumors were excised with overlying skin and fixed overnight in neutral buffered formalin. For production of metastatic lung nodules, MDA-MB-231 cells ($1\times10^6$) were injected into the lateral tail vein of nude mice, and metastatic lung nodules were allowed to develop. After 18 days, mice were humanely sacrificed, and the lungs were removed and fixed in neutral buffered formalin. Fixed tissue was dehydrated by sequential 30 minute incubations in 70%, 90%, 95%, 100% (twice) ethanol followed by two 30 minute incubations in xylene. Tissues were then embedded in paraffin and 5 µm sections were prepared and mounted on microscope slides.

For immunohistochemical staining, sections were rinsed twice for five minutes each in xylene followed by rehydration in sequential incubations in 100% (twice), 95%, and 85% ethanol for two minutes each. After two 5 minute washes with PBS and one 5 minute wash with the distilled water, slides were incubated in 3% $H_2O_2$ for 5 minutes to deactivate endogenous peroxidases followed by one five minute wash in the distilled water. Slides were placed in antigen retrieval solution (Dako) and heated to 97° C. for 20 minutes. The slides were allowed to cool in the antigen retrieval solution at room temperature for 20 minutes followed by two five minute washes in PBS.

If using a non-HRP labeled secondary reagent, slides were incubated in avidin/biotin blocking solution (ten minutes in each solution) followed by two five-minute washes in PBS. Slides were blocked in 1% normal goat serum (NGS) in PBS for 30 minutes at room temperature. This blocking step is necessary to reduce background staining due to non-specific interaction of the secondary goat antibody reagent. The slides were then incubated for 45 minutes at room temperature in the presence or absence of 10 µg (per 100 µl in 1% NGS) 264scTCR/IgG1 fusion protein or control CMVscTCR/IgG1 fusion protein. After two five minute washes in PBS, slides were incubated in 1.6 µg (per 200 µl in 1% NGS) HRP-labeled F(ab')$_2$ fragment of goat anti-human IgG Fcγ for 45 minutes at room temperature. Slides were washed twice for five minutes each with PBS. Slides were incubated in DAB solution (Dako) until a light background appeared. Slides were rinsed in tap water and counterstained in hematoxylin for 15 seconds. After washing with tap water, slides were rinsed in three baths of 100% ethanol and three baths of xylene for 3 minutes each and then mounted with Permount (Fisher). The level of tissue staining was assessed by light microscopy and documented with a SPOT RT camera and SPOT RT software v3.2 (Diagnostic Instrument, Sterling Heights, Mich.).

Figure 20:
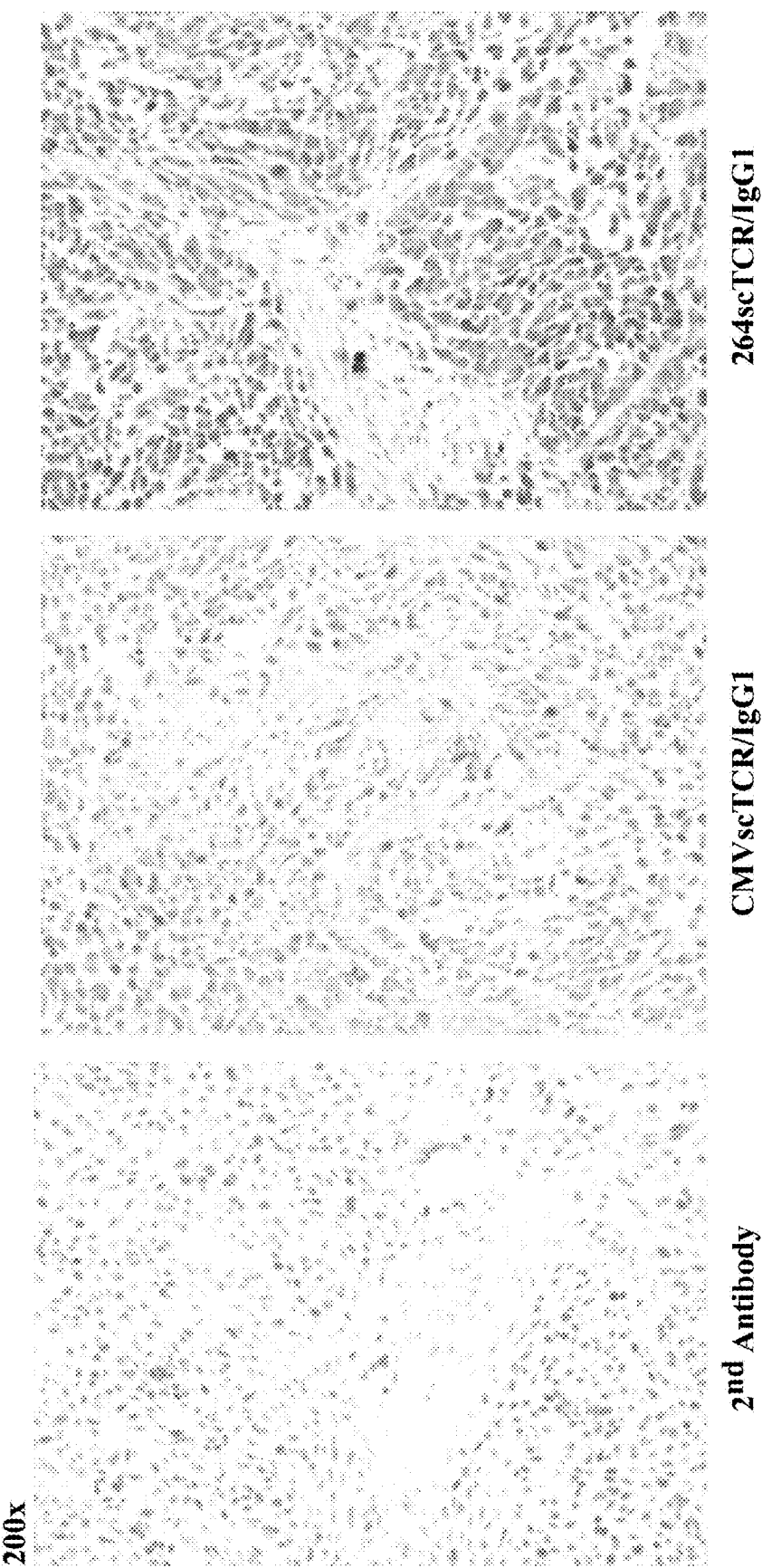
FIG. 20 is three photomicrographs showing fixed sections of A375 tumor stained with secondary antibody, CVM-scTCR/IgG1 (control) or 264TCR/IgG1 fusion protein, at 200×.
Figure 21:
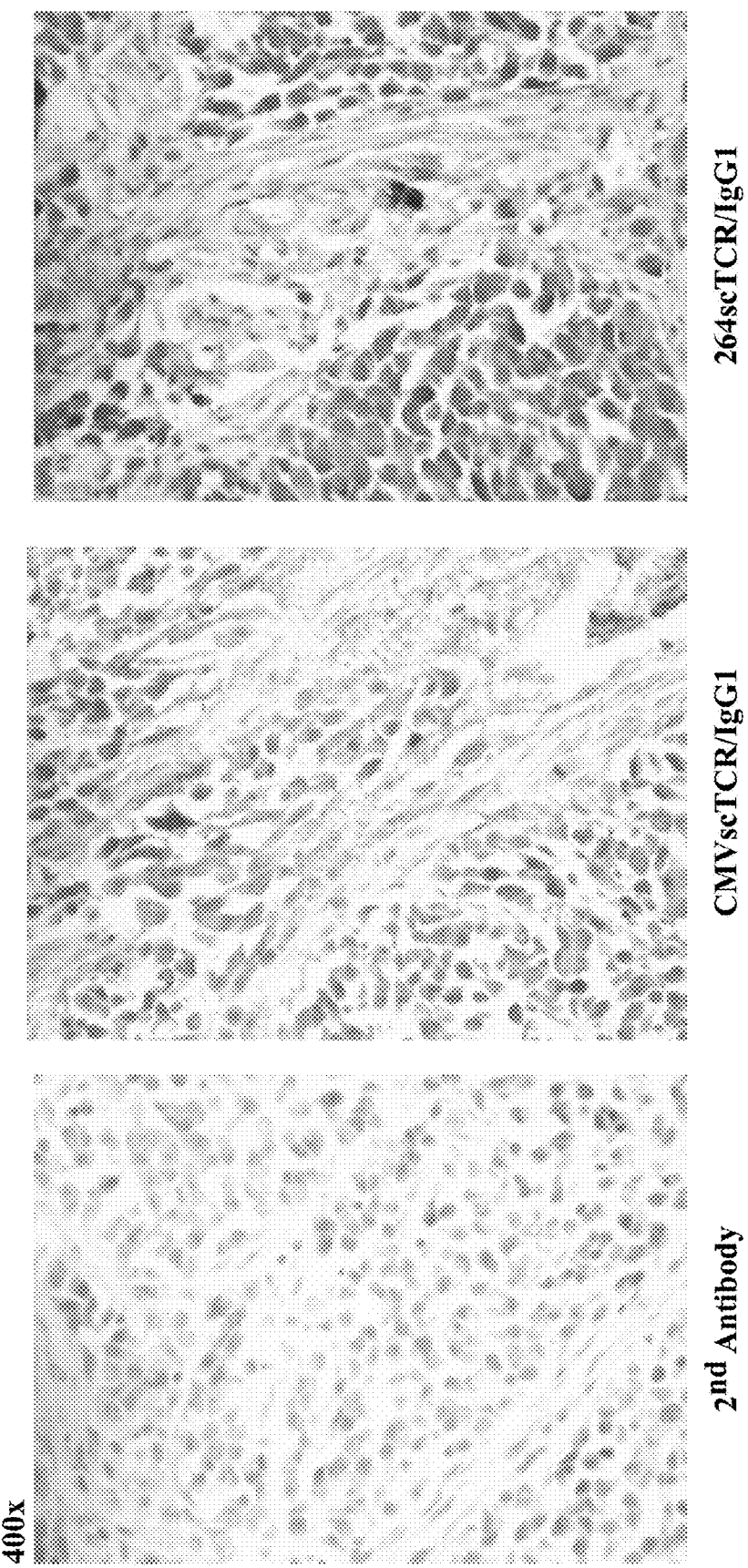
FIG. 21 is three photomicrographs showing tumor sections as in FIG. 20, at higher magnification (400×).

A typical immunohistochemical analysis using A375 tumor sections is shown in FIGS. 20 and 21. The results showed that A375 tissue sections stained much more intensely (i.e., appeared more darkly colored) when incubated with 264scTCR/IgG1 fusion protein compared to the CMVscTCR/IgG1 fusion protein or the secondary antibody alone. The background staining observed with the CMVscTCR/IgG1 fusion protein is comparable to that seen following incubation with a human IgG1 antibody followed by HRP-labeled anti-human IgG antibody, indicating that the background staining is likely due to interaction of the IgG1 domain with the tissue sections. In addition, staining of the mouse stromal tissue by the 264scTCR/IgG1 fusion protein was considerably less than that seen in the A375 tumor tissue present in the same section. These results indicate that the 264scTCR reagent is capable of specifically staining fixed human tumor tissue sections by immunohistochemical methods typically used to characterize human tumor samples.

Example 16

Immunohistochemical Staining of Tumor Histoarrays with 264scTCR Fusion Proteins

Human tumor histoarrays are obtained from commercial sources or from the Tissue Array Research Program (NCI). For staining, the histoarray slides are rinsed twice for five minutes each in xylene followed by rehydration in sequential incubations in 100% (twice), 95%, and 85% ethanol for two minutes each. After two 5 minute washes with PBS and one 5 minute wash with the distilled water, slides are incubated in 3% $H_2O_2$ for 5 minutes to deactivate endogenous peroxidases, followed by one five minute wash in the distilled water. Slides are placed in antigen retrieval solution (Dako) and heated to 97° C. for 20 minutes. The slides are allowed to cool in the antigen retrieval solution for 20 minutes followed by two five-minute washes in PBS. If using a non-HRP labeled secondary reagent, slides are incubated in avidin/biotin blocking solution (ten minutes in each solution) followed by two five minute washes in PBS. Slides are blocked in 1% normal goat serum (NGS) in PBS for 30 minutes at room temperature and then incubated for 45 minutes at room temperature in the presence or absence of 264scTCR/IgG1 fusion protein or CMVscTCR/IgG1 fusion protein (or other non-binding scTCR reagent). After two five minute washes in PBS, slides are incubated in secondary reagent (either HRP-labeled goat anti-human IgG or biotinylated anti-TCR Cβ antibody) for 45 minutes at room temperature. Slides are washed twice for five minutes each with PBS.

If a non-HRP secondary reagent is used, slides are incubated with streptavidin peroxidase solution for 15 minutes at room temperature followed by two five minute washes with PBS. Alternatively, scTCR/BirA-streptavidin peroxidase reagents are used as staining reagents in place of the reagents described above.

Slides are incubated in DAB solution (Dako) until a light background appears. Slides are rinsed in tap water and counterstained with hematoxylin for 15 seconds. After washing with tap water, slides are rinsed in three changes of 100% ethanol and three changes of xylene and then mounted with Permount (Fisher). The level of tissue staining is assessed by light microscopy and photographed, for example with a SPOT RT camera and SPOT RT software v3.2 (Diagnostic Instrument, Sterling Heights, Mich.).

Tumors that express HLA-A2 and p53 are expected to be differentially stained when incubated with the 264scTCR fusion protein compared to the CMVscTCR fusion protein. Little or no staining is expected when the histoarrays are incubated with no fusion protein. In addition, tumor tissues that are negative for HLA-A2 and/or p53 are expected to show reduced staining with 264scTCR fusion protein compared to HLA-A2/p53-positive tumor tissue. This can give useful information about what types of tumors, and the relative proportions thereof, that can be recognized by 264scTCR fusion proteins, aiding decisions about the advisability of treating a given type of tumor with a 264scTCR based therapy.

Example 17

Imaging of Tumors In Vivo with Fluorescent TCR Reagents

Expression vectors are constructed to generate 264scTCR fused to GFP (green fluorescent protein) or Luc (firefly luciferase). These vectors can be generated from the 264scTCR/IgG1 expression vector described herein by replacing the IgG1 gene fragment with GFP or Luc coding sequences. Sources of these coding sequences are commercially available (for example, pEGFP-C1 (Clontech) for the GFP gene, and pSP-Luc (Promega) for the Luc gene. The vectors are used as a template to isolate the appropriate DNA sequence by standard PCR methods. Expression vectors for control TCR (i.e., CMVscTCR) fusions to GFP and Luc can be generated by the same methods. In some applications these expression vectors can be used to transfect cells such as CHO cells and the resulting expressed proteins are purified as described herein.

These purified proteins are used to image tumors in vivo. Human tumor cells that vary with respect to HLA-A2 and p53 expression are implanted either subcutaneously or intravenously and tumors or metastatic lung nodules are allowed to develop as described in Example 15 above. For the scTCR/Luc fusions, mice are injected intravenously with increasing amounts of the scTCR/Luc fusion proteins. After a period of time necessary to allow the fusion proteins to circulate throughout the body, the mice are injected intraperitoneally with 2.0 mg D-luciferin substrate for luciferase in 100 µl PBS, then anesthetized with xylazine (3 mg/ml) and ketamine (7 mg/ml) in PBS at 120 µl/20 g body weight. For the scTCR/GFP fusions, mice are injected intravenously with increasing amounts of the scTCR/Luc fusion proteins. After a period of time necessary to allow the fusion proteins to circulate throughout the body, the mice anesthetized with xylazine (3 mg/ml) and ketamine (7 mg/ml) in PBS as described above.

For tumor detection in vivo, anesthetized mice are placed inside a NightOwl LB 981 Molecular Light Imager. Imaging is performed using a two-step process and WinLight software (Berthold Technologies, Oak Ridge Tenn.). First, a black and white photographic image is acquired using a 15 ms exposure followed by luminescent image acquisition using a 5-minute photon integration period with background subtraction. The luminescent image is processed in the software to colorize the luminescence intensity and then overlaid onto the black and white photographic image for presentation. In some cases mice are sacrificed and pathological assessment is performed to determine the size, location and nature (i.e., antigen positivity or negativity) of the tumors.

Results from imaging studies demonstrating differential detection of the 264scTCR/Luc or 264scTCR/GFP reagents at tumor sites bearing HLA-A2/p53 positive tumor cells compared with other tissues indicate scTCR reagents capable of specifically detecting tumors in vivo.

Additionally, results demonstrating differential detection of the 264scTCR/Luc or 264scTCR/GFP reagents at tumor sites bearing HLA-A2/p53 positive tumor cells compared with that of the CMVscTCR/Luc or CMVscTCR/GFP (control) reagents would further indicate those scTCR reagents capable of specifically detecting tumors in vivo. Imaging results demonstrating differential detection of the 264scTCR/Luc or 264scTCR/GFP reagents at tumor sites bearing HLA-A2/p53 positive tumor cells compared with results for tumor sites bearing HLA-A2-negative or p53-negative tumor cells further indicate those scTCR reagents are capable of specifically detecting tumors in vivo.

Example 18

Imaging of Tumors In Vivo with Radiolabeled TCR

In another embodiment, 264scTCR fusion proteins are radiolabeled, for example by direct iodination with $^{131}$I. Iodination is carried out using standard methods. Human tumor cells that vary with respect to HLA-A2 and p53 expression are implanted either subcutaneously or intravenously and tumors or metastatic lung nodules are allowed to develop as described. Mice are injected intravenously or intraperitoneally with radiolabeled 264scTCR fusion protein and imaged for example at 1, 2, 4, 8, and 12 hours and 1 to 14 days after injection of radiolabeled 264scTCR fusion protein. For whole body scans, mice are anesthetized with 100 mg/kg sodium pentobarbital and imaged for example with a large field-of-view Sopha DSX camera fitted with a 4 mm pinhole collimator interfaced to a microcomputer. Results from imaging studies demonstrating differential detection of the radionucleotide-labeled 264scTCR reagents at tumor sites compared with other tissue would indicate those radiolabelled scTCR reagents useful for specifically detecting tumors in vivo.

The following materials and methods were used as needed to conduct experiments outlined in the Examples.

1. Materials

A2.1 264 CTL clone #5 was derived by limiting dilution cloning [50] from a CTL line specific for the human p53 264-272 peptide generated in HLA-A2.1 transgenic mice [49]. CHO.K1 Chinese hamster ovary, Jurkat human T lymphocyte, CTLL-2 mouse cytotoxic T lymphocyte, T2 human lymphoblast, A375 human melanoma, H57-597 hybridoma, and BB7.2 hybridoma cell lines were obtained from American Type Culture Collection (Rockville, Md.). The T2 human lymphoblast cells are positive for HLA-A2.1 but deficient in TAP 1 and 2 proteins, which allows them to display empty MHC molecules that can then be loaded with exogenous peptide [2]. The A375 human melanoma cell line was tested in our laboratory for both HLA-A2.1 and p53 and was found to be positive for both antigens. The H57-597 hybridoma produces a monoclonal antibody that recognizes an epitope in the murine TCR β constant region, and the BB7.2 hybridoma produces the BB7.2 monoclonal antibody that specifically recognizes an epitope on the alpha 2 domain of HLA-A2. The highly metastatic subclone of the human melanoma cell line A375, A375-C15N, which was used only for in vivo metastasis studies was maintained as previously reported [53]. Recombinant human IL-2 and biotinylated anti-human IL-2 polyclonal antibodies used for the ELISA in the pharmacokinetic study were purchased from R&D Systems, Inc. (Minneapolis, Minn.). Anti-TCR Cβ mAb H57-597, anti-murine TCR Vβ3 mAb, anti-murine CD3ε mAb, anti-human IL-2 mAb, anti-human CD25 blocking antibody and isotype control antibody, and FITC labeled goat anti-mouse IgG were obtained from Pharmingen (San Diego, Calif.). All cell culture media and additives were purchased from CellGro (Herndon, Va.), and all cell culture materials were purchased from Nunc (Rochester, N.Y.) unless otherwise noted. All mice were purchased from Harlan Labs (Indianapolis, Ind.).

2. Cell Culture

All cell lines were maintained in complete culture medium comprised of IMDM supplemented with 10% heat inactivated FBS, 2 mM L-glutamine, and 1 mg/ml G418 (for transfected CHO cells only) at 37° C. and 5% $CO_2$. CTLL-2 cells were maintained in the same medium with the addition of 9 U/ml recombinant human IL-2. A375-C15N cells were maintained in RPMI-1640 with 10% heat inactivated FBS, penicillin and streptomycin (Life Technologies).

Mouse splenocytes were isolated by pressing spleens aseptically dissected from BALB/c mice through a nylon mesh screen and washing with culture medium. Red blood cells were lysed with Gey's solution for 2 minutes followed by addition of culture medium to stop the lysis. Single cell pellets were washed twice, resuspended at $2.5 \times 10^6$ cells per mL in culture medium and cultured in complete culture medium containing 50 µM 2-ME, 100 IU/mL recombinant human IL-2, and 50 ng/ml anti-murine CD3e mAb.

3. Constructs

Primers—Oligonucleotide primers were synthesized from sequences matching or complementing the mouse T cell receptor and human IL-2 genes:

KC228:
(SEQ ID NO: 3)
5'-GAGGTGGCCCAGCCGGCCATGGCCCAGTCAGTGACGCAGC-3';

KC229:
(SEQ ID NO: 4)
5'-GAGGTGACTAGTGTCTGGCTTTATAATTAG-3';

PRIB4:
(SEQ ID NO: 5)
5'-GGGGGGCTCGAGCAATTCAAAAGTCATTCAGACTC-3';

KC176:
(SEQ ID NO: 6)
5'-GAGGTGGAGCCCGGGGTCTGCTCGGCCCCAGGC-3';

ET-TCRF1:
(SEQ ID NO: 7)
5'-CCCACCGGTCAGTCAGTGACGCAGCCC-3';

KC-170:
(SEQ ID NO: 8)
5'-GTGGAGTTCGAAAAGGTGACTTACGTTTGTCTGCTCGGCCCCAG-3';

KC231:
(SEQ ID NO: 9)
5'CGATAAGTGTACTTACGTTTTCATTATTCCATCGGCATGTACT
CTTCTTCCTCTCG-3';

KC208:
(SEQ ID NO: 10)
5'GTGGAGATCGATAAGTGTACTTACGTTTTCATTATCGCGATCCG
GAGTTAACGTCTGCTCGGCCCCAG-3';

KC327B:
(SEQ ID NO: 11)
5'-TAGGTGTCCGGAGCACCTACTTCAAGTTCTAC-3';

KC328B:
(SEQ ID NO: 12)
5'-TAGGTGTCGCGAAGTTAGTGTTGAGATGATG-3';

AP2:
(SEQ ID NO: 13)
5'-ACTCACTATAGGGCTCGAGCGGC-3';

Cα HYB:
(SEQ ID NO: 14)
5'GCTGTCCTGAGACCGAGGATCTTTTAACTG-3';

Cβ HYB:
(SEQ ID NO: 15)
5'-TTGTTTGTTTGCAATCTGTGCTTTTGATGG-3'.

The TCR gene was cloned from the T cell clone A2.1 264#5. We designate the single-chain TCR derived from this T cell clone 264scTCR. Poly(A)+ RNA was extracted from the cells using a MicroFast Track kit (Invitrogen, Carlsbad, Calif.), and double stranded cDNA was prepared and ligated to a double stranded adaptor oligonucleotide using the Marathon cDNA Amplification Kit (Clontech, Palo Alto, Calif.). To identify the Vα and Vβ segments, 5'-RACE PCR was performed using the A2.1 264#5 cDNA preparation and above-listed primers AP2 (specific for the adaptor DNA) and Cα HYB (specific for the constant domain of the α chain) or Cβ HYB (specific for the constant domain of the β chain). PCR fragments were cloned into the pCR2.1 vector using the TA cloning kit (Invitrogen), and the sequence was determined using M13 forward and reverse primers. The T cell receptor Vα chain was amplified using primers KC228 and KC229 to produce an SfiI/SpeI fragment, and the VβCβ chain was amplified using primers PRIB4 and KC176 to generate an XhoI/XmaI fragment. The Cβ chain was truncated just before the cysteine residue at amino acid 127 of the full length Cβ chain. The SfiI/SpeI Vα chain fragment was subcloned into SfiI/SpeI digested pKC60, an *E. coli* expression vector that encodes an irrelevant TCR, replacing the original TCR insert. The XhoI/XmaI VβCβ fragment was then ligated into an XhoI/XmaI digest of this vector yielding a vector encoding a soluble three domain 264scTCR. The three domain T cell receptor from this construct was amplified using primers ET-TCRF1 and KC170 to generate an AgeI/ClaI DNA fragment, which was then used as a template for PCR with primers KC231 and KC208 to produce an AgeI/HpaI fragment.

The human IL-2 coding sequence was cloned by RT-PCR from total RNA isolated from Jurkat cells using a Mini Total RNA Kit (Qiagen, Valencia Calif.) and Qiashredder (Qiagen, Valencia Calif.). Reverse transcription was carried out using primer KC328B, and PCR was carried out using primers KC327B and KC328B to produce a BspEI/NruI human IL-2 fragment. The BspEI/NruI IL-2 fragment was cloned into BspEI/NruI digested p149B1SP, a cloning vector encoding an irrelevant TCR/antibody fusion protein, replacing the antibody portion of the fusion protein. The IL-2 modified vector was digested with AgeI and HpaI and the AgeI/HpaI 264scTCR fragment described above was ligated into it. Finally, an AgeI/ClaI 264scTCR/IL-2 fusion protein fragment was cloned into AgeI/BstBI digested pSUN27, a scTCR/mouse kappa fusion vector, replacing the irrelevant TCR originally cloned in the vector, yielding the 264scTCR/IL-2 fusion protein expression vector, pSUN38. The 264scTCR/kappa fusion used as a negative control for some of the flow cytometry analyses was generated by cloning an AgeI/BstBI 264scTCR fragment into AgeI/BstBI digested pSUN27, replacing the original TCR.

For production of fusion protein in mammalian cells, CHO.K1 cells were electroporated using a Bio-Rad Gene Pulser, followed by limiting dilution cloning and selection in medium containing 1 mg/mL G418.

4. Protein Purification

264scTCR/IL-2 was purified from cell culture supernatant fluid by immunoaffinity chromatography using the monoclonal anti-murine TCR antibody H57-597, which recognizes an epitope in the constant region of the TCR β chain, coupled to a Sepharose 4B column (Amersham Pharmacia, Piscataway, N.J.). The purified sample was then concentrated and buffer-exchanged into PBS using an Ultrafree-15 centrifugal filter with a 30 kDa molecular weight cutoff membrane (Millipore, Bedford, Mass.). The TCR fusion protein samples were stored at 2-8° C. (short term) or at −80° C. (long term) for biochemical and functional analysis. SDS-PAGE was performed under either reducing or non-reducing conditions using 4-12% Nu-PAGE polyacrylamide gels (Novex, San Diego, Calif.) and the Novex EX-Cell II system. SDS-PAGE gels were stained with Coomassie blue.

5. ELISA

All ELISAs were performed using Maxisorb 96 well plates (Nunc, Rochester, N.Y.) coated with 100-200 ng/well anti-human IL-2 mAb or anti-murine TCR Vβ3 mAb. Fusion protein was detected with biotinylated anti-murine TCR H57 mAb, anti-murine TCR Vβ3 mAb, or anti-IL-2 polyclonal Ab followed by streptavidin-HRP (Kirkegaard and Perry Laboratories, Gaithersburg, Md.), TMB substrate, and 0.18 M $H_2SO_4$ to quench the reaction (BioFX, Owings Mills, Md.). Absorbance was measured at 450 nm using a 96 well plate reader (Bio-Tek Instruments, Inc., Winooski, Vt.).

6. Cell Staining with TCR Fusion Proteins

T2 cells pulsed with either p53 (aa 149-157) or p53 (aa 264-272) peptide were incubated with 0.5 μg of 264scTCR/IL-2 fusion protein in 1% FBS in PBS for 30 minutes at room temperature. The cells were then incubated with 0.5 μg anti-IL-2 Ab or 0.5 μg biotinylated anti-TCR H57-597 mAb for 30 minutes at room temperature followed by 1 μg anti-murine kappa-PE or 5 ng streptavidin-PE, respectively (both from Becton Dickenson, Franklin Lakes, N.J.). Samples were washed with 1% FBS in PBS before FACScan analysis (Becton Dickenson, Franklin Lakes, N.J.). To determine if both p53 peptides bound to HLA-A2 similarly, peptide loaded cells were stained with BB7.2 for 30 minutes at room temperature followed by FITC labeled goat anti-mouse IgG and analyzed on a FACScan instrument.

CTLL-2 cells were incubated with 0.5 μg of fusion protein for 30 minutes at room temperature. To detect the bound fusion protein, 0.5 μg biotinylated anti-TCR Vβ3 mAb was added and incubated for 30 minutes at room temperature followed by incubation with 5 ng streptavidin-PE, or the protein was detected using 0.5 μg PE-labeled HLA-A2.1 p53 (aa 264-272) tetramer for 30 minutes. Conjugated HLA-A2 tetramers loaded with p53 peptides were produced as described previously [1]. Samples were washed with 1% FBS in PBS before FACScan analysis. For IL-2 receptor blocking experiments, CTLL-2 cells were incubated with α-human CD25 blocking antibody or isotype control antibody for 30 minutes before incubation with 264scTCR/IL-2 or 264scTCR/kappa fusion protein. For staining of BALB/c mouse splenocytes, staining was carried out as described for the CTLL-2 cells using HLA-A2.1 p53 (aa 264-272) tetramers to detect bound fusion protein.

A375 cells were harvested with enzyme-free cell dissociation buffer (Sigma, St. Louis, Mo.). Samples of $5 \times 10^5$ cells were washed with 1% FBS in PBS and incubated with no fusion protein, 5 μg 3C8 (an irrelevant TCR/IL-2 fusion protein), or 5 μg 264scTCR/IL-2 for 30 minutes at room temperature followed by incubation with 1 μg biotinylated H57-597 mAb. Cells were then incubated with PE-labeled streptavidin for 15 minutes at room temperature, washed, and analyzed by FACScan.

7. Cell Conjugation

T2 cells pulsed with either p53 (aa 264-272) peptide or p53 (aa 149-157) peptide were labeled with 7.88 ng/ml dihydroethidium (HE) (Molecular Probes, Inc., Eugene, Oreg.), and CTLL-2 cells were labeled with 50 ng/ml calcein AM (Molecular Probes, Inc., Eugene Oreg.). After washing, the two populations of labeled cells were mixed together at a 1:1 ratio in the presence or absence of 2 μg 264scTCR/IL-2 fusion protein for 20 minutes at room temperature. Cells were then analyzed by FACScan.

8. Bioassay

CTLL-2 cells were seeded at $4 \times 10^3$ cells/well in 100 μl culture medium containing various concentrations of either recombinant IL-2 or 264scTCR/IL-2 and incubated for 21 hours at 37° C. and 5% $CO_2$. As a control for specificity CTLL-2 cells were incubated with 264scTCR/IL-2 in the presence or absence of 5 or 50 μg anti-human CD25 blocking antibody or isotype control antibody and incubated for 21 hours at 37° C. and 5% $CO_2$. Cell proliferation reagent WST-1 (Roche Inc., Indianapolis, Ind.) was added at 20 μl/well and incubated for 4 hours at 37° C. and 5% $CO_2$. Absorbance was read at 450 nm on a 96-well plate reader.

9. Pharmacokinetics in Mice

For all experiments involving animals, principles of laboratory animal care (NIH publication No. 85-23, revised 1985) were followed, as well as specific national laws where applicable. Female BALB/c mice were injected intravenously via the lateral tail vein with 32 μg 264scTCR/IL-2 fusion protein diluted with PBS to a total volume of 100 μl. Serum was collected from one group of mice not injected with 264scTCR/IL-2 to establish background levels. Serum was collected by tail bleed from the injected groups at 15 and 30 minutes, 1, 2, 4, 8, and 24 hours. Blood samples were centrifuged at 14,000×g at 4° C. for 10 minutes, and serum was collected and stored at −80° C. until use. 264scTCR/IL-2 concentrations were determined by ELISA using anti-TCR Vβ3 or anti-IL-2 monoclonal antibodies for capture and either biotinylated anti-TCR H57 monoclonal or anti-IL-2 polyclonal antibodies followed by streptavidin HRP for detection.

10. In Vivo Studies

Female athymic nude mice (nu/nu) were injected with 5.0×10⁵ A375-C15N cells via the lateral tail vein Animals were injected with varying doses of either 264scTCR/IL-2 (32, 10, 3, 1, or 0.1 µg in 100 µl total volume) or recombinant human IL-2 (8, 2.5, 0.75, 0.25, or 0.025 µg in 100 µl total volume) days 1, 2, 3, 4, 7, 10, 14, 17, 21, 28, and 35 post-tumor cell injection. Forty-two days after tumor cell injection, all animals were humanely sacrificed, the lungs were removed and fixed in Bouin's solution, and surface pulmonary tumor nodules were counted. Tumor nodules on each lung were counted by two observers and the average counts were recorded.

11. TCR Constructs and Fusion Proteins Comprising IgG and Bir A Tag Sequence

The TCR gene was cloned from the T cell clone A2.1 264#5 as described. The single-chain TCR derived from this T cell clone was designated as 264scTCR. The three domain single chain 264scTCR was amplified using a 264scTCR/IL-2 fusion protein construct as a template. To generate the 264scTCR/IgG1 expression construct, the single chain TCR fragment was ligated into an antibody heavy chain expression vector, replacing the antibody variable region and yielding a single chain TCR fused to a human IgG1 heavy chain region. To generate the 264scTCR/trunIgG1, the TCR fragment was ligated into an expression vector containing the IgG1 heavy domain that was truncated prior to the hinge region that allows disulfide bonding.

To generate the 264scTCR/BirA expression construct, the single chain TCR fragment was ligated into an expression vector containing the BirA tag sequence (Beckett, D. et al. Protein Sci. 1999 April; 8(4):921-9), such that the tag sequence was expressed in frame at the C-terminus of the 264scTCR molecule.

The Cytomegalovirus single-chain TCR (CMVscTCR) was cloned from CTLs stimulated with HLA-A2 restricted CMV-pp65 peptides. The IgG1 fragment was amplified from 264scTCR/IgG1 DNA to create the CMVscTCR/IgG1 construct.

For production of the fusion proteins in mammalian cells, CHO.K1 cells were electroporated using a Bio-Rad Gene Pulser, followed by limiting dilution cloning and selection in medium containing 1 mg/ml G418.

Protein purification was carried out as follows. 264scTCR/IgG1, 264scTCR/BirA and 264scTCR/trunIgG1 were purified from cell culture supernatant fluid by immunoaffinity chromatography using the H57-597 monoclonal antibody coupled to a Sepharose 4B column (Amersham Pharmacia, Piscataway, N.J.). CMVscTCR/IgG1 was purified from cell culture supernatant fluid by immunoaffinity chromatography using the BF1 monoclonal antibody coupled to a Sepharose 4B column (Amersham Pharmacia, Piscataway, N.J.). 264scTCR/BirA was biotinylated with biotin-protein ligase (Avidity) under conditions recommended by the manufacturer.

12. Detection of Cell Staining by 264scTCR Reagents by Flow Cytometry

The ability of 264scTCR reagents to stain fixed and unfixed cells was characterized in several studies. Cell staining strategies included use of 264scTCR fusions carrying various detectable domains, and detecting the cellular interaction of these fusions with various fluorescently labeled probes. Several controls were used to assess specific staining. Controls included staining cells that lacked the p53(aa264-273) antigen with the 264scTCR reagents, staining p53-positive cells with the CMVscTCR reagents, staining p53-positive cells with secondary staining reagents alone, and staining p53-positive cells with the 264scTCR reagents with and without competitive blocking reagents such as soluble HLA-A2/p53 multimers.

Monomeric or multimeric forms of the 264scTCR were tested for their ability to specifically stain cells. T2 cells were loaded with p53 (aa264-273) or p53 (aa149-157) at 100 µg/ml for 2.5 hour at 37° C. After a wash step to remove excess peptide, the cells were incubated with 264scTCR/IL-2, 264scTCR/IgG1, 264scTCR/trIgG1 or 264scTCR/BirA (without biotinylation) at 125 pM for 30-45 minutes. SDS-PAGE analysis of reduced and non-reduced samples indicated that the 264scTCR/trunIgG1 and 264scTCR/BirA proteins are monomeric and the 264scTCR/IgG1 protein is a dimer. After another wash step, cells were incubated for 30 minutes with 2.5 µg PE-conjugated H57 mAb (H57-PE). The cells were washed and analyzed on a FACScan flow cytometry instrument (BD Sciences, San Jose, Calif.) using CellQuest software (BD Biosciences, San Jose, Calif.). Unstained and H57-PE stained T2 cells were also analyzed to establish background staining.

The following documents are referred to (by a number as shown below) throughout the present disclosure. Each document is incorporated by reference.

1. Altman J D, Moss P A, Goulder P J, Barouch D H, McHeyzer-Williams M G, Bell J I, McMichael A J, Davis M M (1996) Phenotypic analysis of antigen-specific T lymphocytes. Science 274: 94
2. Anderson K S, Alexander J, Wei M, Cresswell P (1993) Intracellular transport of class I MHC molecules in antigen processing mutant cell lines. J Immunol 151: 3407
3. Bauer R J, Dedrick R L, White M L, Murray M J, Garovoy M R (1999) Population pharmacokinetics and pharmacodynamics of the anti-CD11a antibody hu1124 in human subjects with psoriasis. J Pharmacokinet Biopharm 27: 397
4. Becker J C, Varki N, Gillies S D, Furukawa K, Reisfeld R A (1996) Long-lived and transferable tumor immunity in mice after targeted interleukin-2 therapy. J Clin Invest 98: 2801
5. Chung S, Wucherpfennig K W, Friedman S M, Hafler D A, Strominger J L (1994) Functional three-domain single-chain T-cell receptors. Proc Natl Acad Sci USA 91: 12654
6. Donohue J H, Rosenberg S A (1983) The fate of interleukin-2 after in vivo administration. J Immunol 130: 2203
7. Dummer R, Gore M E, Hancock B W, Guillou P J, Grobben H C, Becker J C, Oskam R, Dieleman J P, Burg G (1995) A multicenter phase II clinical trial using dacarbazine and continuous infusion interleukin-2 for metastatic melanoma. Clinical data and immunomonitoring. Cancer 75: 1038
8. Engel I, Ottenhoff T H, Klausner R D (1992) High-efficiency expression and solubilization of functional T cell antigen receptor heterodimers. Science 256: 1318
9. Gregoire C, Rebai N, Schweisguth F, Necker A, Mazza G, Auphan N, Millward A, Schmitt-Verhulst A M, Malissen B (1991) Engineered secreted T-cell receptor alpha beta heterodimers. Proc Natl Acad Sci USA 88: 8077
10. Grimm E A, Mazumder A, Zhang H Z, Rosenberg S A (1982) Lymphokine-activated killer cell phenomenon. Lysis of natural killer-resistant fresh solid tumor cells by interleukin 2-activated autologous human peripheral blood lymphocytes. J Exp Med 155: 1823

11. Grussenmeyer T, Scheidtmann K H, Hutchinson M A, Eckhart W, Walter G (1985) Complexes of polyoma virus medium T antigen and cellular proteins. Proc Natl Acad Sci USA 82: 7952
12. Hank J A, Albertini M R, Schiller J, Sondel P M (1993) Activation of multiple effector mechanisms to enhance tumor immunotherapy. J Immunother 14: 329
13. Hank J A, Robinson R R, Surfus J, Mueller B M, Reisfeld R A, Cheung N K, Sondel P M (1990a) Augmentation of antibody dependent cell mediated cytotoxicity following in vivo therapy with recombinant interleukin 2. Cancer Res 50: 5234
14. Hank J A, Sosman J A, Kohler P C, Bechhofer R, Storer B, Sondel P M (1990b) Depressed in vitro T cell responses concomitant with augmented interleukin-2 responses by lymphocytes from cancer patients following in vivo treatment with interleukin-2. J Biol Response Mod 9: 5
15. Hank J A, Surfus J, Gan J, Chew T L, Hong R, Tans K, Reisfeld R, Seeger R C, Reynolds C P, Bauer M, et al. (1994) Treatment of neuroblastoma patients with antiganglioside GD2 antibody plus interleukin-2 induces antibody-dependent cellular cytotoxicity against neuroblastoma detected in vitro. J Immunother 15: 29
16. Harvill E T, Fleming J M, Morrison S L (1996) In vivo properties of an IgG3-IL-2 fusion protein. A general strategy for immune potentiation. J Immunol 157: 3165
17. Harvill E T, Morrison S L (1995) An IgG3-IL2 fusion protein activates complement, binds Fc gamma RI, generates LAK activity and shows enhanced binding to the high affinity IL-2R. Immunotechnology 1: 95
18. Hilyard K L, Reyburn H, Chung S, Bell J I, Strominger J L (1994) Binding of soluble natural ligands to a soluble human T-cell receptor fragment produced in *Escherichia coli*. Proc Natl Acad Sci USA 91: 9057
19. Hinds P W, Finlay C A, Quartin R S, Baker S J, Fearon E R., Vogelstein B, Levine A J (1990) Mutant p53 DNA clones from human colon carcinomas cooperate with ras in transforming primary rat cells: a comparison of the "hot spot" mutant phenotypes. Cell Growth Differ 1: 571
20. Hurford R K Jr, Dranoff G, Mulligan R C, Tepper R I (1995) Gene therapy of metastatic cancer by in vivo retroviral gene targeting. Nat Genet 10: 430
21. Huston J S, Levinson D, Mudgett-Hunter M, Tai M S, Novotny J, Margolies M N, Ridge R J, Bruccoleri R E, Haber E, Crea R, et al (1988) Protein engineering of antibody binding sites: recovery of specific activity in an antidigoxin single-chain Fv analogue produced in *Escherichia coli*. Proc Natl Acad Sci USA 85: 5879
22. Iggo R, Gatter K, Bartek J, Lane D, Harris A L (1990) Increased expression of mutant forms of p53 oncogene in primary lung cancer. Lancet 335: 675
23. Kendra K, Gan J, Ricci M, Surfus J, Shaker A, Super M, Frost J D, Rakhmilevich A, Hank J A, Gillies S D, Sondel P M (1999) Pharmacokinetics and stability of the ch14.18-interleukin-2 fusion protein in mice. Cancer Immunol Immunother 48: 219
24. Klausner R D, Lippincott-Schwartz J, Bonifacino J S (1990) The T cell antigen receptor: insights into organelle biology. Annu Rev Cell Biol 6: 403
25. Lewis L D, Cole B F, Wallace P K, Fisher J L, Waugh M, Guyre P M, Fanger M W, Curnow R T, Kaufman P A, Emstoff M S (2001) Pharmacokinetic-pharmacodynamic relationships of the bispecific antibody MDX-H210 when administered in combination with interferon gamma: a multiple-dose phase-I study in patients with advanced cancer which overexpresses HER-2/neu. J Immunol Methods 248: 149
26. Lin A Y, Devaux B, Green A, Sagerstrom C, Elliott J F, Davis M M (1990) Expression of T cell antigen receptor heterodimers in a lipid-linked form. Science 249: 677
27. Lode H N, Xiang R, Dreier T, Varki N M, Gillies S D, Reisfeld R A (1998) Natural killer cell-mediated eradication of neuroblastoma metastases to bone marrow by targeted interleukin-2 therapy. Blood 91: 1706
28. Lode H N, Xiang R, Varki N M, Dolman C S, Gillies S D, Reisfeld R A (1997) Targeted interleukin-2 therapy for spontaneous neuroblastoma metastases to bone marrow. J Natl Cancer Inst 89: 1586
29. Lustgarten J, Marks J, Sherman L A (1999) Redirecting effector T cells through their IL-2 receptors. J Immunol 162: 359
30. McLaughlin R, O'Hanlon D, McHale T, Connolly C E, Given H F (2001) Prognostic implications of p53 and bcl-2 expression in 108 women with stage two breast cancer. Ir J Med Sci 170: 11
31. Motzer R J, Rakhit A, Ginsberg M, Rittweger K, Vuky J, Yu R, Fettner S, Hooftman L (2001) Phase I trial of 40-kd branched pegylated interferon alfa-2a for patients with advanced renal cell carcinoma. J Clin Oncol 19: 1312
32. Motzer R J, Rakhit A, Schwartz L H, Olencki T, Malone T M, Sandstrom K, Nadeau R, Parmar H, Bukowski R (1998) Phase I trial of subcutaneous recombinant human interleukin-12 in patients with advanced renal cell carcinoma. Clin Cancer Res 4: 1183
33. Nastala C L, Edington H D, McKinney T G, Tahara H, Nalesnik M A, Brunda M J, Gately M K, Wolf S F, Schreiber R D, Storkus W J, et al. (1994) Recombinant IL-12 administration induces tumor regression in association with IFN-gamma production. J Immunol 153: 1697
34. Pardoll D M (1995) Paracrine cytokine adjuvants in cancer immunotherapy. Annu Rev Immunol 13: 399
35. Peng L S, Penichet M L, Morrison S L (1999) A single-chain IL-12 IgG3 antibody fusion protein retains antibody specificity and IL-12 bioactivity and demonstrates antitumor activity. J Immunol 163: 250
36. Penichet M L, Harvill E T, Morrison S L (1997) Antibody-IL-2 fusion proteins: a novel strategy for immune protection. Hum Antibodies 8: 106
37. Posey J A, Raspet R, Verma U, Deo Y M, Keller T, Marshall J L, Hodgson J, Mazumder A, Hawkins M J (1999) A pilot trial of GM-CSF and MDX-H210 in patients with erbB-2-positive advanced malignancies. J Immunother 22: 371
38. Pullarkat V, Deo Y, Link J, Spears L, Marty V, Curnow R, Groshen S, Gee C, Weber J S (1999) A phase I study of a HER2/neu bispecific antibody with granulocyte-colony-stimulating factor in patients with metastatic breast cancer that overexpresses HER2/neu. Cancer Immunol Immunother 48: 9
39. Reddy K R, Wright T L, Pockros P J, Shiffman M, Everson G, Reindollar R, Fried M W, Purdum P P 3rd, Jensen D, Smith C, et al. (2001) Efficacy and safety of pegylated (40-kd) interferon alpha-2a compared with interferon alpha-2a in noncirrhotic patients with chronic hepatitis C. Hepatology 33: 433
40. Rosenberg S A, Lotze M T, Muul L M, Chang A E, Avis F P, Leitman S, Linehan W M, Robertson C N, Lee R E, Rubin J T, et al (1987) A progress report on the treatment of 157 patients with advanced cancer using lymphokine-activated killer cells and interleukin-2 or high-dose interleukin-2 alone. N Engl J Med 316: 889
41. Rosenberg S A, Lotze M T, Yang J C, Aebersold P M, Linehan W M, Seipp C A, White D E (1989) Experience with the use of high-dose interleukin-2 in the treatment of 652 cancer patients. Ann Surg 210: 474
42. Rosenberg S A, Spiess P J, Schwarz S (1983) In vivo administration of Interleukin-2 enhances specific alloimmune responses. Transplantation 35: 631
43. Rosenberg S A, Yang J C, White D E, Steinberg S M (1998) Durability of complete responses in patients with metastatic cancer treated with high-dose interleukin-2: identification of the antigens mediating response. Ann Surg 228: 307
44. Royal R E, Steinberg S M, Krouse R S, Heywood G, White D E, Hwu P, Marincola F M, Parkinson D R, Schwartzentruber D J, Topalian S L, et al. (1996) Correlates of Response to IL-2 Therapy in Patients Treated for Metastatic Renal Cancer and Melanoma. Cancer J Sci Am 2: 91
45. Sherman L A, Hesse S V, Irwin M J, La Face D, Peterson P (1992) Selecting T cell receptors with high affinity for self-MHC by decreasing the contribution of CD8. Science 258: 815
46. Sondel P M, Kohler P C, Hank J A, Moore K H, Rosenthal N S, Sosman J A, Bechhofer R, Storer B (1988) Clinical and immunological effects of recombinant interleukin 2 given by repetitive weekly cycles to patients with cancer. Cancer Res 48: 2561
47. Sosman J A, Hank J A, Moore K H, Borchert A, Schell K, Kohler P C, Goldstein D, Bechhofer R, Storer B, Albertini M R, et al. (1991) Prolonged interleukin-2 (IL-2) treatment can augment immune activation without enhancing antitumor activity in renal cell carcinoma. Cancer Invest 9: 35
48. Temmim L, Baker H, Sinowatz F (2001) Immunohistochemical detection of p53 protein expression in breast cancer in young Kuwaiti women. Anticancer Res 21: 743
49. Theobald M, Biggs J, Dittmer D, Levine A J, Sherman L A (1995) Targeting p53 as a general tumor antigen. Proc Natl Acad Sci USA 92: 11993
50. Theobald M, Biggs J, Hernandez J, Lustgarten J, Labadie C, Sherman L A (1997) Tolerance to p53 by A2.1-restricted cytotoxic T lymphocytes. J Exp Med 185: 833
51. thor Straten P, Guldberg P, Schrama D, Andersen M A, Moerch U, Seremet T, Siedel C, Reisfeld R A, Becker J C (2001) In situ cytokine therapy: redistribution of clonally expanded T cells. Eur J Immunol 31: 250
52. Tsung K, Meko J B, Peplinski G R, Tsung Y L, Norton J A (1997) IL-12 induces T helper 1-directed antitumor response. J Immunol 158: 3359
53. van Golen K L, Risin S, Staroselsky A, Berger D, Tainsky M A, Pathak S, Price J E (1996) Predominance of the metastatic phenotype in hybrids formed by fusion of mouse and human melanoma clones. Clin Exp Metastasis. 14: 95
54. Weber S, Traunecker A, Oliveri F, Gerhard W, Karjalainen K (1992) Specific low-affinity recognition of major histocompatibility complex plus peptide by soluble T-cell receptor. Nature 356: 793
55. Weil-Hillman G, Voss S D, Fisch P, Schell K, Hank J A, Sosman J A, Sugamura K, Sondel P M (1990) Natural killer cells activated by interleukin 2 treatment in vivo respond to interleukin 2 primarily through the p75 receptor and maintain the p55 (TAC) negative phenotype. Cancer Res 50: 2683
56. Wiebke E A, Rosenberg S A, Lotze M T (1988) Acute immunologic effects of interleukin-2 therapy in cancer patients: decreased delayed type hypersensitivity response and decreased proliferative response to soluble antigens. J Clin Oncol 6: 1440.
57. O'Herron S M, Lebowitz M S, Bieler J G, al-Ramadi B K, Utz U, Bothwell A L M and Schneck J P (1997) Analysis of the expression of peptide-major histocompatibility complexes using high affinity soluble divalent T cell receptors. J Exp Med 186: 1333.

The disclosures of all references mentioned herein are incorporated herein by reference. The invention has been described with reference to preferred embodiments thereof. However, it will be appreciated that those skilled in the art, upon consideration of this disclosure, may make modifications and improvements within the spirit and scope of the invention.

What is claimed is:

1. A soluble T cell receptor (TCR) fusion complex comprising a Vα chain, a Vβ chain, a Cβ chain, and an interleukin-2 (IL-2) domain, wherein the TCR is capable of binding to a p53 peptide in the context of an MHC molecule, wherein the MHC molecule comprises an HLA-A2 molecule, and wherein the soluble TCR fusion complex comprises the amino acid sequence set forth in SEQ ID NO: 16.

2. The soluble TCR fusion complex of claim 1, wherein the Vα chain comprises residues 21-133 of SEQ ID NO: 16 and wherein the Vβ chain comprises residues 158-271 of SEQ ID NO: 16.

3. The soluble TCR fusion complex of claim 1, wherein the IL-2 domain comprises residues 415-548 of SEQ ID NO: 16.

4. The soluble TCR fusion complex of claim 1, wherein the Vα chain is covalently linked to the Vβ chain by a peptide linker sequence.

5. The soluble TCR fusion complex of claim 4, wherein the peptide linker sequence comprises the amino acid sequence set forth in SEQ ID NO: 17.

6. The soluble TCR fusion complex of claim 5, wherein the Cβ chain is covalently linked to the IL-2 domain by a peptide linker sequence.

7. The soluble TCR fusion complex of claim 6, wherein the peptide linker sequence comprises residues 398-414 of SEQ ID NO: 16.

8. The soluble TCR of claim 1, wherein said TCR comprises a heterodimer.

9. The soluble TCR of claim 1, wherein said TCR comprises a single chain TCR (scTCR).

10. The soluble TCR of claim 1, wherein the Cβ chain comprises residues 272-397 of SEQ ID NO: 16.

* * * * *

SEQUENCE LISTING

```
<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Asn Ala Lys Thr Thr Ala Pro Ser Val Tyr Pro Leu Ala Pro Val
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Glu Glu Glu Tyr Met Pro Met Glu
1               5
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggtggccc agccggccat ggcccagtca gtgacgcagc                    40

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaggtgacta gtgtctggct ttataattag                               30

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5 gggggggctcg agcaattcaa aagtcattca gactc                        35

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaggtggagc ccggggtctg ctcggcccca ggc                           33

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccaccggtc agtcagtgac gcagccc                                  27

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtggagttcg aaaaggtgac ttacgtttgt ctgctcggcc ccag               44

<210> SEQ ID NO 9
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgataagtgt acttacgttt tcattattcc atcggcatgt actcttcttc ctctcg    56

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtggagatcg ataagtgtac ttacgttttc attatcgcga tccggagtta acgtctgctc    60
ggccccag                                                              68

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taggtgtccg gagcacctac ttcaagttct ac                                   32

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taggtgtcgc gaagttagtg ttgagatgat g                                    31

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
actcactata gggctcgagc ggc                                             23

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctgtcctga gaccgaggat cttttaactg                                      30

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttgtttgttt gcaatctgtg cttttgatgg                                    30

<210> SEQ ID NO 16
<211> LENGTH: 559
<212> TYPE: PRT
<213> ORGANISM: Artificial Sequence
<220> FEATURE:
<223> OTHER INFORMATION: Description of Artificial Sequence: Synthetic
      fusion protein sequence

<400> SEQUENCE: 16
```

Met Glu Thr Asp Thr Leu Leu Leu Trp Val Leu Leu Leu Trp Val Pro
 1               5                  10                  15

Gly Ser Thr Gly Gln Ser Val Thr Gln Pro Asp Ala Arg Val Thr Val
            20                  25                  30

Ser Glu Gly Ala Ser Leu Gln Leu Arg Cys Lys Tyr Ser Tyr Ser Gly
        35                  40                  45

Thr Pro Tyr Leu Phe Trp Tyr Val Gln Tyr Pro Arg Gln Gly Leu Gln
    50                  55                  60

Leu Leu Leu Lys Tyr Tyr Ser Gly Asp Pro Val Val Gln Gly Val Asn
65                  70                  75                  80

Gly Phe Glu Ala Glu Phe Ser Lys Ser Asn Ser Ser Phe His Leu Arg
                85                  90                  95

Lys Ala Ser Val His Trp Ser Asp Ser Ala Val Tyr Phe Cys Val Leu
            100                 105                 110

Ser Glu Asp Ser Asn Tyr Gln Leu Ile Trp Gly Ser Gly Thr Lys Leu
        115                 120                 125

Ile Ile Lys Pro Asp Thr Ser Gly Gly Gly Ser Gly Gly Gly
    130                 135                 140

Ser Gly Gly Gly Ser Gly Gly Gly Ser Ser Asn Ser Lys
145                 150                 155                 160

Val Ile Gln Thr Pro Arg Tyr Leu Val Lys Gly Gln Gly Gln Lys Ala
                165                 170                 175

Lys Met Arg Cys Ile Pro Glu Lys Gly His Pro Val Val Phe Trp Tyr
            180                 185                 190

Gln Gln Asn Lys Asn Asn Glu Phe Lys Phe Leu Ile Asn Phe Gln Asn
        195                 200                 205

Gln Glu Val Leu Gln Gln Ile Asp Met Thr Glu Lys Arg Phe Ser Ala
    210                 215                 220

Glu Cys Pro Ser Asn Ser Pro Cys Ser Leu Glu Ile Gln Ser Ser Glu
225                 230                 235                 240

Ala Gly Asp Ser Ala Leu Tyr Leu Cys Ala Ser Ser Leu Ser Gly Gly
                245                 250                 255

Gly Thr Glu Val Phe Phe Gly Lys Gly Thr Arg Leu Thr Val Val Glu
            260                 265                 270

Asp Leu Arg Asn Val Thr Pro Pro Lys Val Ser Leu Phe Glu Pro Ser
        275                 280                 285

```
Lys Ala Glu Ile Ala Asn Lys Gln Lys Ala Thr Leu Val Cys Leu Ala
    290                 295                 300
Arg Gly Phe Phe Pro Asp His Val Glu Leu Ser Trp Trp Val Asn Gly
305                 310                 315                 320
Lys Glu Val His Ser Gly Val Ser Thr Asp Pro Gln Ala Tyr Lys Glu
                325                 330                 335
Ser Asn Tyr Ser Tyr Cys Leu Ser Ser Arg Leu Arg Val Ser Ala Thr
            340                 345                 350
Phe Trp His Asn Pro Arg Asn His Phe Arg Cys Gln Val Gln Phe His
        355                 360                 365
Gly Leu Ser Glu Glu Asp Lys Trp Pro Glu Gly Ser Pro Lys Pro Val
    370                 375                 380
Thr Gln Asn Ile Ser Ala Glu Ala Trp Gly Arg Ala Asp Val Asn Ala
385                 390                 395                 400
Lys Thr Thr Ala Pro Ser Val Tyr Pro Leu Ala Pro Val Ser Gly Ala
                405                 410                 415
Pro Thr Ser Ser Ser Thr Lys Lys Thr Gln Leu Gln Leu Glu His Leu
            420                 425                 430
Leu Leu Asp Leu Gln Met Ile Leu Asn Gly Ile Asn Asn Tyr Lys Asn
        435                 440                 445
Pro Lys Leu Thr Arg Met Leu Thr Phe Lys Phe Tyr Met Pro Lys Lys
    450                 455                 460
Ala Thr Glu Leu Lys His Leu Gln Cys Leu Glu Glu Glu Leu Lys Pro
465                 470                 475                 480
Leu Glu Glu Val Leu Asn Leu Ala Gln Ser Lys Asn Phe His Leu Arg
                485                 490                 495
Pro Arg Asp Leu Ile Ser Asn Ile Asn Val Ile Val Leu Glu Leu Lys
            500                 505                 510
Gly Ser Glu Thr Thr Phe Met Cys Glu Tyr Ala Asp Glu Thr Ala Thr
        515                 520                 525
Ile Val Glu Phe Leu Asn Arg Trp Ile Thr Phe Cys Gln Ser Ile Ile
    530                 535                 540
Ser Thr Leu Thr Ser Arg Glu Glu Glu Glu Tyr Met Pro Met Glu
545                 550                 555

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Ser Gly Gly Gly Gly Ser Gly
  1               5                  10                  15

Gly Gly Gly Ser
            20
```